(12) United States Patent
Bourget et al.

(10) Patent No.: US 12,097,373 B2
(45) Date of Patent: Sep. 24, 2024

(54) CONTROL POLICY SETTINGS FOR ELECTRICAL STIMULATION THERAPY

(71) Applicant: Medtronic, Inc., Minneapolis, MN (US)

(72) Inventors: Duane L. Bourget, Andover, MN (US); Kristin N. Hageman, Dayton, MN (US); Hank Bink, Golden Valley, MN (US); Jiashu Li, Mounds View, MN (US); Laura Ann Skarie, Minnetonka, MN (US)

(73) Assignee: Medtronic, Inc., Minneapolis, MN (US)

( * ) Notice: Subject to any disclaimer, the term of this patent is extended or adjusted under 35 U.S.C. 154(b) by 818 days.

(21) Appl. No.: 17/183,997

(22) Filed: Feb. 24, 2021

(65) Prior Publication Data

US 2021/0387002 A1    Dec. 16, 2021

Related U.S. Application Data

(60) Provisional application No. 63/037,361, filed on Jun. 10, 2020.

(51) Int. Cl.
*A61N 1/36*    (2006.01)
*A61N 1/372*    (2006.01)

(52) U.S. Cl.
CPC ..... *A61N 1/36132* (2013.01); *A61N 1/36062* (2017.08); *A61N 1/36139* (2013.01);
(Continued)

(58) Field of Classification Search
CPC ............ A61N 1/36132; A61N 1/36062; A61N 1/36139; A61N 1/37241; A61N 1/37247;
(Continued)

(56) References Cited

U.S. PATENT DOCUMENTS

| 5,603,726 A | 2/1997 | Schulman et al. |
| 5,800,465 A | 9/1998 | Thompson et al. |

(Continued)

FOREIGN PATENT DOCUMENTS

| CN | 105792745 A | 7/2016 |
| EP | 0613390 A1 | 9/1994 |

(Continued)

OTHER PUBLICATIONS

"St. Jude's Prodigy Neurostimulator with Burst Technology," Medgadget, Mar. 20, 2014, 4 pp.

(Continued)

*Primary Examiner* — Eugene T Wu
(74) *Attorney, Agent, or Firm* — Shumaker & Sieffert, P.A.

(57) ABSTRACT

This disclosure is directed to devices, systems, and techniques for controlling electrical stimulation. In some examples, a system includes a user interface and processing circuitry. The processing circuitry is configured to output, for display by the user interface, a message requesting the patient perform a set of actions, receive, from the user interface, user input indicative of a patient response associated with the set of actions, and determine, based on the user input, one or more adjustments to a control policy which controls electrical stimulation delivered by a medical device based on a plurality of evoked compound action potentials (ECAPs) sensed by the medical device.

25 Claims, 23 Drawing Sheets

(52) U.S. Cl.
CPC ..... *A61N 1/37241* (2013.01); *A61N 1/37247* (2013.01); *A61N 1/3615* (2013.01); *A61N 1/36167* (2013.01)

(58) Field of Classification Search
CPC .............. A61N 1/3615; A61N 1/36167; A61N 1/0531; A61N 1/0534; A61N 1/0553; A61N 1/0556; A61N 1/36067; A61N 1/36096; A61N 1/36146; A61N 1/36064; A61N 1/36071; A61N 1/36107; A61N 1/36153; A61N 1/36157; A61N 1/36171; A61N 1/36175; A61N 1/36135; A61B 2562/0219
See application file for complete search history.

(56) References Cited

U.S. PATENT DOCUMENTS

| | | |
|---|---|---|
| 5,908,392 A | 6/1999 | Wilson et al. |
| 6,157,861 A | 12/2000 | Faltys et al. |
| 6,205,360 B1 | 3/2001 | Carter |
| 6,289,247 B1 | 9/2001 | Faltys et al. |
| 6,314,325 B1 | 11/2001 | Fitz |
| 6,421,566 B1 | 7/2002 | Holsheimer |
| 6,505,078 B1 | 1/2003 | King et al. |
| 6,675,046 B2 | 1/2004 | Holsheimer |
| 6,850,802 B2 | 2/2005 | Holsheimer |
| 6,988,006 B2 | 1/2006 | King et al. |
| 7,076,292 B2 | 7/2006 | Forsberg |
| 7,206,640 B1 | 4/2007 | Overstreet |
| 7,333,858 B2 | 2/2008 | Killian et al. |
| 7,577,480 B2 | 8/2009 | Zeijlemaker |
| 7,616,999 B2 | 11/2009 | Overstreet et al. |
| 7,657,318 B2 | 2/2010 | King et al. |
| 7,689,289 B2 | 3/2010 | King |
| 7,742,810 B2 | 6/2010 | Moffitt et al. |
| 7,792,583 B2 | 9/2010 | Miesel et al. |
| 8,036,747 B2 | 10/2011 | Thacker et al. |
| 8,090,446 B2 | 1/2012 | Fowler et al. |
| 8,504,150 B2 | 8/2013 | Skelton |
| 8,515,549 B2 | 8/2013 | Panken et al. |
| 8,620,441 B2 | 12/2013 | Greenberg et al. |
| 8,676,329 B2 | 3/2014 | Wacnik et al. |
| 8,694,108 B2 | 4/2014 | Alataris et al. |
| 8,708,934 B2 | 4/2014 | Skelton et al. |
| 8,712,533 B2 | 4/2014 | Alataris et al. |
| 8,712,534 B2 | 4/2014 | Wei |
| 8,751,009 B2 | 6/2014 | Wacnik |
| 8,897,888 B2 | 11/2014 | Parker et al. |
| 8,918,177 B2 | 12/2014 | Gauthier |
| 8,923,984 B2 | 12/2014 | Parker et al. |
| 8,958,885 B2 | 2/2015 | Panken et al. |
| 9,002,460 B2 | 4/2015 | Parker |
| 9,072,910 B2 | 7/2015 | Parker et al. |
| 9,084,900 B2 | 7/2015 | Hershey et al. |
| 9,089,714 B2 | 7/2015 | Robinson |
| 9,089,715 B2 | 7/2015 | Parker et al. |
| 9,138,582 B2 | 9/2015 | Doan et al. |
| 9,155,892 B2 | 10/2015 | Parker et al. |
| 9,283,373 B2 | 3/2016 | Parker et al. |
| 9,302,112 B2 | 4/2016 | Bornzin et al. |
| 9,339,655 B2 | 5/2016 | Carbunaru |
| 9,364,667 B1 | 6/2016 | Dinsmoor et al. |
| 9,381,356 B2 | 7/2016 | Parker et al. |
| 9,386,934 B2 | 7/2016 | Parker et al. |
| 9,387,325 B1 | 7/2016 | Min et al. |
| 9,511,231 B1 | 12/2016 | Kent et al. |
| 9,553,148 B2 | 1/2017 | Carcieri |
| 9,566,439 B2 | 2/2017 | Single et al. |
| 9,597,507 B2 | 3/2017 | Johanek et al. |
| 9,700,713 B2 | 7/2017 | Robinson et al. |
| 9,872,990 B2 | 1/2018 | Parker et al. |
| 9,993,646 B2 | 6/2018 | Parramon et al. |
| 10,183,168 B2 | 1/2019 | Baru et al. |
| 10,327,654 B2 | 6/2019 | Strahl et al. |
| 10,569,088 B2 | 2/2020 | Dinsmoor et al. |
| 10,933,242 B2 | 3/2021 | Torgerson |
| 2004/0267333 A1 | 12/2004 | Kronberg |
| 2008/0033508 A1 | 2/2008 | Frei et al. |
| 2008/0058651 A1 | 3/2008 | Shen et al. |
| 2008/0221640 A1 | 9/2008 | Overstreet et al. |
| 2008/0300655 A1 | 12/2008 | Cholette |
| 2011/0054570 A1 | 3/2011 | Lane |
| 2011/0071589 A1 | 3/2011 | Starkebaum et al. |
| 2011/0077712 A1 | 3/2011 | Killian |
| 2011/0125223 A1 | 5/2011 | Carbunaru et al. |
| 2012/0155188 A1 | 6/2012 | Buettner et al. |
| 2012/0265028 A1 | 10/2012 | Hughes et al. |
| 2013/0085406 A1 | 4/2013 | Gunderson et al. |
| 2013/0208390 A1 | 8/2013 | Singh et al. |
| 2013/0268021 A1 | 10/2013 | Moffitt |
| 2013/0289664 A1 | 10/2013 | Johanek |
| 2013/0289683 A1 | 10/2013 | Parker et al. |
| 2014/0005753 A1 | 1/2014 | Carbunaru |
| 2014/0025146 A1 | 1/2014 | Alataris et al. |
| 2014/0031896 A1 | 1/2014 | Alataris et al. |
| 2014/0031905 A1 | 1/2014 | Irazoqui et al. |
| 2014/0074189 A1 | 3/2014 | Moffitt |
| 2014/0142656 A1 | 5/2014 | Alataris et al. |
| 2014/0142673 A1 | 5/2014 | Alataris et al. |
| 2014/0194772 A1 | 7/2014 | Single et al. |
| 2014/0236042 A1 | 8/2014 | Parker et al. |
| 2014/0236257 A1 | 8/2014 | Parker et al. |
| 2014/0243924 A1 | 8/2014 | Zhu et al. |
| 2014/0243926 A1 | 8/2014 | Carcieri et al. |
| 2014/0243931 A1 | 8/2014 | Parker et al. |
| 2014/0277282 A1 | 9/2014 | Jaax |
| 2014/0288577 A1 | 9/2014 | Robinson et al. |
| 2014/0293737 A1 | 10/2014 | Parker et al. |
| 2014/0296936 A1 | 10/2014 | Alataris et al. |
| 2014/0324143 A1 | 10/2014 | Robinson et al. |
| 2014/0371813 A1 | 12/2014 | King et al. |
| 2014/0378941 A1 | 12/2014 | Su et al. |
| 2014/0379043 A1 | 12/2014 | Howard |
| 2015/0005842 A1 | 1/2015 | Lee et al. |
| 2015/0012068 A1* | 1/2015 | Bradley .............. A61N 1/36071 607/62 |
| 2015/0032181 A1 | 1/2015 | Baynham et al. |
| 2015/0057729 A1 | 2/2015 | Parker et al. |
| 2015/0127062 A1 | 5/2015 | Holley et al. |
| 2015/0173636 A1 | 6/2015 | Mokelke et al. |
| 2015/0179177 A1 | 6/2015 | Nagao |
| 2015/0282725 A1 | 10/2015 | Single |
| 2015/0313487 A1 | 11/2015 | Single et al. |
| 2015/0360031 A1 | 12/2015 | Bornzin et al. |
| 2015/0374999 A1 | 12/2015 | Parker et al. |
| 2016/0082252 A1 | 3/2016 | Hershey et al. |
| 2016/0121124 A1 | 5/2016 | Johanek et al. |
| 2016/0129272 A1 | 5/2016 | Hou et al. |
| 2016/0136420 A1 | 5/2016 | Brink et al. |
| 2016/0157769 A1 | 6/2016 | Min et al. |
| 2016/0158550 A1 | 6/2016 | Hou et al. |
| 2016/0166164 A1 | 6/2016 | Obradovic et al. |
| 2016/0175594 A1 | 6/2016 | Min et al. |
| 2016/0206883 A1 | 7/2016 | Bornzin et al. |
| 2016/0287126 A1 | 10/2016 | Parker et al. |
| 2016/0287182 A1 | 10/2016 | Single |
| 2016/0339251 A1 | 11/2016 | Kent et al. |
| 2016/0346534 A1 | 12/2016 | Isaacson et al. |
| 2016/0361542 A1 | 12/2016 | Kaula et al. |
| 2017/0001017 A9 | 1/2017 | Parker et al. |
| 2017/0049345 A1 | 2/2017 | Single |
| 2017/0071490 A1 | 3/2017 | Parker et al. |
| 2017/0135624 A1 | 5/2017 | Parker |
| 2017/0173332 A1 | 6/2017 | Overstreet |
| 2017/0209695 A1 | 7/2017 | Solomon |
| 2017/0216587 A1* | 8/2017 | Parker ................ A61N 1/36139 |
| 2017/0216602 A1 | 8/2017 | Waataja et al. |
| 2017/0296823 A1 | 10/2017 | Hershey et al. |
| 2017/0361101 A1 | 12/2017 | Single |
| 2017/0361103 A1 | 12/2017 | Hadjiyski |
| 2018/0056073 A1 | 3/2018 | Torgerson |
| 2018/0078769 A1 | 3/2018 | Dinsmoor et al. |
| 2018/0110464 A1 | 4/2018 | Annoni et al. |

(56) References Cited

U.S. PATENT DOCUMENTS

| | | | |
|---|---|---|---|
| 2018/0110987 A1 | 4/2018 | Parker | |
| 2018/0117335 A1 | 5/2018 | Parker et al. | |
| 2018/0126169 A1 | 5/2018 | Hou et al. | |
| 2018/0132760 A1 | 5/2018 | Parker | |
| 2018/0140842 A1 | 5/2018 | Ó Laighin et al. | |
| 2018/0303368 A1 | 10/2018 | Zhang | |
| 2019/0099601 A1 | 4/2019 | Torgerson | |
| 2019/0105496 A1 | 4/2019 | Min et al. | |
| 2019/0168000 A1 | 6/2019 | Laird-Wah | |
| 2019/0209844 A1 | 7/2019 | Esteller et al. | |
| 2019/0388692 A1* | 12/2019 | Dinsmoor | A61N 1/36071 |
| 2019/0388695 A1 | 12/2019 | Dinsmoor et al. | |
| 2020/0155023 A1 | 5/2020 | Lashghari et al. | |
| 2020/0171312 A1 | 6/2020 | Dinsmoor et al. | |
| 2020/0171313 A1 | 6/2020 | Dinsmoor et al. | |
| 2021/0101007 A1 | 4/2021 | Hamner et al. | |
| 2021/0121699 A1 | 4/2021 | Dinsmoor et al. | |
| 2021/0187298 A1 | 6/2021 | Dinsmoor et al. | |
| 2021/0252289 A1* | 8/2021 | Esteller | A61N 1/36062 |

FOREIGN PATENT DOCUMENTS

| | | |
|---|---|---|
| EP | 2396072 B1 | 3/2013 |
| EP | 3013413 A1 | 5/2016 |
| EP | 3024540 B1 | 10/2018 |
| JP | 2018513714 A1 | 5/2018 |
| WO | 9405371 | 3/1994 |
| WO | 2002009808 A1 | 2/2002 |
| WO | 2010058178 A1 | 5/2010 |
| WO | 2012155188 | 11/2012 |
| WO | 2012155188 A1 | 11/2012 |
| WO | 2014/210373 A1 | 12/2014 |
| WO | 2015070281 A1 | 5/2015 |
| WO | 2015143509 A1 | 10/2015 |
| WO | 2015179177 A1 | 11/2015 |
| WO | 2015179281 A2 | 11/2015 |
| WO | 2016011512 A1 | 1/2016 |
| WO | 2016090420 A1 | 6/2016 |
| WO | 2016090436 A1 | 6/2016 |
| WO | 2016191808 A1 | 12/2016 |
| WO | 2017100866 A1 | 6/2017 |
| WO | 2017106503 A1 | 6/2017 |
| WO | 2017173493 A1 | 10/2017 |
| WO | 2017184238 A1 | 10/2017 |
| WO | 2017219096 A1 | 12/2017 |
| WO | 2018/080754 A1 | 5/2018 |
| WO | 2018080753 A1 | 5/2018 |
| WO | 2018106813 A1 | 6/2018 |
| WO | 2019178634 A1 | 9/2019 |
| WO | 2019204884 A1 | 10/2019 |
| WO | 2019231794 A1 | 12/2019 |
| WO | 2020087135 A1 | 5/2020 |

OTHER PUBLICATIONS

Abejon MD "Back pain coverage with spinal cord stimulation: A different treatment for each patient," International Neuromodulation Society. Jun. 10, 2015; 567, Abstract Only, 1 pp.

Abeloos MD "High density stimulation as an alternative to uncomfortable cervical tonic spinal cord stimulation: case report," International Neuromodulation Society 12th World Congress, Jun. 11-15, 2015, Abstract Only, 1 pp.

Breel et al., "High Density Stimulation: A novel programming paradigm for the treatment of chronic pain," International Neuromodulation Society (INS) 12th World Congress; Jun. 9, 2015, Abstract Only, 1 pp.

Crosby et al., "Modulation of activity and conduction in single dorsal column axons by kilohertz-frequency spinal cord stimulation," American Physiological Society, published online Oct. 19, 2016, 27 pp.

Cuellar MD PhD, et al., "Effect of high-frequency alternating current on spinal afferent nociceptive transmission," Neuromodulation: Technology at the Neural Interface; Jul.-Aug. 2013;16(4): pp. 318-327.

Cui et al., "Effect of spinal cord stimulation on tactile hypersensitivity in mononeuropathic rats is potentiated by simultaneous GABA. sub B. and adenosine receptor activation," Neuroscience Letters 247: Apr. 1998; pp. 183-186.

Cui et al., "Spinal cord stimulation attenuates augmented dorsal horn release of excitatory amino acids in mononeuropathy via a GABAergic mechanism," Pain 73, Oct. 1997, pp. 87-95.

De Ridder et al., "Burst spinal cord stimulation for limb and back pain," World neurosurgery, Nov. 2013; 80(5):642-649, e641.

De Ridder MD PhD et al., "Burst spinal cord stimulation: toward paresthesia-free pain suppression," Neurosurgery. May 2010; 66(5): 986-990.

Downey, "Asynchronous Neuromuscular Electrical Stimulation," University of Florida, 2015, accessed on Jul. 18, 2016, 107 pp.

Duyvendak MD et al., "High density stimulation: a novel programming paradigm for the treatment of chronic back and leg pain," Abstracts, International Neuromodulation Society 12th World Congress: Jun. 11-15, 2015, 1 pp.

Gao et al., "Effects of spinal cord stimulation with "standard clinical" and higher frequencies on peripheral blood flow in rats," Brain Res., 1313: (2010) available online Dec. 3, 2009 pp. 53-61.

Grider DO/PhD et al., "High Frequency (1000 Hz) Stimulation Using Commercially Available Implantable Pulse Generator," North American Neuromodulation Society. Dec. 2013, Abstract Only, 2 pp.

Guan MD PhD et al., "Spinal cord stimulation-induced analgesia: electrical stimulation of dorsal column and dorsal roots attenuates dorsal horn neuronal excitability in neuropathic rats," Anesthesiology. Dec. 2010; 113(6): pp. 1392-1405.

Guan, "Spinal Cord Stimulation: Neurophysiological and Neurochemical Mechanisms of Action" Curr Pain Headache Rep DOI 10.1007s11916-014-0260-4, Mar. 8, 2012, pp. 217-225.

Holsheimer, "Computer modelling of spinal cord stimulation and its contribution to therapeutic efficacy," Spinal Cord Aug. 1998, 36: pp. 531-540.

Hubscher et al., "Convergence and cross talk in urogenital neural circuitries," J. Neurophysiol 110: 1997-2005, first published Aug. 7, 2013, 9 pp.

Hunt et al. "The molecular dynamics of pain control," Nature Reviews Neuroscience, vol. 2, Feb. 2001, pp. 83-91.

Kemler MD et al., "Spinal cord stimulation in patients with chronic reflex sympathetic dystrophy," N Engl J Med, Aug. 31, 2000; 343(9):pp. 618-624.

Kilgore PhD et al., "Reversible Nerve Conduction Block Using Kilohertz Frequency Alternating Current," Neuromodulation. Aug. 2013, pp. 242-255.

Kumar et al., "Spinal cord stimulation versus conventional medical management for neuropathic pain: a multicentre randomised controlled trial in patients with failed back surgery syndrome," Pain Jul. 2007; 132(1-2): 179-188.

Likar et al., "High density spinal cord stimulation: a multi-center experience," Abstracts, International Neuromodulation Society 12th World Congress; Jun. 11-15, 2015, 1 pp.

Maeda et al., "Increased c-fos immunoreactivity in the spinal cord and brain following spinal cord stimulation is frequency-dependent," Brain Res. Mar. 9, 2009;1259: pp. 40-50, available online Jan. 6, 2009.

Maeda et al., "Low frequencies, but not high frequencies of bi-polar spinal cord stimulation reduce cutaneous and muscle hyperalgesia induced by nerve injury," Pain; Feb. 2008; 138(1): pp. 143-152.

Maggi et al., "Effect of urethane anesthesia on the micturition reflex in capsaicin-treated rats." Journal of the Autonomic Nervous System, Jan. 1990, 30(3): 247-251.

North MD et al., "Clinical outcomes of 1 kHz subperception spinal cord stimulation (SCS): Results of a prospective randomized controlled crossover trial," Abstracts, International Neuromodulation Society, Jun. 2015, 1 pp.

North MD et al., "Spinal cord stimulation versus repeated lumbosacral spine surgery for chronic pain: a randomized, controlled trial," Neurosurgery, Jan. 2005; 56(1): 98-106; discussion 106-107.

(56) References Cited

OTHER PUBLICATIONS

Ranck Jr. et al., "Which elements are excited in electrical stimulation of mammalian central nervous system: a review," Brain Research, Nov. 21, 1975; 98(3): pp. 417-440.
Replogle MD. et al., "Case Series Comparing Moderate (1000 Hz) Versus Conventional Frequency Stimulation During Spinal Cord Stimulator Trials," North American Neuromodulation Society. 2014, 1 pp. Applicant points out in accordance with MPEP 609.04(a) that the 2014 year of publication is sufficiently earlier than the effective U.S. filing date of the present application, and any foreign priority date that the particular month of publication is not in issue.
Sato et al., "Spinal cord stimulation reduces hypersensitivity through activation of opioid receptors in a frequency-dependent manner," Eur J Pain. Apr. 2013 (4): pp. 551-561, first published Oct. 5, 2012.
Schu MD, PhD et al., "A prospective, randomised, double-blind, placebo-controlled study to examine the effectiveness of burst spinal cord stimulation patterns for the treatment of failed back surgery syndrome," Neuromodulation. Apr. 2014; 17(5): pp. 443-450.
Shechter MD et al., "Conventional and kilohertz-frequency spinal cord stimulation produces intensity- and frequency-dependent inhibition of mechnical hypersensitivity in a rat model of neuropathic pain," Anesthesiology, Aug. 2013; 119(2): pp. 422-432.
Sluka, et al., "High-frequency, but not low-frequency, transcutaneous electrical nerve stimulation reduces aspartate and glutamate release in the spinal cord dorsal horn," J Neurochem. Oct. 17, 2005; 95(6); pp. 1794-1801.
Smith et al., "Successful use of high-frequency spinal cord stimulation following traditional treatment failure," Stereotact Funct Neurosurg. Apr. 1, 2015; 93(3): pp. 190-193.
Snellings et al., "Effects of stimulation site and stimulation parameters on bladder inhibition by electrical nerve stimulation," BJU International, Jul. 2012, pp. 136-143, first published Jan. 19, 2012.
Song MD Phd et al., "Efficacy of kilohertz-frequency and conventional spinal cord stimulation in rat models of different pain conditions," Neuromodulation Jan. 2014; 17(3): pp. 226-234.
Sweet MD et al., "High Frequency vs. Burst Stimulation Patterns for Dorsal Column Stimulation: The Importance of Charge," American Association of Neurological Surgeons, Abstract, Apr. 4, 2014, 2 pp.
Walter et al., "Inhibiting the hyperreflexic bladder with electrical stimulation in a spinal animal model." Neurourology and Urodynamics, 1993, 12:241-253. doi: 10.1002/nau.1930120306. Applicant points out in accordance with MPEP 609.04(a) that the 1993 year of publication is sufficiently earlier than the effective U.S. filing date of the present application, and any foreign priority date that the particular month of publication is not in issue.
Wille MD et al., "Altering Conventional to High Density Spinal Cord Stimulation: An Energy Dose-Response Relationship in Neuropathic Pain Therapy," Neuromodulation 2016, Aug. 2016, 9 pp.
Woock et al., "Activation and inhibition of the micturition reflex by penile afferents in the cat," Am J. Physiol Regul Intergre Comp Physiol, published Apr. 23, 2008, pp. R1880-R1889.
Youn et al., "The Effect of High Frequency Stimulation on Sensory Thresholds in Chronic Pain Patients," North American Neuromodulation Society. 2014, 1 pp. Applicant points out in accordance with MPEP 609.04(a) that the 2014 year of publication is sufficiently earlier than the effective U.S. filing date of the present application, and any foreign priority date that the particular month of publication is not in issue.
U.S. Appl. No. 17/065,383, filed Oct. 7, 2020, naming inventors Dinsmoor et al.
U.S. Appl. No. 17/065,282, filed Oct. 7, 2020, naming inventors Dinsmoor et al.
Agnesi et al., "Local Glutamate Release in the Rat Ventral Lateral Thalamus Evoked by High-Frequency Stimulation," Journal of Neural Engineering, vol. 7, No. 2, Apr. 2010, 20 pp.
Vallejo et al., "Effects of Phase Polarity and Charge Balance Spinal Cord Stimulation on Behavior and Gene Expression in a Rat Model of Neuropathic Pain," Neuromodulation Technology at the Neural Interface, vol. 23, No. 1, Apr. 2019, 10 pp.
Youn et al., The Effect of High-Frequency Stimulation on Sensory Thresholds in Chronic Pain Patients, Stereotact Funct Neurosurg, Oct. 8, 2015, pp. 355-359.
Shariati et al., "Evaluating Spinal Cord Stimulation incorporating feedback control using Evoked Compound Action Potential," Saluda Medical, Dec. 2, 2014, 1 pp.
Laird-Wah, "Improving Spinal Cord Stimulation Model-Based Approaches to Evoked Response Telemetry," Aug. 2015, 273 pp.
U.S. Appl. No. 17/184,196, filed Feb. 24, 2021, naming inventors Bourget et al.
U.S. Appl. No. 17/343,201, filed Jun. 9, 2021, naming inventors Kelly et al.
U.S. Appl. No. 16/721,576, filed Dec. 19, 2019, naming inventors Dinsmoor et al.
U.S. Appl. No. 16/721,528, filed Dec. 19, 2019, naming inventors Dinsmoor et al.

\* cited by examiner

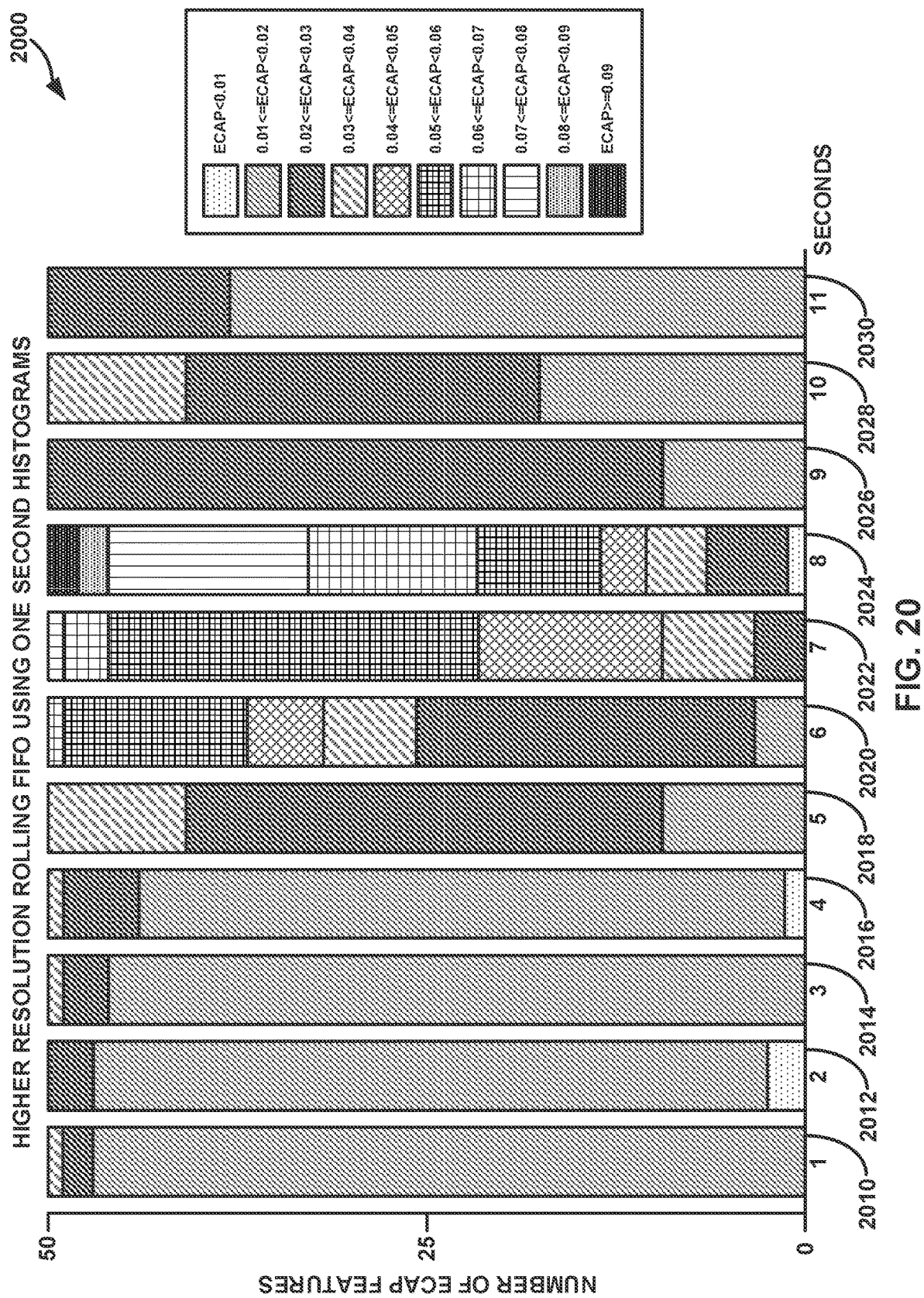

CONTROL POLICY SETTINGS FOR ELECTRICAL STIMULATION THERAPY

This application claims the benefit of U.S. Provisional Patent Application No. 63/037,361, filed on Jun. 10, 2020, the entire content of which is incorporated herein by reference.

TECHNICAL FIELD

This disclosure generally relates to electrical stimulation therapy, and more specifically, control of electrical stimulation therapy.

BACKGROUND

Medical devices may be external or implanted and may be used to deliver electrical stimulation therapy to patients via various tissue sites to treat a variety of symptoms or conditions such as chronic pain, tremor, Parkinson's disease, epilepsy, urinary or fecal incontinence, sexual dysfunction, obesity, or gastroparesis. A medical device may deliver electrical stimulation therapy via one or more leads that include electrodes located proximate to target locations associated with the brain, the spinal cord, pelvic nerves, peripheral nerves, or the gastrointestinal tract of a patient. Stimulation proximate the spinal cord, proximate the sacral nerve, within the brain, and proximate peripheral nerves are often referred to as spinal cord stimulation (SCS), sacral neuromodulation (SNM), deep brain stimulation (DBS), and peripheral nerve stimulation (PNS), respectively.

An evoked compound action potential (ECAP) is synchronous firing of a population of neurons which occurs in response to the application of a stimulus including, in some cases, an electrical stimulus by a medical device. The ECAP may be detectable as being a separate event from the stimulus itself, and the ECAP may reveal characteristics of the effect of the stimulus on the nerve fibers. Electrical stimulation may be delivered to a patient by the medical device in a train of electrical pulses, and parameters of the electrical pulses may include a frequency, an amplitude, a pulse width, and a pulse shape. The parameters of the electrical pulses may be altered in response to sensory input, such as ECAPs sensed in response to the train of electrical pulses. Such alterations may affect the patient's perception of the electrical pulses, or lack thereof.

SUMMARY

In general, the disclosure is directed to devices, systems, and techniques for controlling electrical stimulation therapy. For example, a medical device may control a level of electrical stimulation based on sensing a plurality of evoked compound action potentials (ECAPs). The medical device, in some cases, may reduce an intensity of stimulation pulses in response to a characteristic of a detected ECAP signal exceeding a threshold ECAP value and subsequently increase the intensity of stimulation pulses after the characteristic of later ECAP signals dropping back below the threshold ECAP value. It may be beneficial to change a control policy that define the electrical stimulation in order to account for movement (e.g., one or both of both short-term and long-term migration) of electrodes coupled to the medical device. More specifically, techniques of this disclosure may allow processing circuitry to execute an algorithm for changing (e.g., automatically changing or recommending user changes) the control policy which determines how the medical device changes parameter values that define the electrical stimulation.

The control policy may be established when initiating therapy for the patient, changed periodically over time, or changed in response to a trigger event. The control policy may decrease a likelihood that the stimulation causes a patient to experience an uncomfortable sensation, e.g., "transient overstimulation," and may decrease a likelihood that the stimulation causes the patient to experience a reduced therapeutic benefit. The parameters defining the control policy may similarly need to be first established and then adjusted over time in order to maintain effective therapeutic benefit and reduce the likelihood of undesired stimulation. The medical device or external device associated with the medical device may execute an algorithm that elicits responses from a user and determines adjustments to the parameters that define the control policy based on the user responses.

Additionally, one or more techniques of this disclosure include receiving and analyzing ECAP data corresponding to an event indicated by a patient, where the ECAP data may be a factor in determining recommended changes to the control policy. For example, the medical device may capture ECAP data corresponding to a period of time responsive to receiving patient input indicating an occurrence of an event, the period of time including the occurrence of the event. The medical device may output the ECAP data in a certain format, such as a histogram, for later analysis. A device may use the captured ECAP data in order to recommend one or more changes to the control policy or determine whether to prompt the patient for information that is useful for making one or more changes to the control policy.

In some examples, a system includes a user interface; and processing circuitry. The processing circuitry is configured to output, for display by the user interface, a message requesting the patient perform a set of actions, receive, from the user interface, user input indicative of a patient response associated with the set of actions, and determine, based on the user input, one or more adjustments to a control policy which controls electrical stimulation delivered by a medical device based on at least one evoked compound action potentials (ECAP) sensed by the medical device.

In some examples, a method includes outputting, by processing circuitry for display by the user interface, a message requesting the patient perform a set of actions, receiving, by the processing circuitry from the user interface, user input indicative of a patient response associated with the set of actions, and determining, by the processing circuitry based on the user input, one or more adjustments to a control policy which controls electrical stimulation delivered by a medical device based on at least one evoked compound action potentials (ECAP) sensed by the medical device.

In some examples, a computer-readable medium includes instructions that, when executed by a processor, causes the processor to output, for display by the user interface, a message requesting the patient perform a set of actions, receive, from the user interface, user input indicative of a patient response associated with the set of actions, and determine, based on the user input, one or more adjustments to a control policy which controls electrical stimulation delivered by a medical device based on at least one evoked compound action potentials (ECAP) sensed by the medical device.

In some examples, a medical device includes stimulation generation circuitry configured to deliver electrical stimulation to a patient, where the electrical stimulation therapy includes a plurality of stimulation pulses; sensing circuitry configured to sense one or more evoked compound action potentials (ECAPs), where the sensing circuitry is configured to sense each ECAP of the one or more ECAPs elicited by a respective stimulation pulse of the plurality of stimulation pulses; and processing circuitry configured to store a set of histogram data corresponding to a set of ECAPs of the plurality of ECAPs, the set of ECAPs being sensed by the sensing circuitry over a window of time.

In some examples, a method includes delivering, by stimulation generation circuitry, electrical stimulation to a patient, where the electrical stimulation therapy includes a plurality of stimulation pulses, sensing, by sensing circuitry, one or more evoked compound action potentials (ECAPs), where the sensing circuitry is configured to sense each ECAP of the one or more ECAPs elicited by a respective stimulation pulse of the plurality of stimulation pulses. and storing, by processing circuitry, a set of histogram data corresponding to a set of ECAPs of the plurality of ECAPs, the set of ECAPs being sensed by the sensing circuitry over a window of time.

In some examples, a computer-readable medium includes instructions that, when executed by a processor, causes the processor to deliver electrical stimulation to a patient, where the electrical stimulation therapy includes a plurality of stimulation pulses, sense one or more evoked compound action potentials (ECAPs), where the sensing circuitry is configured to sense each ECAP of the one or more ECAPs elicited by a respective stimulation pulse of the plurality of stimulation pulses, and store a set of histogram data corresponding to a set of ECAPs of the plurality of ECAPs, the set of ECAPs being sensed by the sensing circuitry over a window of time.

The summary is intended to provide an overview of the subject matter described in this disclosure. It is not intended to provide an exclusive or exhaustive explanation of the systems, device, and methods described in detail within the accompanying drawings and description below. Further details of one or more examples of this disclosure are set forth in the accompanying drawings and in the description below. Other features, objects, and advantages will be apparent from the description and drawings, and from the claims.

BRIEF DESCRIPTION OF DRAWINGS

FIG. 20 is a graph which illustrates histogram data including a set of histograms corresponding to the data of the graph of FIG. 19, in accordance with one or more techniques of this disclosure.

Like reference characters denote like elements throughout the description and figures.

DETAILED DESCRIPTION

Figure 1:
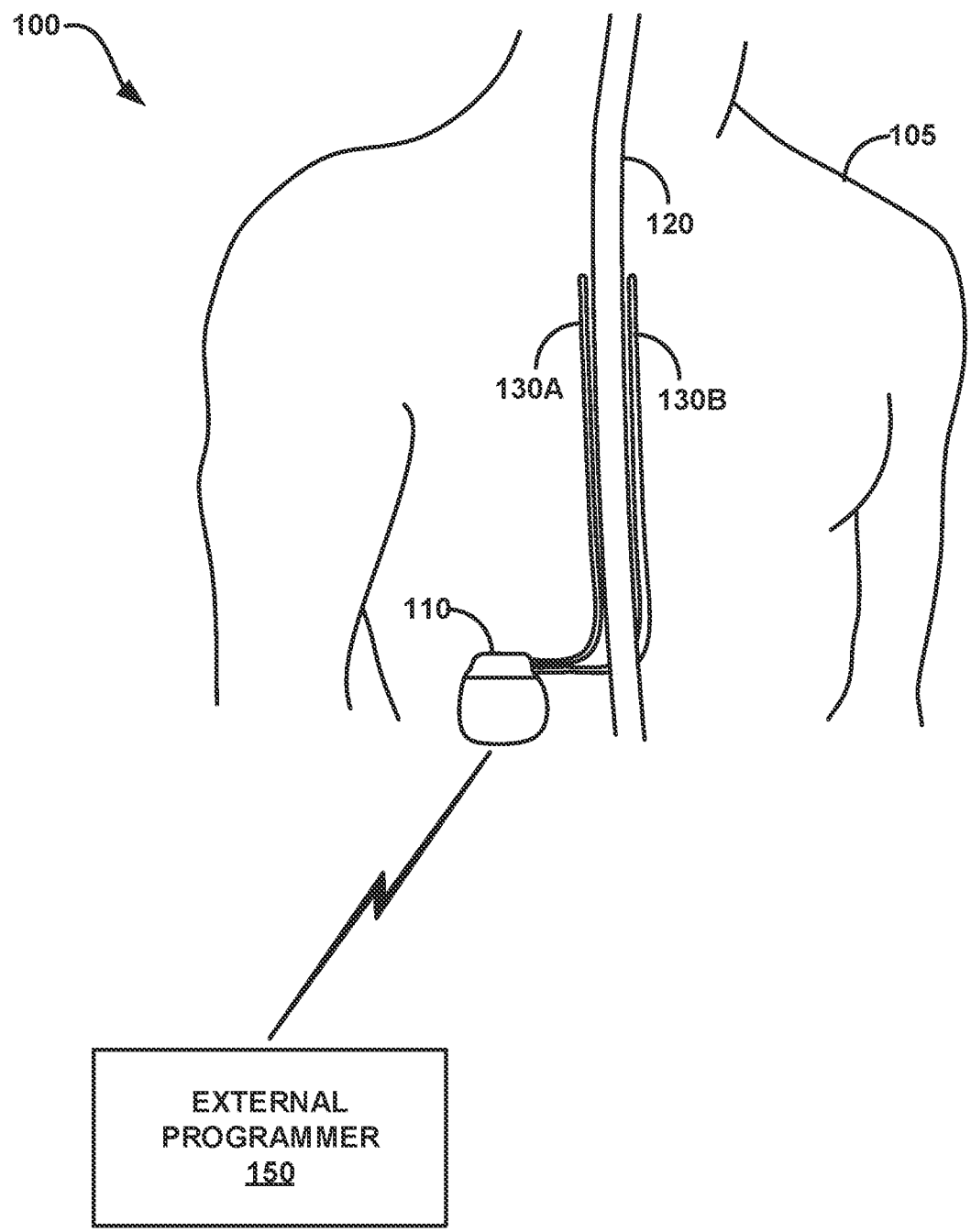
FIG. 1 is a conceptual diagram illustrating an example system that includes an implantable medical device (IMD) configured to deliver spinal cord stimulation (SCS) therapy and an external programmer, in accordance with one or more techniques of this disclosure.

The disclosure describes examples of medical devices, systems, and techniques for setting or adjusting parameters that define a control policy employed by a medical device to make automatic adjustments to stimulation parameters that define electrical stimulation. A medical device may thus automatically adjust electrical stimulation therapy delivered to a patient based on the control policy and one or more characteristics of evoked compound action potentials (ECAPs) received by a medical device. This disclosure describes one or more techniques for adjusting a control policy that the medical device employs to adjust stimulation parameter values that define the electrical stimulation therapy. Electrical stimulation therapy is typically delivered to a target tissue (e.g., one or more nerves or muscle) of a patient via two or more electrodes. Parameters of the electrical stimulation therapy (e.g., electrode combination, voltage or current amplitude, pulse width, pulse frequency, etc.) are selected by a clinician and/or the patient to provide relief from various symptoms, such as pain, muscle disorders, etc.

However, as the patient moves, the distance between the electrodes and the target tissues changes. Posture changes or patient activity can cause electrodes to move closer or farther from target nerves. Lead migration over time may also change this distance between electrodes and target tissue. In some examples, transient patient conditions such as coughing, sneezing, laughing, Valsalva maneuvers, leg lifting, cervical motions, or deep breathing may temporarily cause the stimulation electrodes of the medical device to move closer to the target tissue of the patient, intermittently changing the patient's perception of electrical stimulation therapy.

Since neural recruitment is a function of stimulation intensity and distance between the target tissue and the electrodes, movement of the electrode closer to the target tissue may result in increased perception by the patient (e.g., possible uncomfortable, undesired, or painful sensations), and movement of the electrode further from the target tissue may result in decreased efficacy of the therapy for the patient. For example, if stimulation is held consistent and the stimulation electrodes are moved closer to the target tissue, the patient may perceive the stimulation as more intense, uncomfortable, or even painful. Conversely, consistent stimulation while electrodes are moved farther from target tissue may result in the patient perceiving less intense stimulation which may reduce the therapeutic effect for the patient. Discomfort or pain caused by transient patient conditions may be referred to herein as "transient overstimulation." Therefore, in some examples, it may be beneficial to adjust stimulation parameters in response to patent movement or other conditions that can cause transient overstimulation.

An ECAP may be evoked by a stimulation pulse delivered to nerve fibers of the patient. After being evoked, the ECAP may propagate down the nerve fibers away from the initial stimulus. Sensing circuitry of the medical device may, in some cases, detect this ECAP. Characteristics of the detected ECAP signal may indicate the distance between electrodes and target tissue is changing. For example, a sharp increase in ECAP amplitude over a short period of time (e.g., less than one second) may indicate that the distance between the electrodes and the target tissue is decreasing due to a transient patient action such as a cough. A gradual increase in ECAP amplitude over a longer period of time (e.g., days, weeks, or months) may indicate that the distance between the electrodes and the target tissue is decreasing due to long-term lead migration after the medical device is implanted. It may be beneficial to adjust one or more therapy parameter values in order to prevent the patient from experiencing uncomfortable sensations due to one or both of short-term movement of the electrodes relative to the target tissue and long-term movement of the electrodes relative to the target tissue.

In order to facilitate the sensing of ECAPs, in some examples, the medical device can deliver pulses as part of a therapy (e.g., informed pulses) and also deliver a plurality of control pulses that are designed to elicit detectable ECAPs when the informed pulses do not elicit detectable ECAPs. For example, the control pulse duration may be shorter than the informed pulse to reduce or eliminate the signal artifact that is caused by the informed pulse and prevents or limited detection of the ECAP received at a sensing electrodes). In particular embodiments, the control pulse is short enough that the pulse ends prior to the arrival of all, or most, of the ECAP signal at the sensing electrode(s). In this manner, the medical device may interleave the plurality of control pulses with at least some informed pulses of the plurality of informed pulses. For example, the medical device may deliver informed pulses for a period of time before delivering a control pulse and sensing the corresponding ECAP (if any). The medical device can then resume delivery of the informed pulses for another period of time. In some examples, a pulse duration of the control pulses is less than a pulse duration of the informed pulses and the pulse duration of the control pulses is short enough so that the medical device can sense an individual ECAP for each control pulse. In some examples, the control pulses may provide or contribute to the therapy perceived by the patient.

As described herein, transient patient actions may cause a distance between the electrodes and the target tissue to temporarily change during the respective transient patient action. This transient patient action may include one or more quick movements on the order of seconds or less. During this transient movement, the distance between the electrodes and the target tissue may change and affect the patient's perception of the electrical stimulation therapy delivered by the medical device. If stimulation pulses are constant and the electrodes move closer to the target tissue, the patient may experience a greater or heightened "feeling" or sensation from the therapy. This heightened feeling may be perceived as discomfort or pain (e.g., transient overstimulation) in response to the electrodes moving closer to the target tissue. ECAPs are a measure of neural recruitment because each ECAP signal represents the superposition of electrical potentials generated from axons firing in response to an electrical stimulus (e.g., a stimulation pulse). Changes in a characteristic (e.g., an amplitude of a portion of the signal) of an ECAP signal occurs as a function of how many axons have been activated by the delivered stimulation pulse.

Since ECAPs may provide an indication of the patient's perception of the electrical stimulation therapy, techniques of this disclosure may enable the medical device to decrease one or more parameters of stimulation pulses delivered to the target tissue in response to a first ECAP exceeding a threshold ECAP characteristic value. By decreasing the one or more parameters of the informed pulses, the medical device may prevent the patient from experiencing transient overstimulation. Subsequently, if the medical device determines that sensed ECAPs have later fallen below the threshold ECAP characteristic value, the medical device may restore the stimulation pulses to parameter values that were set before the medical device decreased the one or more parameters of the stimulation pulses in response to the exceeded threshold ECAP characteristic value.

The techniques of this disclosure may provide one or more advantages. For example, it may be beneficial to change the rate at which the medical device decreases and subsequently increases the one or more parameters of the stimulation pulses delivered to the target tissue in response to a transient patient action or in response to a change in control policy. For example, processing circuitry may execute an algorithm which generates one or more recommendations or automatically changes one or more parameters that define a control policy which controls how the medical device changes stimulation parameters based on a physiological signal such as an ECAP characteristic value. Based on receiving an indication that the patient experienced transient overstimulation at a beginning of a transient patient action, the processing circuitry may increase the rate at which the medical device decreases one or more stimulation parameters defining the stimulation pulses responsive to the first ECAP exceeding the threshold ECAP characteristic value. Additionally, or alternatively, based on receiving an indication that the patient experienced transient overstimulation at an end of a transient patient action, the processing circuitry may decrease the rate at which the medical device increases one or more parameters of the stimulation pulses following a decrease in the one or more parameters responsive to the first ECAP exceeding the threshold ECAP characteristic value. Instead of automatically adjusting the parameters of the control policy, the system may generate a recommendation to be presented to a user indicating an appropriate adjustment to the control policy. In this manner a user, such as a clinician or a patient, can accept or confirm the recommended change in some examples.

It may be beneficial to execute an algorithm to output a set of prompts for display to a user interface of an external device, enabling a patient to provide a set of responses indicating aspects of one or more sensations experienced by the patient. For example, the set of prompts may include a prompt for the patient to perform an action. Additionally, the set of prompts may include one or more prompts for the patient to characterize one or more sensations before, during, or after the action performed by the patient. Based on the set of responses, processing circuitry may execute the algorithm to provide one or more changes to the control policy that determines adjustments to stimulation parameters defining therapy delivered to the target tissue. The processing circuitry may automatically change the one or more parameters of the control policy based on the recommendation, but this is not required.

Additionally, the medical device may capture histogram data for analysis. The histogram data, in some examples, may include one or more sets of histograms, where each histogram of the one or more sets of histograms includes a set of bins. A histogram may include a plurality of ECAP amplitudes measured by the medical device over a period of time. A set of histograms may represent a sequence of histograms each corresponding to a period of time (e.g., one second). That is, a first histogram may correspond to a first period of time, a second histogram may correspond to a second period of time directly following the first period of time, a third histogram may correspond to a third period of time directly following the second period of time, and so on. Each histogram of the sequence of histograms may include a set of "bins," where each bin of the set of bins corresponds to a range of ECAP amplitudes. In this way, the medical device or user may identify the quantity of times that the patient may have experienced transient overstimulation based on the histograms and a sequence of histograms over time.

The medical device may capture each set of histograms of the one or more sets of histograms based on one or more triggers. For example, the medical device may capture at least one set of histograms of the one or more sets of histograms based on receiving an instruction to capture a set of histograms, the medical device may capture at least one set of histograms of the one or more sets of histograms based on detecting one or more events which trigger the medical device to capture a set of histograms, the medical device may capture at least one set of histograms of the one or more sets of histograms based on a schedule (e.g., daily, hourly, or any other time interval), or any combination thereof. The medical device may save each set of histograms of the one or more sets of histograms to a memory, where each of set of histograms of the one or more sets of histograms is associated with a timestamp. In this way, processing circuitry may analyze the sets of histograms and the associated timestamps when determining control policy in order to adjust the control policy to improve detection of overstimulation events.

In some examples, the medical device may deliver stimulation that includes pulses (e.g., control pulses) that contribute to therapy and also elicit detectable ECAP signals. In other examples, the medical device may deliver the stimulation pulses to include control pulses and informed pulses. Nerve impulses detectable as the ECAP signal travel quickly along the nerve fiber after the delivered stimulation pulse first depolarizes the nerve. Therefore, if the stimulation pulse delivered by first electrodes has a pulse width that is too long, different electrodes configured to sense the ECAP will sense the stimulation pulse itself as an artifact that obscures the lower amplitude ECAP signal. However, the ECAP signal loses fidelity as the electrical potentials propagate from the electrical stimulus because different nerve fibers propagate electrical potentials at different speeds. Therefore, sensing the ECAP at a far distance from the stimulating electrodes may avoid the artifact caused by a stimulation pulse with a long pulse width, but the ECAP signal may lose fidelity needed to detect changes to the ECAP signal that occur when the electrode to target tissue distance changes. In other words, the system may not be able to identify, at any distance from the stimulation electrodes, ECAPs from stimulation pulses configured to provide a therapy to the patient. Therefore, the medical device may employ control pulses configured to elicit detectable ECAPs and informed pulses that may contribute to therapeutic effects for the patient by may not elicit detectable ECAPs.

In these examples, a medical device is configured to deliver a plurality of informed pulses configured to provide a therapy to the patient and a plurality of control pulses that may or may not contribute to therapy. At least some of the control pulses may elicit a detectable ECAP signal without the primary purpose of providing a therapy to the patient. The control pulses may be interleaved with the delivery of the informed pulses. For example, the medical device may alternate the delivery of informed pulses with control pulses such that a control pulse is delivered, and an ECAP signal is sensed, between consecutive informed pulses. In some examples, multiple control pulses are delivered, and respective ECAP signals sensed, between the delivery of consecutive informed pulses. In some examples, multiple informed pulses will be delivered between consecutive control pulses. In any case, the informed pulses may be delivered according to a predetermined pulse frequency selected so that the informed pulses can produce a therapeutic result for the patient. One or more control pulses are then delivered, and the respective ECAP signals sensed, within one or more time windows between consecutive informed pulses delivered according to the predetermined pulse frequency. In this manner, a medical device can deliver informed pulses from the medical device uninterrupted while ECAPs are sensed from control pulses delivered during times at which the informed pulses are not being delivered. In other examples described herein, ECAPs are sensed by the medical device in response to the informed pulses delivered by the medical device, and control pulses are not used to elicit ECAPs.

According to the examples described herein, a medical device may be configured to deliver stimulation pulses as including control pulses or a combination of a plurality of control pulses and a plurality of informed pulses. The plurality of control pulses, in some cases, may be therapeutic and contribute to therapy received by the patient. In other examples, the plurality of the control pulses may be non-therapeutic and not contribute to the therapy received by the patient. Put another way, the control pulses configured to elicit detectable ECAPs may or may not contribute to alleviating the patient's condition or symptoms of the patient's condition. In contrast to control pulses, informed pulses may not elicit a detectable ECAP or the system may not utilize ECAPs from informed pulses as feedback to control therapy. Therefore, the medical device or other component associated with the medical device may determine values of one or more stimulation parameters that at least partially define the informed pulses based on an ECAP signal elicited by a control pulse instead. In this manner, the informed pulse may be informed by the ECAP elicited from a control pulse. The medical device or other component associated with the medical device may determine values of one or more stimulation parameters that at least partially define the control pulses based on an ECAP signal elicited by previous control pulse.

Although electrical stimulation is generally described herein in the form of electrical stimulation pulses, electrical stimulation may be delivered in non-pulse form in other examples. For example, electrical stimulation may be delivered as a signal having various waveform shapes, frequencies, and amplitudes. Therefore, electrical stimulation in the form of a non-pulse signal may be a continuous signal than may have a sinusoidal waveform or other continuous waveform.

FIG. 1 is a conceptual diagram illustrating an example system 100 that includes an implantable medical device (IMD) 110 configured to deliver spinal cord stimulation (SCS) therapy and an external programmer 150, in accordance with one or more techniques of this disclosure. Although the techniques described in this disclosure are generally applicable to a variety of medical devices including external devices and IMDs, application of such techniques to IMDs and, more particularly, implantable electrical stimulators (e.g., neurostimulators) will be described for purposes of illustration. More particularly, the disclosure will refer to an implantable SCS system for purposes of illustration, but without limitation as to other types of medical devices or other therapeutic applications of medical devices.

As shown in FIG. 1, system 100 includes an IMD 110, leads 130A and 130B, and external programmer 150 shown in conjunction with a patient 105, who is ordinarily a human patient. In the example of FIG. 1, IMD 110 is an implantable electrical stimulator that is configured to generate and deliver electrical stimulation therapy to patient 105 via one or more electrodes of electrodes of leads 130A and/or 130B (collectively, "leads 130"), e.g., for relief of chronic pain or other symptoms. In other examples, IMD 110 may be coupled to a single lead carrying multiple electrodes or more than two leads each carrying multiple electrodes. As a part of delivering stimulation pulses of the electrical stimulation therapy, IMD 110 may be configured to generate and deliver control pulses configured to elicit ECAP signals. The control pulses may provide therapy in some examples. In other examples, IMD 110 may deliver informed pulses that contribute to the therapy for the patient, but which do not elicit detectable ECAPs. IMD 110 may be a chronic electrical stimulator that remains implanted within patient 105 for weeks, months, or even years. In other examples, IMD 110 may be a temporary, or trial, stimulator used to screen or evaluate the efficacy of electrical stimulation for chronic therapy. In one example, IMD 110 is implanted within patient 105, while in another example, IMD 110 is an external device coupled to percutaneously implanted leads. In some examples, IMD 110 uses one or more leads, while in other examples, IMD 110 is leadless.

IMD 110 may be constructed of any polymer, metal, or composite material sufficient to house the components of IMD 110 (e.g., components illustrated in FIG. 2) within patient 105. In this example, IMD 110 may be constructed with a biocompatible housing, such as titanium or stainless steel, or a polymeric material such as silicone, polyurethane, or a liquid crystal polymer, and surgically implanted at a site in patient 105 near the pelvis, abdomen, or buttocks. In other examples, IMD 110 may be implanted within other suitable sites within patient 105, which may depend, for example, on the target site within patient 105 for the delivery of electrical stimulation therapy. The outer housing of IMD 110 may be configured to provide a hermetic seal for components, such as a rechargeable or non-rechargeable power source. In addition, in some examples, the outer housing of IMD 110 is selected from a material that facilitates receiving energy to charge the rechargeable power source.

Electrical stimulation energy, which may be constant current or constant voltage-based pulses, for example, is delivered from IMD 110 to one or more target tissue sites of patient 105 via one or more electrodes (not shown) of implantable leads 130. In the example of FIG. 1, leads 130 carry electrodes that are placed adjacent to the target tissue of spinal cord 120. One or more of the electrodes may be disposed at a distal tip of a lead 130 and/or at other positions at intermediate points along the lead. Leads 130 may be implanted and coupled to IMD 110. The electrodes may transfer electrical stimulation generated by an electrical stimulation generator in IMD 110 to tissue of patient 105. Although leads 130 may each be a single lead, lead 130 may include a lead extension or other segments that may aid in implantation or positioning of lead 130. In some other examples, IMD 110 may be a leadless stimulator with one or more arrays of electrodes arranged on a housing of the stimulator rather than leads that extend from the housing. In addition, in some other examples, system 100 may include one lead or more than two leads, each coupled to IMD 110 and directed to similar or different target tissue sites.

The electrodes of leads 130 may be electrode pads on a paddle lead, circular (e.g., ring) electrodes surrounding the body of the lead, conformable electrodes, cuff electrodes, segmented electrodes (e.g., electrodes disposed at different circumferential positions around the lead instead of a continuous ring electrode), any combination thereof (e.g., ring electrodes and segmented electrodes) or any other type of electrodes capable of forming unipolar, bipolar or multipolar electrode combinations for therapy. Ring electrodes arranged at different axial positions at the distal ends of lead 130 will be described for purposes of illustration.

The deployment of electrodes via leads 130 is described for purposes of illustration, but arrays of electrodes may be deployed in different ways. For example, a housing associated with a leadless stimulator may carry arrays of electrodes, e.g., rows and/or columns (or other patterns), to which shifting operations may be applied. Such electrodes may be arranged as surface electrodes, ring electrodes, or protrusions. As a further alternative, electrode arrays may be formed by rows and/or columns of electrodes on one or more paddle leads. In some examples, electrode arrays include electrode segments, which are arranged at respective positions around a periphery of a lead, e.g., arranged in the form of one or more segmented rings around a circumference of a cylindrical lead. In other examples, one or more of leads 130 are linear leads having 8 ring electrodes along the axial length of the lead. In another example, the electrodes are segmented rings arranged in a linear fashion along the axial length of the lead and at the periphery of the lead.

The stimulation parameter of a therapy stimulation program that defines the stimulation pulses of electrical stimulation therapy by IMD 110 through the electrodes of leads 130 may include information identifying which electrodes have been selected for delivery of stimulation according to a stimulation program, the polarities of the selected electrodes, i.e., the electrode combination for the program, and voltage or current amplitude, pulse frequency, pulse width, pulse shape of stimulation delivered by the electrodes. These stimulation parameters of stimulation pulses (e.g., control pulses and/or informed pulses) are typically predetermined parameter values determined prior to delivery of the stimulation pulses (e.g., set according to a stimulation program). However, in some examples, system 100 changes one or more parameter values automatically based on one or more factors or based on user input and/or the control policy.

An ECAP test stimulation program may define stimulation parameter values that define control pulses delivered by IMD 110 through at least some of the electrodes of leads 130. These stimulation parameter values may include information identifying which electrodes have been selected for delivery of control pulses, the polarities of the selected electrodes, i.e., the electrode combination for the program, and voltage or current amplitude, pulse frequency, pulse width, and pulse shape of stimulation delivered by the electrodes. The stimulation signals (e.g., one or more stimulation pulses or a continuous stimulation waveform) defined by the parameters of each ECAP test stimulation program are configured to evoke a compound action potential from nerves. In some examples, the ECAP test stimulation program defines when the control pulses are to be delivered to the patient based on the frequency and/or pulse width of the informed pulses when informed pulse are also delivered. In some examples, the stimulation defined by each ECAP test stimulation program are not intended to provide or contribute to therapy for the patient. In other examples, the stimulation defined by each ECAP test stimulation program may contribute to therapy when the control pulses elicit detectable ECAP signals and contribute to therapy. In this manner, the ECAP test stimulation program may define stimulation parameters the same or similar to the stimulation parameters of therapy stimulation programs.

Although FIG. 1 is directed to SCS therapy, e.g., used to treat pain, in other examples system 100 may be configured to treat any other condition that may benefit from electrical stimulation therapy. For example, system 100 may be used to treat tremor, Parkinson's disease, epilepsy, a pelvic floor disorder (e.g., urinary incontinence or other bladder dysfunction, fecal incontinence, pelvic pain, bowel dysfunction, or sexual dysfunction), obesity, gastroparesis, or psychiatric disorders (e.g., depression, mania, obsessive compulsive disorder, anxiety disorders, and the like). In this manner, system 100 may be configured to provide therapy taking the form of deep brain stimulation (DBS), peripheral nerve stimulation (PNS), peripheral nerve field stimulation (PNFS), cortical stimulation (CS), pelvic floor stimulation, gastrointestinal stimulation, or any other stimulation therapy capable of treating a condition of patient 105.

In some examples, lead 130 includes one or more sensors configured to allow IMD 110 to monitor one or more parameters of patient 105, such as patient activity, pressure, temperature, or other characteristics. The one or more sensors may be provided in addition to, or in place of, therapy delivery by lead 130.

IMD 110 is configured to deliver electrical stimulation therapy to patient 105 via selected combinations of electrodes carried by one or both of leads 130, alone or in combination with an electrode carried by or defined by an outer housing of IMD 110. The target tissue for the electrical stimulation therapy may be any tissue affected by electrical stimulation, which may be in the form of electrical stimulation pulses or continuous waveforms. In some examples, the target tissue includes nerves, smooth muscle or skeletal muscle. In the example illustrated by FIG. 1, the target tissue is tissue proximate spinal cord 120, such as within an intrathecal space or epidural space of spinal cord 120, or, in some examples, adjacent nerves that branch off spinal cord 120. Leads 130 may be introduced into spinal cord 120 in via any suitable region, such as the thoracic, cervical or lumbar regions. Stimulation of spinal cord 120 may, for example, prevent pain signals from traveling through spinal cord 120 and to the brain of patient 105. Patient 105 may perceive the interruption of pain signals as a reduction in pain and, therefore, efficacious therapy results. In other examples, stimulation of spinal cord 120 may produce paresthesia which may be reduce the perception of pain by patient 105, and thus, provide efficacious therapy results.

IMD 110 generates and delivers electrical stimulation therapy to a target stimulation site within patient 105 via the electrodes of leads 130 to patient 105 according to one or more therapy stimulation programs. A therapy stimulation program defines values for one or more parameters that define an aspect of the therapy delivered by IMD 110 according to that program. For example, a therapy stimulation program that controls delivery of stimulation by IMD 110 in the form of pulses may define values for voltage or current pulse amplitude, pulse width, and pulse rate (e.g., pulse frequency) for stimulation pulses delivered by IMD 110 according to that program.

In some examples where ECAP signals cannot be detected from the types of pulses intended to be delivered to provide therapy to the patient, control pulses and informed pulses may be delivered. For example, IMD 110 is configured to deliver control stimulation to patient 105 via a combination of electrodes of leads 130, alone or in combination with an electrode carried by or defined by an outer housing of IMD 110. The tissue targeted by the control stimulation may be the same tissue targeted by the electrical stimulation therapy, but IMD 110 may deliver control stimulation pulses via the same, at least some of the same, or different electrodes. Since control stimulation pulses are delivered in an interleaved manner with informed pulses, a clinician and/or user may select any desired electrode combination for informed pulses. Like the electrical stimulation therapy, the control stimulation may be in the form of electrical stimulation pulses or continuous waveforms. In one example, each control stimulation pulse may include a balanced, bi-phasic square pulse that employs an active recharge phase. However, in other examples, the control stimulation pulses may include a monophasic pulse followed by a passive recharge phase. In other examples, a control pulse may include an imbalanced bi-phasic portion and a passive recharge portion. Although not necessary, a bi-phasic control pulse may include an interphase interval between the positive and negative phase to promote propagation of the nerve impulse in response to the first phase of the bi-phasic pulse. The control stimulation may be delivered without interrupting the delivery of the electrical stimulation informed pulses, such as during the window between consecutive informed pulses. The control pulses may elicit an ECAP signal from the tissue, and IMD 110 may sense the ECAP signal via two or more electrodes on leads 130. In cases where the control stimulation pulses are applied to spinal cord 120, the signal may be sensed by IMD 110 from spinal cord 120.

IMD 110 may deliver control stimulation to a target stimulation site within patient 105 via the electrodes of leads 130 according to one or more ECAP test stimulation programs. The one or more ECAP test stimulation programs may be stored in a storage device of IMD 110. Each ECAP test program of the one or more ECAP test stimulation programs includes values for one or more parameters that define an aspect of the control stimulation delivered by IMD 110 according to that program, such as current or voltage amplitude, pulse width, pulse frequency, electrode combination, and, in some examples timing based on informed pulses to be delivered to patient 105. In some examples, IMD 110 delivers control stimulation to patient 105 according to multiple ECAP test stimulation programs.

A user, such as a clinician or patient 105, may interact with a user interface of an external programmer 150 to program IMD 110. Programming of IMD 110 may refer generally to the generation and transfer of commands, programs, or other information to control the operation of IMD 110. In this manner, IMD 110 may receive the transferred commands and programs from external programmer 150 to control electrical stimulation therapy (e.g., informed pulses) and control stimulation (e.g., control pulses). For example, external programmer 150 may transmit therapy stimulation programs, ECAP test stimulation programs, stimulation parameter adjustments, therapy stimulation program selections, ECAP test program selections, user input, or other information to control the operation of IMD 110, e.g., by wireless telemetry or wired connection. As described herein, stimulation delivered to the patient may include control pulses, and, in some examples, stimulation may include control pulses and informed pulses.

In some cases, external programmer 150 may be characterized as a physician or clinician programmer if it is primarily intended for use by a physician or clinician. In other cases, external programmer 150 may be characterized as a patient programmer if it is primarily intended for use by a patient. A patient programmer may be generally accessible to patient 105 and, in many cases, may be a portable device that may accompany patient 105 throughout the patient's daily routine. For example, a patient programmer may receive input from patient 105 when the patient wishes to terminate or change electrical stimulation therapy. In general, a physician or clinician programmer may support selection and generation of programs by a clinician for use by IMD 110, whereas a patient programmer may support adjustment and selection of such programs by a patient during ordinary use. In other examples, external programmer 150 may include, or be part of, an external charging device that recharges a power source of IMD 110. In this manner, a user may program and charge IMD 110 using one device, or multiple devices.

As described herein, information may be transmitted between external programmer 150 and IMD 110. Therefore, IMD 110 and external programmer 150 may communicate via wireless communication using any techniques known in the art. Examples of communication techniques may include, for example, radiofrequency (RF) telemetry and inductive coupling, but other techniques are also contemplated. In some examples, external programmer 150 includes a communication head that may be placed proximate to the patient's body near the IMD 110 implant site to improve the quality or security of communication between IMD 110 and external programmer 150. Communication between external programmer 150 and IMD 110 may occur during power transmission or separate from power transmission.

In some examples, IMD 110, in response to commands from external programmer 150, delivers electrical stimulation therapy according to a plurality of therapy stimulation programs to a target tissue site of the spinal cord 120 of patient 105 via electrodes (not depicted) on leads 130. In some examples, IMD 110 modifies therapy stimulation programs as therapy needs of patient 105 evolve over time. For example, the modification of the therapy stimulation programs may cause the adjustment of at least one parameter of the plurality of informed pulses. When patient 105 receives the same therapy for an extended period, the efficacy of the therapy may be reduced. In some cases, parameters of the plurality of informed pulses may be automatically updated.

In this disclosure, efficacy of electrical stimulation therapy may be indicated by one or more characteristics (e.g. an amplitude of or between one or more peaks or an area under the curve of one or more peaks) of an action potential that is evoked by a stimulation pulse delivered by IMD 110 (i.e., a characteristic of the ECAP signal). Electrical stimulation therapy delivery by leads 130 of IMD 110 may cause neurons within the target tissue to evoke a compound action potential that travels up and down the target tissue, eventually arriving at sensing electrodes of IMD 110. Furthermore, control stimulation may also elicit at least one ECAP, and ECAPs responsive to control stimulation may also be a surrogate for the effectiveness of the therapy. The amount of action potentials (e.g., number of neurons propagating action potential signals) that are evoked may be based on the various parameters of electrical stimulation pulses such as amplitude, pulse width, frequency, pulse shape (e.g., slew rate at the beginning and/or end of the pulse), etc. The slew rate may define the rate of change of the voltage and/or current amplitude of the pulse at the beginning and/or end of each pulse or each phase within the pulse. For example, a very high slew rate indicates a steep or even near vertical edge of the pulse, and a low slew rate indicates a longer ramp up (or ramp down) in the amplitude of the pulse. In some examples, these parameters contribute to an intensity of the electrical stimulation. In addition, a characteristic of the ECAP signal (e.g., an amplitude) may change based on the distance between the stimulation electrodes and the nerves subject to the electrical field produced by the delivered control stimulation pulses.

In one example, each therapy pulse may have a pulse width greater than approximately 300 μs, such as between approximately 300 µs and 1000 µs (i.e., 1 millisecond) in some examples. At these pulse widths, IMD 110 may not sufficiently detect an ECAP signal because the therapy pulse is also detected as an artifact that obscures the ECAP signal. If ECAPs are not adequately recorded, then ECAPs arriving at IMD 110 cannot be compared to the target ECAP characteristic (e.g. a target ECAP amplitude), and electrical therapy stimulation cannot be altered according to responsive ECAPs. When informed pulses have these longer pulse widths, IMD 110 may deliver control stimulation in the form of control pulses. The control pulses may have pulse widths of less than approximately 300 µs, such as a bi-phasic pulse with each phase having a duration of approximately 100 µs. Since the control pulses may have shorter pulse widths than the informed pulses, the ECAP signal may be sensed and identified following each control pulse and used to inform IMD 110 about any changes that should be made to the informed pulses (and control pulses in some examples). In general, the term "pulse width" refers to the collective duration of every phase, and interphase interval when appropriate, of a single pulse. A single pulse includes a single phase in some examples (i.e., a monophasic pulse) or two or more phases in other examples (e.g., a bi-phasic pulse or a tri-phasic pulse). The pulse width defines a period of time beginning with a start time of a first phase of the pulse and concluding with an end time of a last phase of the pulse (e.g., a biphasic pulse having a positive phase lasting 100 µs, a negative phase lasting 100 µs, and an interphase interval lasting 30 µs defines a pulse width of 230 µs). In another example, a control pulse may include a positive phase lasting 90 µs, a negative phase lasting 90 µs, and an interphase interval lasting 30 µs to define a pulse width of 210 µs In another example, a control pulse may include a positive phase lasting 120 µs, a negative phase lasting 120 µs, and an interphase interval lasting 30 µs to define a pulse width of 270 µs.

As described, the example techniques for adjusting stimulation parameter values for informed pulses are based on comparing the value of a characteristic of a measured ECAP signal to a target ECAP characteristic value. During delivery of control stimulation pulses defined by one or more ECAP test stimulation programs, IMD 110, via two or more electrodes interposed on leads 130, senses electrical potentials of tissue of the spinal cord 120 of patient 105 to measure the electrical activity of the tissue. IMD 110 senses ECAPs from the target tissue of patient 105, e.g., with electrodes on one or more leads 130 and associated sense circuitry. In some examples, IMD 110 receives a signal indicative of the ECAP from one or more sensors, e.g., one or more electrodes and circuitry, internal or external to patient 105. Such an example signal may include a signal indicating an ECAP of the tissue of patient 105. Examples of the one or more sensors include one or more sensors configured to measure a compound action potential of patient 105, or a physiological effect indicative of a compound action potential. For example, to measure a physiological effect indicative of a compound action potential, the one or more sensors may be an accelerometer, a pressure sensor, a bending sensor, a sensor configured to detect a posture of patient 105, or a sensor configured to detect a respiratory function of patient 105. In this manner, although the ECAP may be indicative of a posture change or other patient action, other sensors may also detect similar posture changes or movements using modalities separate from the ECAP. However, in other examples, external programmer 150 receives a signal indicating a compound action potential in the target tissue of patient 105 and transmits a notification to IMD 110.

In the example techniques described in this disclosure, the control stimulation parameters and the target ECAP characteristic values may be initially set at the clinic but may be set and/or adjusted at home by patient 105. Once the target ECAP characteristic values are set, the example techniques allow for automatic adjustment of therapy pulse parameters to maintain consistent volume of neural activation and consistent perception of therapy for the patient when the electrode-to-neuron distance changes. The ability to change the stimulation parameter values may also allow the therapy to have long term efficacy, with the ability to keep the intensity of the stimulation (e.g., as indicated by the ECAP) consistent by comparing the measured ECAP values to the target ECAP characteristic value. IMD 110 may perform these changes without intervention by a physician or patient 105.

In some examples, the system changes the target ECAP characteristic value over a period of time. The system may be programmed to change the target ECAP characteristic in order to adjust the intensity of informed pulses to provide varying sensations to the patient (e.g., increase or decrease the volume of neural activation). In one example, a system may be programmed to oscillate a target ECAP characteristic value between a maximum target ECAP characteristic value and a minimum target ECAP characteristic value at a predetermined frequency to provide a sensation to the patient that may be perceived as a wave or other sensation that may provide therapeutic relief for the patient. The maximum target ECAP characteristic value, the minimum target ECAP characteristic value, and the predetermined frequency may be stored in the storage device of IMD 110 and may be updated in response to a signal from external programmer 150 (e.g., a user request to change the values stored in the storage device of IMD 110). In other examples, the target ECAP characteristic value may be programed to steadily increase or steadily decrease to a baseline target ECAP characteristic value over a period of time. In other examples, external programmer 150 may program the target ECAP characteristic value to automatically change over time according to other predetermined functions or patterns. In other words, the target ECAP characteristic value may be programmed to change incrementally by a predetermined amount or predetermined percentage, the predetermined amount or percentage being selected according to a predetermined function (e.g., sinusoid function, ramp function, exponential function, logarithmic function, or the like). Increments in which the target ECAP characteristic value is changed may be changed for every certain number of pulses or a certain unit of time. Although the system may change the target ECAP characteristic value, received ECAP signals may still be used by the system to adjust one or more parameter values of the informed pulses and/or control pulses in order to meet the target ECAP characteristic value.

In some examples, IMD 110 includes stimulation generation circuitry configured to deliver electrical stimulation therapy to the patient 105, where the electrical stimulation therapy includes a plurality of informed pulses. Additionally, the stimulation generation circuitry of IMD 110 may be configured to deliver a plurality of control pulses, where the plurality of control pulses is interleaved with at least some informed pulses of the plurality of informed pulses. In some examples, IMD 110 includes sensing circuitry configured to detect a plurality of ECAPs, where the sensing circuitry is configured to detect each ECAP of the plurality of ECAPs after a control pulse of the plurality of control pulses and prior to a subsequent therapy pulse of the plurality of informed pulses. Even though the plurality of ECAPs may be received by IMD 110 based on IMD 110 delivering the plurality of control pulses (e.g., the plurality of control pulses may evoke the plurality of ECAPs received by IMD 110), the plurality of ECAPs may indicate an efficacy of the plurality of informed pulses. In other words, although the plurality of ECAPs might, in some cases, not be evoked by the plurality of informed pulses themselves, the plurality of ECAPs may still reveal one or more properties of the plurality of informed pulses or one or more effects of the plurality of informed pulses on patient 105. In some examples, the plurality of informed pulses are delivered by IMD 110 at above a perception threshold, where patient 105 is able to perceive the plurality of informed pulses delivered at above the perception threshold. In other examples, the plurality of informed pulses are delivered by IMD 110 at below a perception threshold, where the patient 105 not able to perceive the plurality of informed pulses delivered at below the perception threshold.

IMD 110 may include processing circuitry which, in some examples, is configured to process the plurality of ECAPs received by the sensing circuitry of IMD 110. For example, the processing circuitry of IMD 110 is configured to determine if a parameter of a first ECAP is greater than a threshold parameter value. The processing circuitry may monitor a characteristic value of each ECAP of the plurality of ECAPs and the first ECAP may be the first ECAP of the plurality of ECAPs recorded by IMD 110 that exceeds the threshold characteristic value. In some examples, the characteristic monitored by IMD 110 may be an ECAP amplitude. The ECAP amplitude may, in some examples, be given by a voltage difference between an N1 ECAP peak and a P2 ECAP peak. More description related to the N1 ECAP peak, and other ECAP peaks may be found below in the FIG. 4 description. In other examples, IMD 110 may monitor another characteristic or more than one characteristic of the plurality of ECAPs, such as current amplitude, slope, slew rate, ECAP frequency, ECAP duration, or any combination thereof. In some examples where the characteristic includes an ECAP amplitude, the threshold ECAP characteristic value may be selected from a range of approximately 5 microvolts ($\mu V$) to approximately 30 $\mu V$.

If the processing circuitry of IMD 110 determines that the characteristic of the first ECAP is greater than the threshold ECAP characteristic value, the processing circuitry may decrement (or reduce) a parameter of a set of informed pulses delivered by the stimulation generation circuitry after the first ECAP. In some examples, in order to decrement the parameter of the set of informed pulses, IMD 110 may decrease a current amplitude of each therapy pulse of each consecutive therapy pulse of the set of informed pulses by a current amplitude value. In other examples, in order to decrement the parameter of the set of informed pulses, IMD 110 may decrease a magnitude of a parameter (e.g., voltage) other than current. Since the plurality of ECAPs may indicate some effects of the therapy delivered by IMD 110 on patient 105, IMD 110 may decrement the parameter of the set of informed pulses in order to improve the therapy delivered to patient 105. In some cases, ECAPs received by IMD 110 exceeding the threshold ECAP characteristic value may indicate to IMD 110 that one or more of leads 130 have moved closer to the target tissue (e.g., spinal cord 120) of patient 105. In these cases, if therapy delivered to spinal cord 120 is maintained at present levels, patient 105 may experience transient overstimulation since the distance between leads 130 and the target tissue of patient 105 is a factor in determining the effects of electrical stimulation therapy on patient 105. Consequently, decrementing the first set of informed pulses based on determining that the first ECAP exceeds the threshold ECAP characteristic value may prevent patient 105 from experiencing transient overstimulation due to the electrical stimulation therapy delivered by IMD 110.

After determining that the first ECAP exceeds the threshold ECAP characteristic value, the processing circuitry of IMD 110 may continue to monitor the plurality of ECAPs detected by the sensing circuitry. In some examples, the processing circuitry of IMD 110 may identify a second ECAP which occurs after the first ECAP, where a characteristic of the second ECAP is less than the threshold ECAP characteristic value. The second ECAP may, in some cases, be a leading ECAP occurring after the first ECAP which includes a characteristic value less than the threshold ECAP characteristic value. In other words, each ECAP occurring between the first ECAP and the second ECAP may include a characteristic value greater than or equal to the threshold ECAP characteristic value. In this manner, since IMD 110 may decrement the informed pulses delivered to patient 105 between the first ECAP and the second ECAP, decreasing a risk that patient 105 experiences transient overstimulation during a period of time extending between the reception of the first ECAP and the reception of the second ECAP. Based on the characteristic of the second ECAP being less than the threshold ECAP characteristic value, the processing circuitry of IMD 110 may increment a parameter of a second set of informed pulses delivered by the stimulation generation circuitry after the second ECAP.

In some examples, IMD 110 may deliver electrical stimulation therapy to patient 105 based on a "control policy." In some examples, IMD 110 stores the control policy in a memory (not illustrated in FIG. 1). The control policy may be set and/or updated by processing circuitry of IMD 110 or processing circuitry of external programmer 150, processing circuitry of one or more other devices, or any combination thereof. The control policy drives one or more therapy configurations of the electrical stimulation therapy delivered by IMD 110. For example, the control policy may determine an amplitude of one or more stimulation pulses delivered by IMD 110, a frequency of electrical stimulation therapy delivered by IMD 110, a response to one or more detected ECAPs (e.g., changes in pulse amplitude and/or pulse frequency), or any combination thereof.

External programmer 150 or another device may include a user interface. Processing circuitry (e.g., processing circuitry of external programmer 150 and/or processing circuitry of IMD 110) may output, for display by the user interface, a message requesting the patient 105 perform a set of actions. The processing circuitry may receive, from the user interface, user input indicative of a patient response associated with the set of actions. Additionally, the processing circuitry may determine, based on the user input, one or more adjustments to a control policy which controls electrical stimulation delivered by IMD 110 based on at least one evoked compound action potentials (ECAP) sensed by IMD 110.

In some examples, responsive to determining the one or more adjustments to the control policy, the processing circuitry is configured to output, to IMD 110 via communication circuitry of external programmer 150, an instruction to configure the one or more adjustments to the control policy, but this is not required. The one or more adjustments may be implemented in other ways.

In some examples, to determine the one or more adjustments to the control policy, the processing circuitry is configured to determine the one or more adjustments in order to cause the control policy to perform any one or combination of: decrease a decrement step size or a decrement step rate of a plurality of stimulation pulses delivered to IMD 110 responsive to one or more events associated with a patient response, increase the decrement step size or the decrement step rate of the plurality of stimulation pulses responsive to the one or more events associated with the patient response, decrease an increment step size or an increment step rate of the plurality of stimulation pulses responsive to the one or more events associated with the patient response, or increase the increment step size or the increment step rate of the plurality of stimulation pulses responsive to the transient one or more events associated with the patient response. The one or more adjustments to the control policy are not meant to be limited to these examples. An adjustment to the control policy may cause the control policy to make any kind of change to the therapy delivered to patient 105 by IMD 110 or another device.

The message requesting patient 105 to perform a set of actions and the user input indicative of the patient response associated with an evaluation technique referred to herein as the "patient guidance wizard" (e.g., a methodology for setting up stimulation therapy and/or control policy for therapy using a user interface to provide and receive information to and from a user such as a clinician and/or patient). The patient guidance wizard may represent a technique in which processing circuitry outputs the message requesting patient 105 to perform an action (e.g., an arch of the back, a cough, or another action). Subsequently, to perform the patient guidance wizard, the processing circuitry may output a set of requests via the user interface of external programmer 150 or another device and receive a set of responses to the set of requests. Each request of the set of requests may include a prompt for information relating to one or more patient sensations corresponding to the action and each response may include information relating to the respective request. Based on the set of responses received from the user interface, the processing circuitry may determine the one or more adjustments to be made to the therapy delivered by patient 105.

In some examples, stimulation generation circuitry of IMD 110 is configured to deliver electrical stimulation to patient 105, where the electrical stimulation therapy includes a plurality of stimulation pulses. Additionally, IMD 110 may include sensing circuitry configured to sense one or more evoked compound action potentials (ECAPs), wherein the sensing circuitry is configured to sense each ECAP of the one or more ECAPs elicited by a respective stimulation pulse of the plurality of stimulation pulses. Processing circuitry of IMD 110 may store histogram data corresponding to a set of ECAPs of the plurality of ECAPs, the set of ECAPs being sensed by the sensing circuitry of IMD 110 over a window of time.

In some examples, the histogram data includes a set of histograms. Each histogram of the set of histograms includes a set of histogram bins. Each histogram bin of the set of histogram bins corresponds to a range of ECAP parameter values, and each histogram bin of the set of histogram bins includes a number of ECAPs of the set of ECAPs that are associated with a parameter value within the respective range of ECAP parameter values. The number of ECAPs in each histogram bin may be any number greater than or equal to zero. The set of histograms may represent a sequence of histograms, where each histogram of the sequence of histograms corresponds to a set of ECAPs detected by IMD 110 during a respective period of time. For example, a set of histogram data may include a sequence of histograms, where each histogram of the sequence of histograms corresponds to a one second window of time. That is, a first histogram of the sequence of histograms corresponds to a first one second window, a second histogram of the sequence of histograms corresponds to a second one second window directly following the first one second window, and so on. However, the sequence of histograms may correspond to periods of time of any length.

In some examples, processing circuitry of IMD 110 may receive, from an external device (e.g., external programmer 150), a user input. IMD 110 may capture, in response to receiving the user input, histogram data from a "rolling buffer" and store the captured histogram data in a memory. IMD 110 may additionally or alternatively capture the histogram data from the rolling buffer in response to detecting a pattern of interest in a set of ECAPs, detecting a pattern in an accelerometer signal, detecting a change in a state of an algorithm, or detecting noise in any on or more signals of IMD 110. The set of histogram data may include data representative of the patient response. That is, IMD 110 may store the histogram data in a "rolling buffer" which updates as time progresses. In some cases, IMD 110 may erase data from the end of the rolling buffer and add data to the beginning of the rolling buffer as time progresses. When IMD 110 receives the user input, which may represent a request to capture histogram data from the rolling buffer, IMD 110 may capture, or permanently save, the histogram data currently in the rolling buffer when IMD 110 receives the user request.

In some examples, IMD 110 may permanently save histogram data without first capturing the histogram data in the rolling buffer. For example, IMD 110 may receive a user report of a start of a patient activity and save a first timestamp corresponding to the start of the patient activity. Additionally, IMD 110 may receive a user report of an end of a patient activity and save a second timestamp corresponding to the end of the patient activity, where the first timestamp corresponds to one of the plurality of second sets of histogram data and the second timestamp corresponds to one of the plurality of second sets of histogram data. IMD 110 may analyze saved histogram data based on the timestamps.

The rolling buffer may correspond to a window of time which extends from a first time to a second time, where the second time represents a current time and the first time represents a point in time before the current time, and where the second time represents a current time or a time in the future. When IMD 110 receives the user input to capture the histogram data in the rolling buffer, IMD 110 may capture the histogram data currently stored in the rolling buffer and the histogram data may correspond to a period of time in which a patient response occurs. That is, the histogram data may include one or more indications (e.g., elevated ECAP amplitudes) which indicate a patient response such as transient overstimulation.

IMD 110 may receive a user request to set one or more histogram parameters for collecting the set of histogram data. The one or more histogram parameters may include a length of a period of time corresponding to each histogram within the histogram data, a range of ECAP parameters corresponding to each histogram bin, or any other parameter associated with the histogram data. IMD 110 may set, based on the user request, the one or more histogram parameters, wherein the one or more histogram parameters include a set of parameter ranges which define one or more histogram bins included in a set of histogram bins of the histogram data.

The histogram data may include a first set of histograms corresponding to stimulation pulse amplitude values of a set of stimulation pulses delivered by the stimulation generation circuitry; and a second set of histograms corresponding to ECAP amplitude values of ECAPs sensed by the sensing circuitry responsive to the set of stimulation pulses delivered by stimulation generation circuitry. In this way, when evaluating the second set of histograms which include ECAP amplitude values, processing circuitry may evaluate the ECAP amplitude values based on the amplitude of the stimulation pulses which evoke the respective ECAPs.

Figure 2:
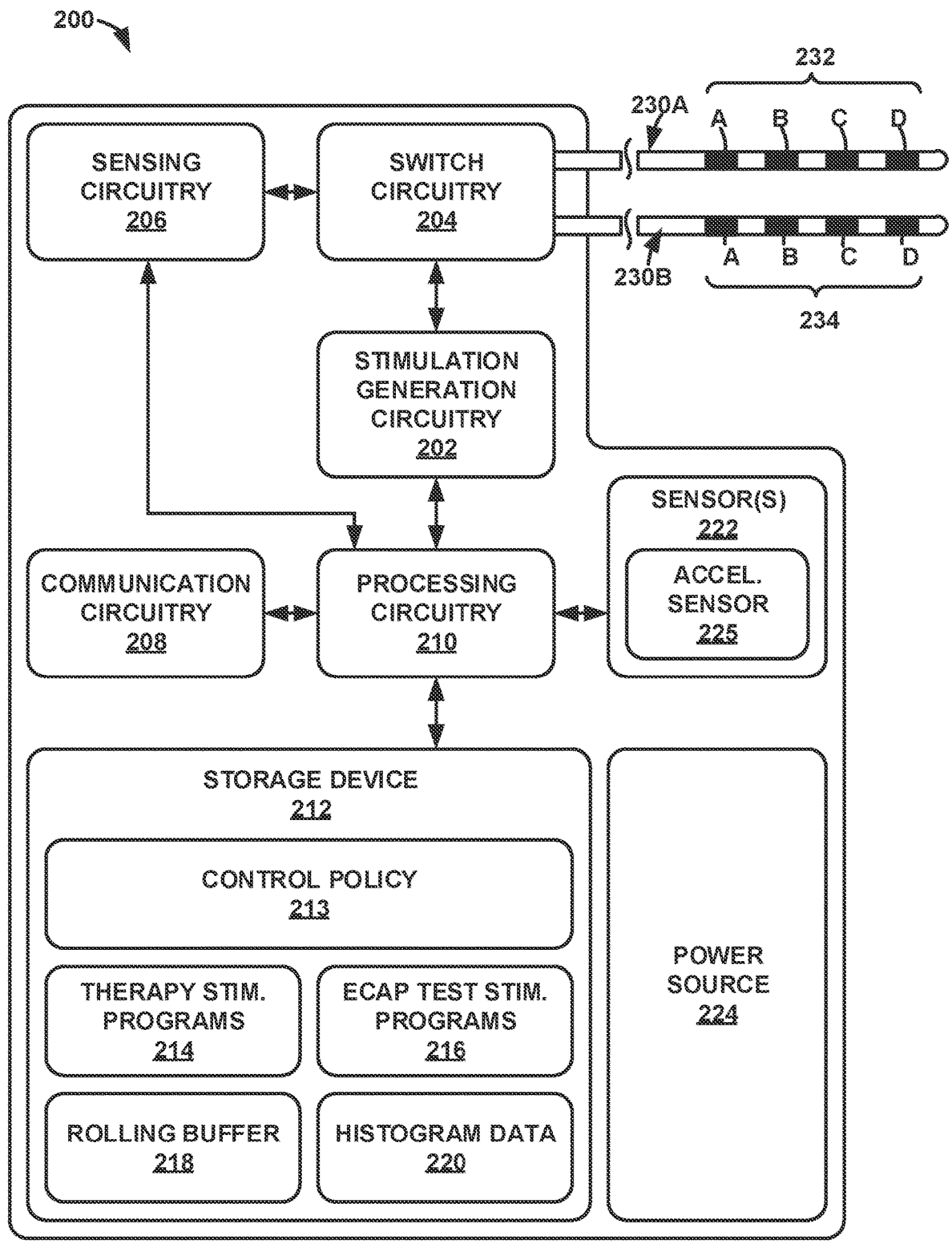
FIG. 2 is a block diagram illustrating an example configuration of components of an IMD, in accordance with one or more techniques of this disclosure.

FIG. 2 is a block diagram illustrating an example configuration of components of IMD 200, in accordance with one or more techniques of this disclosure. IMD 200 may be an example of IMD 110 of FIG. 1. In the example shown in FIG. 2, IMD 200 includes stimulation generation circuitry 202, switch circuitry 204, sensing circuitry 206, communication circuitry 208, processing circuitry 210, storage device 212, sensor(s) 222, and power source 224.

In the example shown in FIG. 2, storage device 212 stores therapy stimulation programs 214 and ECAP test stimulation programs 216 in separate memories within storage device 212 or separate areas within storage device 212. Storage device 212 also stores rolling buffer 218 and histogram data 220. Each stored therapy stimulation program of therapy stimulation programs 214 defines values for a set of electrical stimulation parameters (e.g., a stimulation parameter set), such as a stimulation electrode combination, electrode polarity, current or voltage amplitude, pulse width, pulse rate, and pulse shape. Each stored ECAP test stimulation programs 216 defines values for a set of electrical stimulation parameters (e.g., a control stimulation parameter set), such as a stimulation electrode combination, electrode polarity, current or voltage amplitude, pulse width, pulse rate, and pulse shape. ECAP test stimulation programs 216 may also have additional information such as instructions regarding when to deliver control pulses based on the pulse width and/or frequency of the informed pulses defined in therapy stimulation programs 214. In examples in which control pulses are provided to the patient without the need for informed pulses, a separate ECAP test stimulation program may not be needed. Instead, the ECAP test stimulation program for therapy that only includes control pulses may define the same control pulses as the corresponding therapy stimulation program for those control pulses.

Accordingly, in some examples, stimulation generation circuitry 202 generates electrical stimulation signals in accordance with the electrical stimulation parameters noted above. Other ranges of stimulation parameter values may also be useful and may depend on the target stimulation site within patient 105. While stimulation pulses are described, stimulation signals may be of any form, such as continuous-time signals (e.g., sine waves) or the like. Switch circuitry 204 may include one or more switch arrays, one or more multiplexers, one or more switches (e.g., a switch matrix or other collection of switches), or other electrical circuitry configured to direct stimulation signals from stimulation generation circuitry 202 to one or more of electrodes 232, 234, or directed sensed signals from one or more of electrodes 232, 234 to sensing circuitry 206. In other examples, stimulation generation circuitry 202 and/or sensing circuitry 206 may include sensing circuitry to direct signals to and/or from one or more of electrodes 232, 234, which may or may not also include switch circuitry 204.

Sensing circuitry 206 monitors signals from any combination of electrodes 232, 234. In some examples, sensing circuitry 206 includes one or more amplifiers, filters, and analog-to-digital converters. Sensing circuitry 206 may be used to sense physiological signals, such as ECAPs. In some examples, sensing circuitry 206 detects ECAPs from a particular combination of electrodes 232, 234. In some cases, the particular combination of electrodes for sensing ECAPs includes different electrodes than a set of electrodes 232, 234 used to deliver stimulation pulses. Alternatively, in other cases, the particular combination of electrodes used for sensing ECAPs includes at least one of the same electrodes as a set of electrodes used to deliver stimulation pulses to patient 105. Sensing circuitry 206 may provide signals to an analog-to-digital converter, for conversion into a digital signal for processing, analysis, storage, or output by processing circuitry 210.

Communication circuitry 208 supports wireless communication between IMD 200 and an external programmer (not shown in FIG. 2) or another computing device under the control of processing circuitry 210. Processing circuitry 210 of IMD 200 may receive, as updates to programs, values for various stimulation parameters such as amplitude and electrode combination, from the external programmer via communication circuitry 208. Updates to the therapy stimulation programs 214 and ECAP test stimulation programs 216 may be stored within storage device 212. Communication circuitry 208 in IMD 200, as well as telemetry circuits in other devices and systems described herein, such as the external programmer, may accomplish communication by radiofrequency (RF) communication techniques. In addition, communication circuitry 208 may communicate with an external medical device programmer (not shown in FIG. 2) via proximal inductive interaction of IMD 200 with the external programmer. The external programmer may be one example of external programmer 150 of FIG. 1. Accordingly, communication circuitry 208 may send information to the external programmer on a continuous basis, at periodic intervals, or upon request from IMD 110 or the external programmer.

Processing circuitry 210 may include any one or more of a microprocessor, a controller, a digital signal processor (DSP), an application specific integrated circuit (ASIC), a field-programmable gate array (FPGA), discrete logic circuitry, or any other processing circuitry configured to provide the functions attributed to processing circuitry 210 herein may be embodied as firmware, hardware, software or any combination thereof. Processing circuitry 210 controls stimulation generation circuitry 202 to generate stimulation signals according to therapy stimulation programs 214 and ECAP test stimulation programs 216 stored in storage device 212 to apply stimulation parameter values specified by one or more of programs, such as amplitude, pulse width, pulse rate, and pulse shape of each of the stimulation signals.

In the example shown in FIG. 2, the set of electrodes 232 includes electrodes 232A, 232B, 232C, and 232D, and the set of electrodes 234 includes electrodes 234A, 234B, 234C, and 234D. In other examples, a single lead may include all eight electrodes 232 and 234 along a single axial length of the lead. Processing circuitry 210 also controls stimulation generation circuitry 202 to generate and apply the stimulation signals to selected combinations of electrodes 232, 234. In some examples, stimulation generation circuitry 202 includes a switch circuit (instead of, or in addition to, switch circuitry 204) that may couple stimulation signals to selected conductors within leads 230, which, in turn, deliver the stimulation signals across selected electrodes 232, 234. Such a switch circuit may be a switch array, switch matrix, multiplexer, or any other type of switching circuit configured to selectively couple stimulation energy to selected electrodes 232, 234 and to selectively sense bioelectrical neural signals of a spinal cord of the patient (not shown in FIG. 2) with selected electrodes 232, 234.

In other examples, however, stimulation generation circuitry 202 does not include a switch circuit and switch circuitry 204 does not interface between stimulation generation circuitry 202 and electrodes 232, 234. In these examples, stimulation generation circuitry 202 includes a plurality of pairs of voltage sources, current sources, voltage sinks, or current sinks connected to each of electrodes 232, 234 such that each pair of electrodes has a unique signal circuit. In other words, in these examples, each of electrodes 232, 234 is independently controlled via its own signal circuit (e.g., via a combination of a regulated voltage source and sink or regulated current source and sink), as opposed to switching signals between electrodes 232, 234.

Electrodes 232, 234 on respective leads 230 may be constructed of a variety of different designs. For example, one or both of leads 230 may include one or more electrodes at each longitudinal location along the length of the lead, such as one electrode at different perimeter locations around the perimeter of the lead at each of the locations A, B, C, and D. In one example, the electrodes may be electrically coupled to stimulation generation circuitry 202, e.g., via switch circuitry 204 and/or switching circuitry of the stimulation generation circuitry 202, via respective wires that are straight or coiled within the housing of the lead and run to a connector at the proximal end of the lead. In another example, each of the electrodes of the lead may be electrodes deposited on a thin film. The thin film may include an electrically conductive trace for each electrode that runs the length of the thin film to a proximal end connector. The thin film may then be wrapped (e.g., a helical wrap) around an internal member to form the lead 230. These and other constructions may be used to create a lead with a complex electrode geometry.

Although sensing circuitry 206 is incorporated into a common housing with stimulation generation circuitry 202 and processing circuitry 210 in FIG. 2, in other examples, sensing circuitry 206 may be in a separate housing from IMD 200 and may communicate with processing circuitry 210 via wired or wireless communication techniques.

In some examples, one or more of electrodes 232 and 234 are suitable for sensing the ECAPs. For instance, electrodes 232 and 234 may sense the voltage amplitude of a portion of the ECAP signals, where the sensed voltage amplitude is a characteristic the ECAP signal.

Storage device 212 may be configured to store information within IMD 200 during operation. Storage device 212 may include a computer-readable storage medium or computer-readable storage device. In some examples, storage device 212 includes one or more of a short-term memory or a long-term memory. Storage device 212 may include, for example, random access memory (RAM), dynamic random access memory (DRAM), static random access memory (SRAM), ferroelectric random access memory (FRAM), magnetic discs, optical discs, flash memory, or forms of electrically programmable memory (EPROM) or electrically erasable and programmable memory (EEPROM). In some examples, storage device 212 is used to store data indicative of instructions for execution by processing circuitry 210. As discussed above, storage device 212 is configured to store therapy stimulation programs 214 and ECAP test stimulation programs 216.

In some examples, stimulation generation circuitry 202 may be configured to deliver electrical stimulation therapy to patient 105. The electrical stimulation therapy may, in some cases, include a plurality of informed pulses. Additionally, stimulation generation circuitry 202 may be configured to deliver a plurality of control pulses, where the plurality of control pulses is interleaved with at least some informed pulses of the plurality of informed pulses. Stimulation generation circuitry may deliver the plurality of informed pulses and the plurality of control pulses to target tissue (e.g., spinal cord 120) of patient 105 via electrodes 232, 234 of leads 230. By delivering such informed pulses and control pulses, stimulation generation circuitry 202 may evoke responsive ECAPs in the target tissue, the responsive ECAPs propagating through the target tissue before arriving back at electrodes 232, 234. In some examples, a different combination of electrodes 232, 234 may sense responsive ECAPs than a combination of electrodes 232, 234 that delivers informed pulses and a combination of electrodes 232, 234 that delivers control pulses. Sensing circuitry 206 may be configured to detect the responsive ECAPs via electrodes 232, 234 and leads 230. In other examples, stimulation generation circuitry 202 may be configured to deliver a plurality of control pulses, without any informed pulses, when control pulses also provide therapeutic effect for the patient.

Processing circuitry 210 may, in some cases, direct sensing circuitry 206 to continuously monitor for ECAPs. In other cases, processing circuitry 210 may direct sensing circuitry 206 to may monitor for ECAPs based on signals from sensor(s) 222. For example, processing circuitry 210 may activate sensing circuitry 206 based on an activity level of patient 105 exceeding an activity level threshold (e.g., an accelerometer signal of sensor(s) 222 rises above a threshold). Activating and deactivating sensing circuitry 206 may, in some examples, extend a battery life of power source 224.

In some examples, processing circuitry 210 determines if a characteristic of a first ECAP is greater than a threshold ECAP characteristic value. The threshold ECAP characteristic value may be stored in storage device 212. In some examples, the characteristic of the first ECAP is a voltage amplitude of the first ECAP. In some such examples, the threshold ECAP characteristic value is selected from a range of approximately 10 microvolts (Or) to approximately 20 μV. In other examples, processing circuitry 210 determines if another characteristic (e.g., ECAP current amplitude, ECAP slew rate, area underneath the ECAP, ECAP slope, or ECAP duration) of the first ECAP is greater than the threshold ECAP characteristic value.

If processing circuitry 210 determines that the characteristic of the first ECAP is greater than the threshold ECAP characteristic value, processing circuitry 210 is configured to activate a decrement mode, altering at least one parameter of each therapy pulse of a set of informed pulses delivered by IMD 200 after the first ECAP is sensed by sensing circuitry 206. Additionally, while the decrement mode is activated, processing circuitry 210 may change at least one parameter of each control pulse of a set of control pulses delivered by IMD 200 after the first ECAP is sensed by sensing circuitry 206. In some examples, the at least one parameter of the informed pulses and the at least one parameter of the control pulses adjusted by processing circuitry 210 during the decrement mode includes a stimulation current amplitude. In some such examples, during the decrement mode, processing circuitry 210 decreases an electrical current amplitude of each consecutive stimulation pulse (e.g., each therapy pulse and each control pulse) delivered by IMD 200. In other examples, the at least one parameter of the stimulation pulses adjusted by processing circuitry 210 during the decrement mode include any combination of electrical current amplitude, electrical voltage amplitude, slew rate, pulse shape, pulse frequency, or pulse duration.

In the example illustrated by FIG. 2, the decrement mode is stored in storage device 212 as a part of control policy 213. The decrement mode may include a list of instructions which enable processing circuitry 210 to adjust parameters of stimulation pulses according to a function. In some examples, when the decrement mode is activated, processing circuitry 210 decreases a parameter (e.g., an electrical current) of each consecutive therapy pulse and each consecutive control pulse according to a linear function. In other examples, when the decrement mode is activated, processing circuitry 210 decreases a parameter (e.g., an electrical current) of each consecutive therapy pulse and each consecutive control pulse according to an exponential function, a logarithmic function, or a piecewise function. While the decrement mode is activated, sensing circuitry 206 may continue to monitor responsive ECAPs. In turn, sensing circuitry 206 may detect ECAPs responsive to control pulses delivered by IMD 200.

Throughout the decrement mode, processing circuitry may monitor ECAPs responsive to stimulation pulses. Processing circuitry 210 may determine if a characteristic of a second ECAP is less than the threshold ECAP characteristic value. The second ECAP may, in some cases, be the leading ECAP occurring after the first ECAP which is less than the threshold ECAP characteristic value. In other words, each ECAP recorded by sensing circuitry 206 between the first ECAP and the second ECAP is greater than or equal to the threshold ECAP characteristic value. Based on the characteristic of the second ECAP being less than the threshold ECAP characteristic value, processing circuitry 210 may deactivate the decrement mode and activate an increment mode, thus altering at least one parameter of each therapy pulse of a set of informed pulses delivered by IMD 200 after the second ECAP is sensed by sensing circuitry 206. Additionally, while the increment mode is activated, processing circuitry 210 may change at least one parameter of each control pulse of a set of control pulses delivered by IMD 200 after the second ECAP is sensed by sensing circuitry 206.

In some examples, the at least one parameter of the informed pulses and the at least one parameter of the control pulses adjusted by processing circuitry 210 during the increment mode includes a stimulation current amplitude. In some such examples, during the increment mode, processing circuitry 210 increases an electrical current amplitude of each consecutive stimulation pulse (e.g., each therapy pulse and each control pulse) delivered by IMD 200. In other examples, the at least one parameter of the stimulation pulses adjusted by processing circuitry 210 during the increment mode include any combination of electrical current amplitude, electrical voltage amplitude, slew rate, pulse shape, pulse frequency, or pulse duration.

In the example illustrated by FIG. 2, the increment mode is stored in storage device 212 as a part of control policy 213. The increment mode may include a list of instructions which enable processing circuitry 210 to adjust parameters of stimulation pulses according to a function. In some examples, when the increment mode is activated, processing circuitry 210 increases a parameter (e.g., an electrical current) of each consecutive therapy pulse and each consecutive control pulse according to a linear function. In other examples, when the increment mode is activated, processing circuitry 210 increases a parameter (e.g., an electrical current) of each consecutive therapy pulse and each consecutive control pulse according to a non-linear function, such as an exponential function, a logarithmic function, or a piecewise function. While the increment mode is activated, sensing circuitry 206 may continue to monitor responsive ECAPs. In turn, sensing circuitry 206 may detect ECAPs responsive to control pulses delivered by IMD 200.

Processing circuitry 210 may complete the increment mode such that the one or more parameters of the stimulation pulses return to baseline parameter values of stimulation pulses delivered before processing circuitry 210 activates the decrement mode (e.g., before sensing circuitry 206 detects the first ECAP). By first decrementing and subsequently incrementing stimulation pulses in response to ECAPs exceeding a threshold ECAP characteristic value, processing circuitry 210 may prevent patient 105 from experiencing transient overstimulation or decrease a severity of transient overstimulation experienced by patient 105.

Although, in some examples, sensing circuitry 206 senses ECAPs which occur in response to control pulses delivered according to ECAP test stimulation programs 216, in other examples, sensing circuitry 206 senses ECAPs which occur in response to informed pulses delivered according to therapy stimulation programs 214. The techniques of this disclosure may enable IMD 200 to toggle the decrement mode and the increment mode using any combination of ECAPs corresponding to informed pulses and ECAPs corresponding to control pulses.

Sensor(s) 222 may include one or more sensing elements that sense values of a respective patient parameter. As described, electrodes 232 and 234 may be the electrodes that sense the characteristic value of the ECAP. Sensor(s) 222 may include one or more accelerometers, optical sensors, chemical sensors, temperature sensors, pressure sensors, or any other types of sensors. Sensor(s) 222 may output patient parameter values that may be used as feedback to control delivery of therapy. For example, sensor(s) 222 may indicate patient activity, and processing circuitry 210 may increase the frequency of control pulses and ECAP sensing in response to detecting increased patient activity. In one example, processing circuitry 210 may initiate control pulses and corresponding ECAP sensing in response to a signal from sensor(s) 222 indicating that patient activity has exceeded an activity threshold. Conversely, processing circuitry 210 may decrease the frequency of control pulses and ECAP sensing in response to detecting decreased patient activity. For example, in response to sensor(s) 222 no longer indicating that the sensed patient activity exceeds a threshold, processing circuitry 210 may suspend or stop delivery of control pulses and ECAP sensing. In this manner, processing circuitry 210 may dynamically deliver control pulses and sense ECAP signals based on patient activity to reduce power consumption of the system when the electrode-to-neuron distance is not likely to change and increase system response to ECAP changes when electrode-to-neuron distance is likely to change. IMD 200 may include additional sensors within the housing of IMD 200 and/or coupled via one of leads 130 or other leads. In addition, IMD 200 may receive sensor signals wirelessly from remote sensors via communication circuitry 208, for example. In some examples, one or more of these remote sensors may be external to patient (e.g., carried on the external surface of the skin, attached to clothing, or otherwise positioned external to patient 105). In some examples, signals from sensor(s) 222 indicate a position or body state (e.g., sleeping, awake, sitting, standing, or the like), and processing circuitry 210 may select target ECAP characteristic values according to the indicated position or body state.

Power source 224 is configured to deliver operating power to the components of IMD 200. Power source 224 may include a battery and a power generation circuit to produce the operating power. In some examples, the battery is rechargeable to allow extended operation. In some examples, recharging is accomplished through proximal inductive interaction between an external charger and an inductive charging coil within IMD 200. Power source 224 may include any one or more of a plurality of different battery types, such as nickel cadmium batteries and lithium ion batteries.

Figure 3:
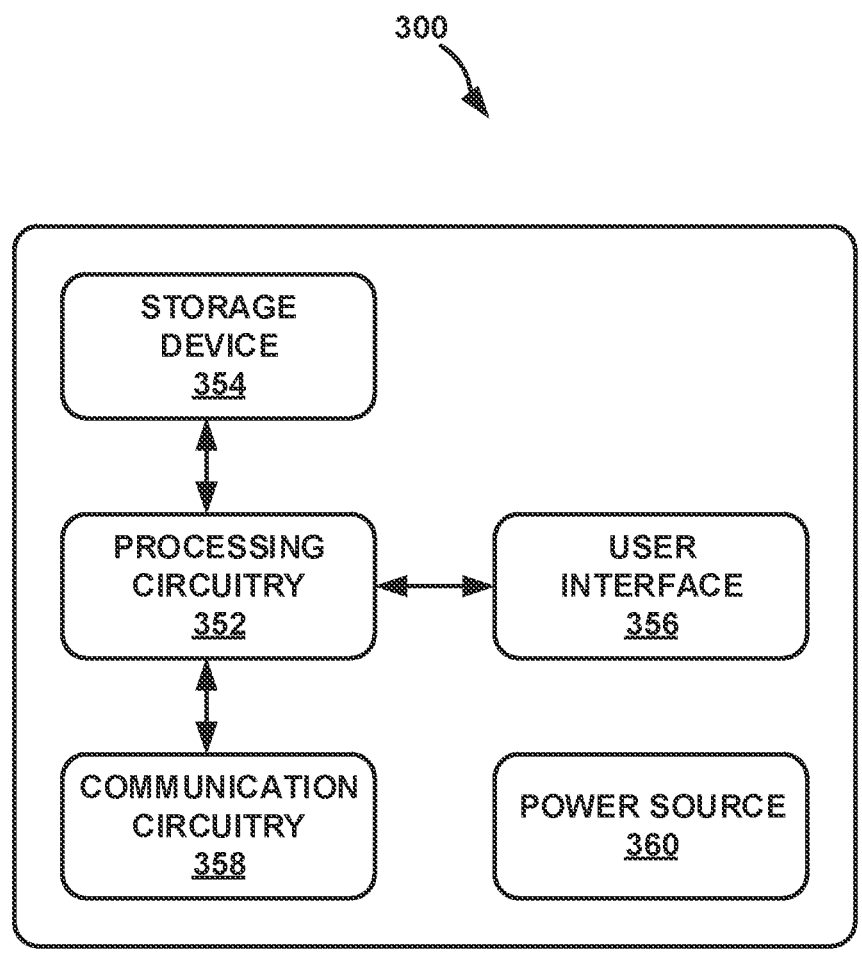
FIG. 3 is a block diagram illustrating an example configuration of components of an external programmer, in accordance with one or more techniques of this disclosure.

FIG. 3 is a block diagram illustrating an example configuration of components of external programmer 300, in accordance with one or more techniques of this disclosure. External programmer 300 may be an example of external programmer 150 of FIG. 1. Although external programmer 300 may generally be described as a hand-held device, external programmer 300 may be a larger portable device or a more stationary device. In addition, in other examples, external programmer 300 may be included as part of an external charging device or include the functionality of an external charging device. As illustrated in FIG. 3, external programmer 300 may include processing circuitry 352, storage device 354, user interface 356, communication circuitry 358, and power source 360. Storage device 354 may store instructions that, when executed by processing circuitry 352, cause processing circuitry 352 and external programmer 300 to provide the functionality ascribed to external programmer 300 throughout this disclosure. Each of these components, circuitry, or modules, may include electrical circuitry that is configured to perform some, or all of the functionality described herein. For example, processing circuitry 352 may include processing circuitry configured to perform the processes discussed with respect to processing circuitry 352.

In general, external programmer 300 includes any suitable arrangement of hardware, alone or in combination with software and/or firmware, to perform the techniques attributed to external programmer 300, and processing circuitry 352, user interface 356, and communication circuitry 358 of external programmer 300. In various examples, external programmer 300 may include one or more processors, such as one or more microprocessors, DSPs, ASICs, FPGAs, or any other equivalent integrated or discrete logic circuitry, as well as any combinations of such components. External programmer 300 also, in various examples, may include a storage device 354, such as RAM, ROM, PROM, EPROM, EEPROM, flash memory, a hard disk, a CD-ROM, including executable instructions for causing the one or more processors to perform the actions attributed to them. Moreover, although processing circuitry 352 and communication circuitry 358 are described as separate modules, in some examples, processing circuitry 352 and communication circuitry 358 are functionally integrated. In some examples, processing circuitry 352 and communication circuitry 358 correspond to individual hardware units, such as ASICs, DSPs, FPGAs, or other hardware units.

Storage device 354 (e.g., a storage device) may store instructions that, when executed by processing circuitry 352, cause processing circuitry 352 and external programmer 300 to provide the functionality ascribed to external programmer 300 throughout this disclosure. For example, storage device 354 may include instructions that cause processing circuitry 352 to obtain a parameter set from memory, select a spatial electrode movement pattern, or receive a user input and send a corresponding command to IMD 200, or instructions for any other functionality. In addition, storage device 354 may include a plurality of programs, where each program includes a parameter set that defines stimulation pulses, such as control pulses and/or informed pulses. Storage device 354 may also store data received from a medical device (e.g., IMD 110). For example, storage device 354 may store ECAP related data recorded at a sensing module of the medical device, and storage device 354 may also store data from one or more sensors of the medical device.

User interface 356 may include a button or keypad, lights, a speaker for voice commands, a display, such as a liquid crystal (LCD), light-emitting diode (LED), or organic light-emitting diode (OLED). In some examples the display includes a touch screen. User interface 356 may be configured to display any information related to the delivery of electrical stimulation, identified patient behaviors, sensed patient parameter values, patient behavior criteria, or any other such information. User interface 356 may also receive user input via user interface 356. The input may be, for example, in the form of pressing a button on a keypad or selecting an icon from a touch screen. The input may request starting or stopping electrical stimulation, the input may request a new spatial electrode movement pattern or a change to an existing spatial electrode movement pattern, of the input may request some other change to the delivery of electrical stimulation. In some examples, user interface 356 may display one or more requests of the patient guidance wizard performed by the system including external programmer 300 and/or IMD 110, and user interface 356 may receive one or more user responses to the one or more requests.

Communication circuitry 358 may support wireless communication between the medical device and external programmer 300 under the control of processing circuitry 352. Communication circuitry 358 may also be configured to communicate with another computing device via wireless communication techniques, or direct communication through a wired connection. In some examples, communication circuitry 358 provides wireless communication via an RF or proximal inductive medium. In some examples, communication circuitry 358 includes an antenna, which may take on a variety of forms, such as an internal or external antenna.

Examples of local wireless communication techniques that may be employed to facilitate communication between external programmer 300 and IMD 110 include RF communication according to the 802.11 or Bluetooth® specification sets or other standard or proprietary telemetry protocols. In this manner, other external devices may be capable of communicating with external programmer 300 without needing to establish a secure wireless connection. As described herein, communication circuitry 358 may be configured to transmit a spatial electrode movement pattern or other stimulation parameter values to IMD 110 for delivery of electrical stimulation therapy.

In some examples, selection of stimulation parameters or therapy stimulation programs are transmitted to the medical device for delivery to a patient (e.g., patient 105 of FIG. 1). In other examples, the therapy may include medication, activities, or other instructions that patient 105 must perform themselves or a caregiver perform for patient 105. In some examples, external programmer 300 provides visual, audible, and/or tactile notifications that indicate there are new instructions. External programmer 300 requires receiving user input acknowledging that the instructions have been completed in some examples.

According to the techniques of the disclosure, user interface 356 of external programmer 300 receives an indication from a clinician instructing a processor of the medical device to update one or more therapy stimulation programs or to update one or more ECAP test stimulation programs. Updating therapy stimulation programs and ECAP test stimulation programs may include changing one or more parameters of the stimulation pulses delivered by the medical device according to the programs, such as amplitude, pulse width, frequency, and pulse shape of the informed pulses and/or control pulses. User interface 356 may also receive instructions from the clinician commanding any electrical stimulation, including control pulses and/or informed pulses to commence or to cease.

Power source 360 is configured to deliver operating power to the components of external programmer 300. Power source 360 may include a battery and a power generation circuit to produce the operating power. In some examples, the battery is rechargeable to allow extended operation. Recharging may be accomplished by electrically coupling power source 360 to a cradle or plug that is connected to an alternating current (AC) outlet. In addition, recharging may be accomplished through proximal inductive interaction between an external charger and an inductive charging coil within external programmer 300. In other examples, traditional batteries (e.g., nickel cadmium or lithium ion batteries) may be used. In addition, external programmer 300 may be directly coupled to an alternating current outlet to operate.

The architecture of external programmer 300 illustrated in FIG. 3 is shown as an example. The techniques as set forth in this disclosure may be implemented in the example external programmer 300 of FIG. 3, as well as other types of systems not described specifically herein. Nothing in this disclosure should be construed so as to limit the techniques of this disclosure to the example architecture illustrated by FIG. 3.

Figure 4:
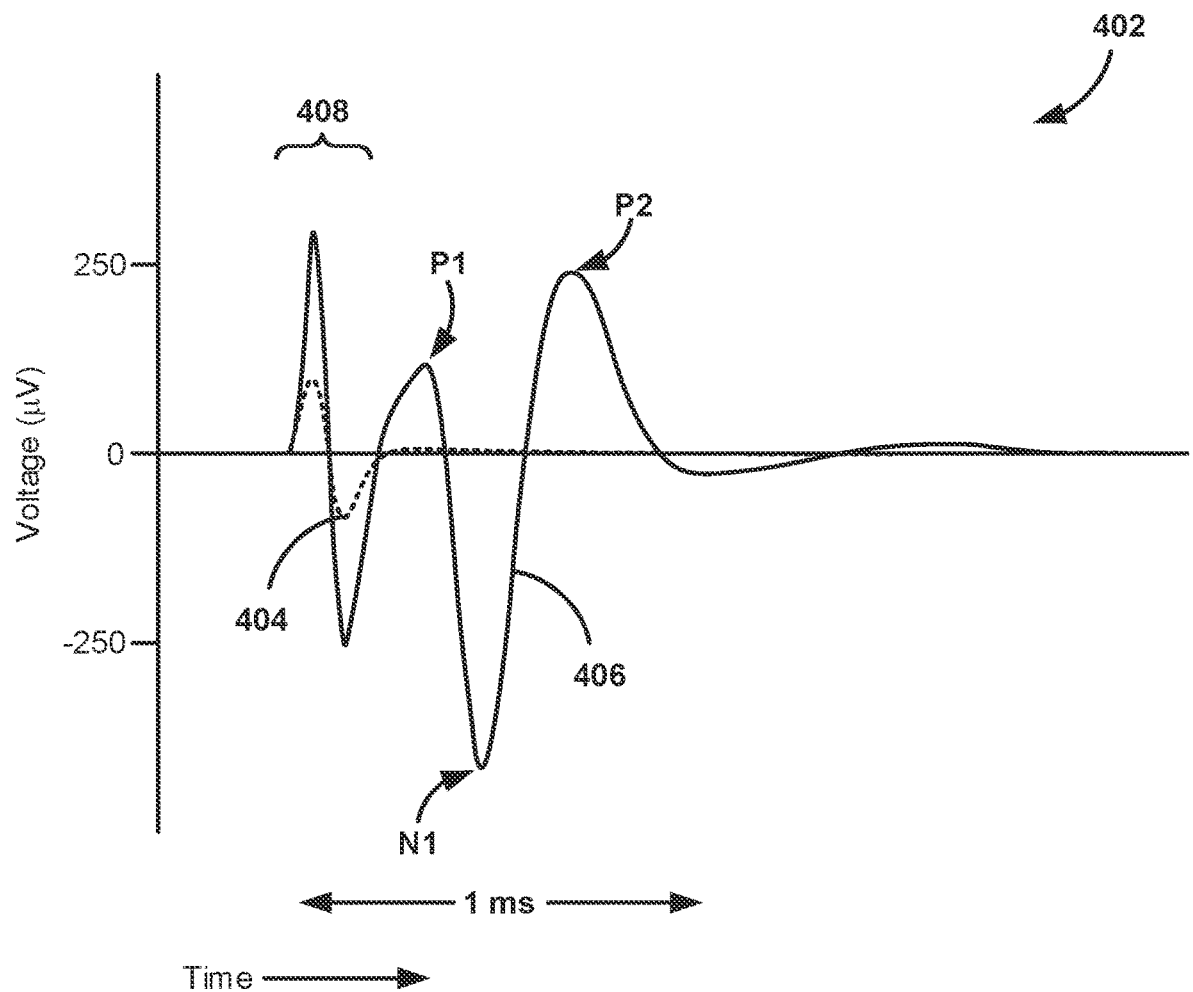
FIG. 4 is a graph of example evoked compound action potentials (ECAPs) sensed for respective stimulation pulses, in accordance with one or more techniques of this disclosure.

FIG. 4 is a graph 402 of example evoked compound action potentials (ECAPs) sensed for respective stimulation pulses, in accordance with one or more techniques of this disclosure. As shown in FIG. 4, graph 402 shows example ECAP signal 404 (dotted line) and ECAP signal 406 (solid line). In some examples, each of ECAP signals 404 and 406 are sensed from control pulses that were delivered from a guarded cathode, where the control pulses are bi-phasic pulses including an interphase interval between each positive and negative phase of the pulse. In some such examples, the guarded cathode includes stimulation electrodes located at the end of an 8-electrode lead (e.g., leads 130 of FIG. 1) while two sensing electrodes are provided at the other end of the 8-electrode lead. ECAP signal 404 illustrates the voltage amplitude sensed as a result from a sub-detection threshold stimulation pulse, or a stimulation pulse which results in no detectable ECAP. Peaks 408 of ECAP signal 404 are detected and represent the artifact of the delivered control pulse. However, no propagating signal is detected after the artifact in ECAP signal 404 because the control pulse was sub-detection stimulation threshold.

In contrast to ECAP signal 404, ECAP signal 406 represents the voltage amplitude detected from a supra-detection stimulation threshold control pulse. Peaks 408 of ECAP signal 406 are detected and represent the artifact of the delivered control pulse. After peaks 408, ECAP signal 406 also includes peaks P1, N1, and P2, which are three typical peaks representative of propagating action potentials from an ECAP. The example duration of the artifact and peaks P1, N1, and P2 is approximately 1 millisecond (ms). When detecting the ECAP of ECAP signal 406, different characteristics may be identified. For example, the characteristic of the ECAP may be the amplitude between N1 and P2. This N1-P2 amplitude may be easily detectable even if the artifact impinges on P1, a relatively large signal, and the N1-P2 amplitude may be minimally affected by electronic drift in the signal. In other examples, the characteristic of the ECAP used to control subsequent control pulses and/or informed pulses may be an amplitude of P1, N1, or P2 with respect to neutral or zero voltage. In some examples, the characteristic of the ECAP used to control subsequent control pulses or informed pulses is a sum of two or more of peaks P1, N1, or P2. In other examples, the characteristic of ECAP signal 406 may be the area under one or more of peaks P1, N1, and/or P2. In other examples, the characteristic of the ECAP may be a ratio of one of peaks P1, N1, or P2 to another one of the peaks. In some examples, the characteristic of the ECAP is a slope between two points in the ECAP signal, such as the slope between N1 and P2. In other examples, the characteristic of the ECAP may be the time between two points of the ECAP, such as the time between N1 and P2. The time between when the stimulation pulse is delivered and a point in the ECAP signal may be referred to as a latency of the ECAP and may indicate the types of fibers being captured by the stimulation pulse (e.g., a control pulse). ECAP signals with lower latency (i.e., smaller latency values) indicate a higher percentage of nerve fibers that have faster propagation of signals, whereas ECAP signals with higher latency (i.e., larger latency values) indicate a higher percentage of nerve fibers that have slower propagation of signals. Latency may also refer to the time between an electrical feature is detected at one electrode and then detected again at a different electrode. This time, or latency, is inversely proportional to the conduction velocity of the nerve fibers. Other characteristics of the ECAP signal may be used in other examples.

The amplitude of the ECAP signal increases with increased amplitude of the control pulse, as long as the pulse amplitude is greater than threshold such that nerves depolarize and propagate the signal. The target ECAP characteristic (e.g., the target ECAP amplitude) may be determined from the ECAP signal detected from a control pulse when informed pulses are determined to deliver effective therapy to patient 105. The ECAP signal thus is representative of the distance between the stimulation electrodes and the nerves appropriate for the stimulation parameter values of the informed pulses delivered at that time. Therefore, IMD 110 may attempt to use detected changes to the measured ECAP characteristic value to change therapy pulse parameter values and maintain the target ECAP characteristic value during therapy pulse delivery.

Figure 5A:
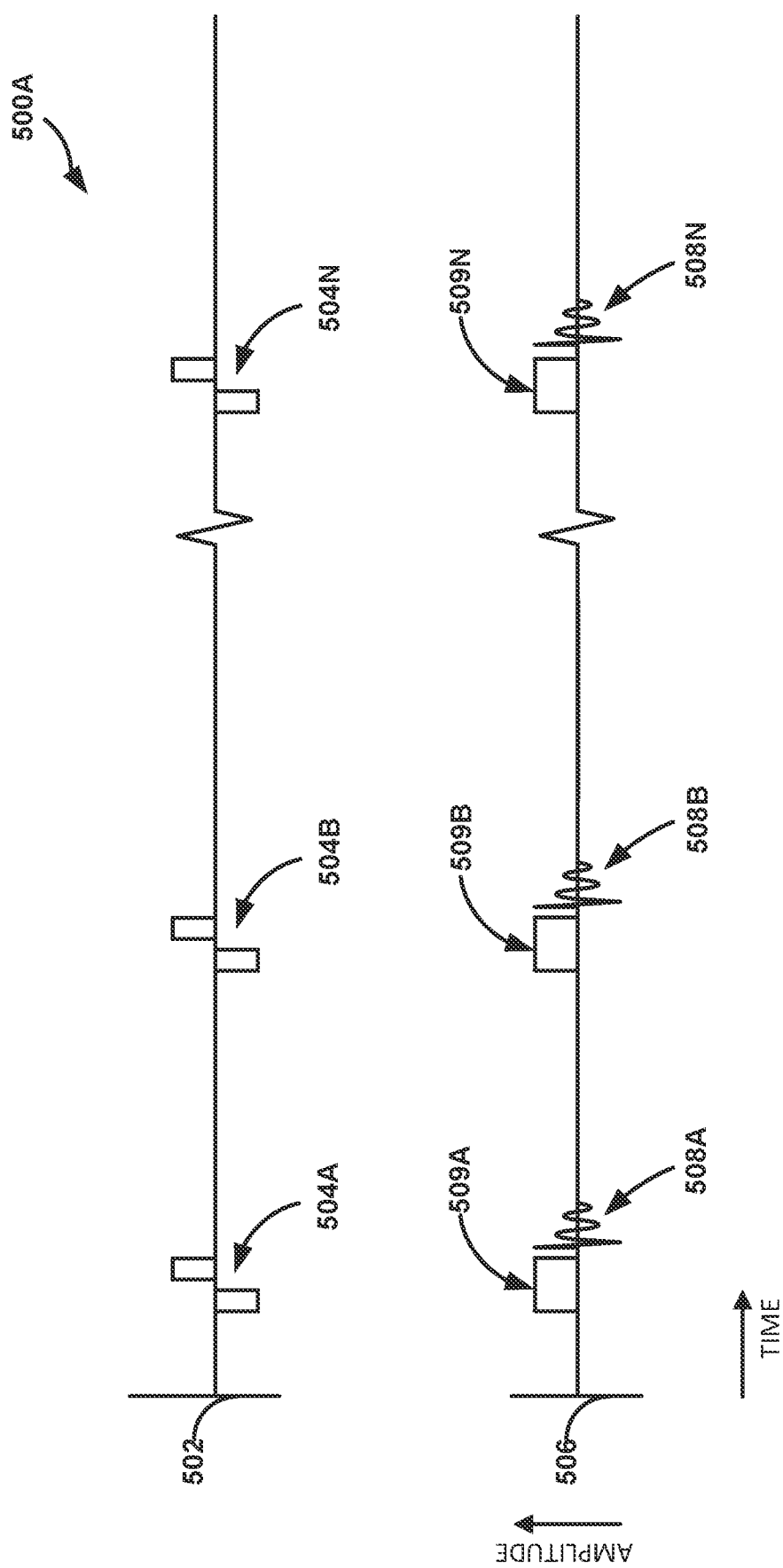
FIG. 5A is a timing diagram illustrating an example of electrical stimulation pulses, respective stimulation signals, and respective sensed ECAPs, in accordance with one or more techniques of this disclosure.

FIG. 5A is a timing diagram 500A illustrating an example of electrical stimulation pulses, respective stimulation signals, and respective sensed ECAPs, in accordance with one or more techniques of this disclosure. For convenience, FIG. 5A is described with reference to IMD 200 of FIG. 2. As illustrated, timing diagram 500A includes first channel 502, a plurality of stimulation pulses 504A-504N (collectively "stimulation pulses 504"), second channel 506, a plurality of respective ECAPs 508A-508N (collectively "ECAPs 508"), and a plurality of stimulation signals 509A-509N (collectively "stimulation signals 509"). In some examples, stimulation pulses 504 may represent control pulses which are configured to elicit ECAPs 508 that are detectible by IMD 200, but this is not required. Stimulation pulses 504 may represent any type of pulse that is deliverable by IMD 200. In the example of FIG. 5A, IMD 200 can deliver therapy with control pulses instead of, or without, informed pulses.

First channel 502 is a time/voltage (and/or current) graph indicating the voltage (or current) of at least one electrode of electrodes 232, 234. In one example, the stimulation electrodes of first channel 502 may be located on the opposite side of the lead as the sensing electrodes of second channel 506. Stimulation pulses 504 may be electrical pulses delivered to the spinal cord of the patient by at least one of electrodes 232, 234, and stimulation pulses 504 may be balanced biphasic square pulses with an interphase interval. In other words, each of stimulation pulses 504 are shown with a negative phase and a positive phase separated by an interphase interval. For example, a stimulation pulse 504 may have a negative voltage for the same amount of time and amplitude that it has a positive voltage. It is noted that the negative voltage phase may be before or after the positive voltage phase. Stimulation pulses 504 may be delivered according to test stimulation programs 216 stored in storage device 212 of IMD 200, and test stimulation programs 216 may be updated according to user input via an external programmer and/or may be updated according to a signal from sensor(s) 222. In one example, stimulation pulses 504 may have a pulse width of less than approximately 300 microseconds (e.g., the total time of the positive phase, the negative phase, and the interphase interval is less than 300 microseconds). In another example, stimulation pulses 504 may have a pulse width of approximately 100 µs for each phase of the bi-phasic pulse. As illustrated in FIG. 5A, stimulation pulses 504 may be delivered via channel 502. Delivery of stimulation pulses 504 may be delivered by leads 230 in a guarded cathode electrode combination. For example, if leads 230 are linear 8-electrode leads, a guarded cathode combination is a central cathodic electrode with anodic electrodes immediately adjacent to the cathodic electrode.

Second channel 506 is a time/voltage (and/or current) graph indicating the voltage (or current) of at least one electrode of electrodes 232, 234. In one example, the electrodes of second channel 506 may be located on the opposite side of the lead as the electrodes of first channel 502. ECAPs 508 may be sensed at electrodes 232, 234 from the spinal cord of the patient in response to stimulation pulses 504. ECAPs 508 are electrical signals which may propagate along a nerve away from the origination of stimulation pulses 504. In one example, ECAPs 508 are sensed by different electrodes than the electrodes used to deliver stimulation pulses 504. As illustrated in FIG. 5A, ECAPs 508 may be recorded on second channel 506.

Stimulation signals 509A, 509B, and 509N may be sensed by leads 230 and sensing circuitry 206 and may be sensed during the same period of time as the delivery of stimulation pulses 504. Since the stimulation signals may have a greater amplitude and intensity than ECAPs 508, any ECAPs arriving at IMD 200 during the occurrence of stimulation signals 509 might not be adequately sensed by sensing circuitry 206 of IMD 200. However, ECAPs 508 may be sufficiently sensed by sensing circuitry 206 because each ECAP 508, or at least a portion of ECAP 508 used as feedback for stimulation pulses 504, falls after the completion of each a stimulation pulse 504. As illustrated in FIG. 5A, stimulation signals 509 and ECAPs 508 may be recorded on channel 506. In some examples, ECAPs 508 may not follow respective stimulation signals 509 when ECAPs are not elicited by stimulation pulses 504 or the amplitude of ECAPs is too low to be detected (e.g., below the detection threshold).

Figure 5B:
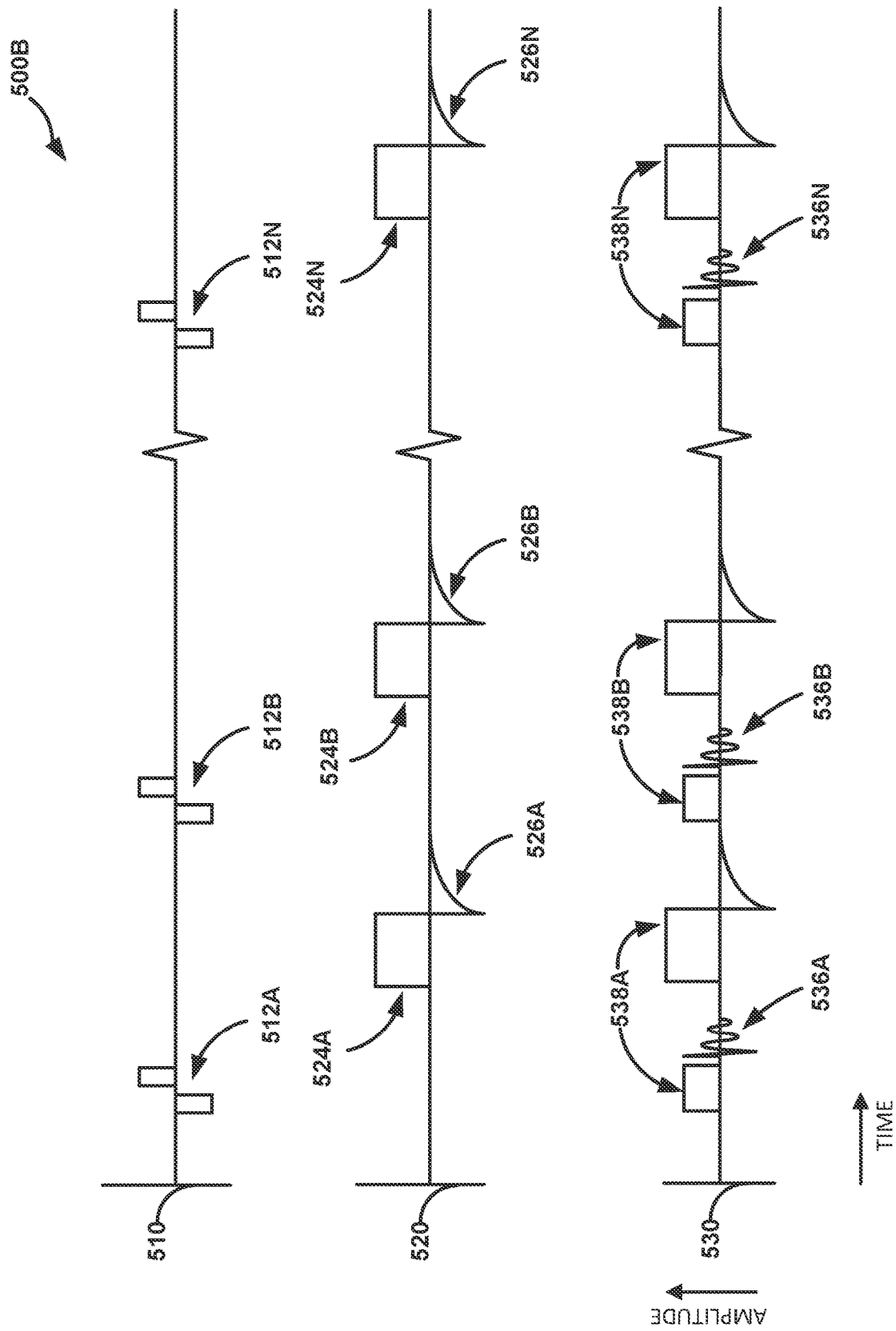
FIG. 5B is a timing diagram illustrating one example of electrical stimulation pulses, respective stimulation signals, and respective sensed ECAPs, in accordance with one or more techniques of this disclosure.

FIG. 5B is a timing diagram 500B illustrating one example of electrical stimulation pulses, respective stimulation signals, and respective sensed ECAPs, in accordance with one or more techniques of this disclosure. For convenience, FIG. 5B is described with reference to IMD 200 of FIG. 2. As illustrated, timing diagram 500B includes first channel 510, a plurality of control pulses 512A-512N (collectively "control pulses 512"), second channel 520, a plurality of informed pulses 524A-524N (collectively "informed pulses 524") including passive recharge phases 526A-526N (collectively "passive recharge phases 526"), third channel 530, a plurality of respective ECAPs 536A-536N (collectively "ECAPs 536"), and a plurality of stimulation signals 538A-538N (collectively "stimulation signals 538").

First channel 510 is a time/voltage (and/or current) graph indicating the voltage (or current) of at least one electrode of electrodes 232, 234. In one example, the stimulation electrodes of first channel 510 may be located on the opposite side of the lead as the sensing electrodes of third channel 530. Control pulses 512 may be electrical pulses delivered to the spinal cord of the patient by at least one of electrodes 232, 234, and control pulses 512 may be balanced biphasic square pulses with an interphase interval. In other words, each of control pulses 512 are shown with a negative phase and a positive phase separated by an interphase interval. For example, a control pulse 512 may have a negative voltage for the same amount of time that it has a positive voltage. It is noted that the negative voltage phase may be before or after the positive voltage phase. Control pulses 512 may be delivered according to test stimulation programs 216 stored in storage device 212 of IMD 200, and test stimulation programs 216 may be updated according to user input via an external programmer and/or may be updated according to a signal from sensor(s) 222. In one example, control pulses 512 may have a pulse width of 300 microseconds (e.g., the total time of the positive phase, the negative phase, and the interphase interval is 300 microseconds). In another example, control pulses 512 may have a pulse width of approximately 100 µs for each phase of the bi-phasic pulse. As illustrated in FIG. 5B, control pulses 512 may be delivered via first channel 510. Delivery of control pulses 512 may be delivered by leads 230 in a guarded cathode electrode combination. For example, if leads 230 are linear 8-electrode leads, a guarded cathode combination is a central cathodic electrode with anodic electrodes immediately adjacent to the cathodic electrode.

Second channel 520 is a time/voltage (and/or current) graph indicating the voltage (or current) of at least one electrode of electrodes 232, 234 for the informed pulses. In one example, the electrodes of second channel 520 may partially or fully share common electrodes with the electrodes of first channel 510 and third channel 530. Informed pulses 524 may also be delivered by the same leads 230 that are configured to deliver control pulses 512. Informed pulses 524 may be interleaved with control pulses 512, such that the two types of pulses are not delivered during overlapping periods of time. However, informed pulses 524 may or may not be delivered by exactly the same electrodes that deliver control pulses 512. Informed pulses 524 may be monophasic pulses with pulse widths of greater than approximately 300 µs and less than approximately 1000 µs. In fact, informed pulses 524 may be configured to have longer pulse widths than control pulses 512. As illustrated in FIG. 5B, informed pulses 524 may be delivered on second channel 520.

Informed pulses 524 may be configured for passive recharge. For example, each informed pulse 524 may be followed by a passive recharge phase 526 to equalize charge on the stimulation electrodes. Unlike a pulse configured for active recharge, where remaining charge on the tissue following a stimulation pulse is instantly removed from the tissue by an opposite applied charge, passive recharge allows tissue to naturally discharge to some reference voltage (e.g., ground or a rail voltage) following the termination of the therapy pulse. In some examples, the electrodes of the medical device may be grounded at the medical device body. In this case, following the termination of informed pulse 524, the charge on the tissue surrounding the electrodes may dissipate to the medical device, creating a rapid decay of the remaining charge at the tissue following the termination of the pulse. This rapid decay is illustrated in passive recharge phases 526. Passive recharge phase 526 may have a duration in addition to the pulse width of the preceding informed pulse 524. In other examples (not pictured in FIG. 5B), informed pulses 524 may be bi-phasic pulses having a positive and negative phase (and, in some examples, an interphase interval between each phase) which may be referred to as pulses including active recharge. An informed pulse that is a bi-phasic pulse may or may not have a following passive recharge phase.

Third channel 530 is a time/voltage (and/or current) graph indicating the voltage (or current) of at least one electrode of electrodes 232, 234. In one example, the electrodes of third channel 530 may be located on the opposite side of the lead as the electrodes of first channel 510. ECAPs 536 may be sensed at electrodes 232, 234 from the spinal cord of the patient in response to control pulses 512. ECAPs 536 are electrical signals which may propagate along a nerve away from the origination of control pulses 512. In one example, ECAPs 536 are sensed by different electrodes than the electrodes used to deliver control pulses 512. As illustrated in FIG. 5B, ECAPs 536 may be recorded on third channel 530.

Stimulation signals 538A, 538B, and 538N may be sensed by leads 230 and may be sensed during the same period of time as the delivery of control pulses 512 and informed pulses 524. Since the stimulation signals may have a greater amplitude and intensity than ECAPs 536, any ECAPs arriving at IMD 200 during the occurrence of stimulation signals 538 may not be adequately sensed by sensing circuitry 206 of IMD 200. However, ECAPs 536 may be sufficiently sensed by sensing circuitry 206 because each ECAP 536 falls after the completion of each a control pulse 512 and before the delivery of the next informed pulse 524. As illustrated in FIG. 5B, stimulation signals 538 and ECAPs 536 may be recorded on channel 530.

Figure 6A:
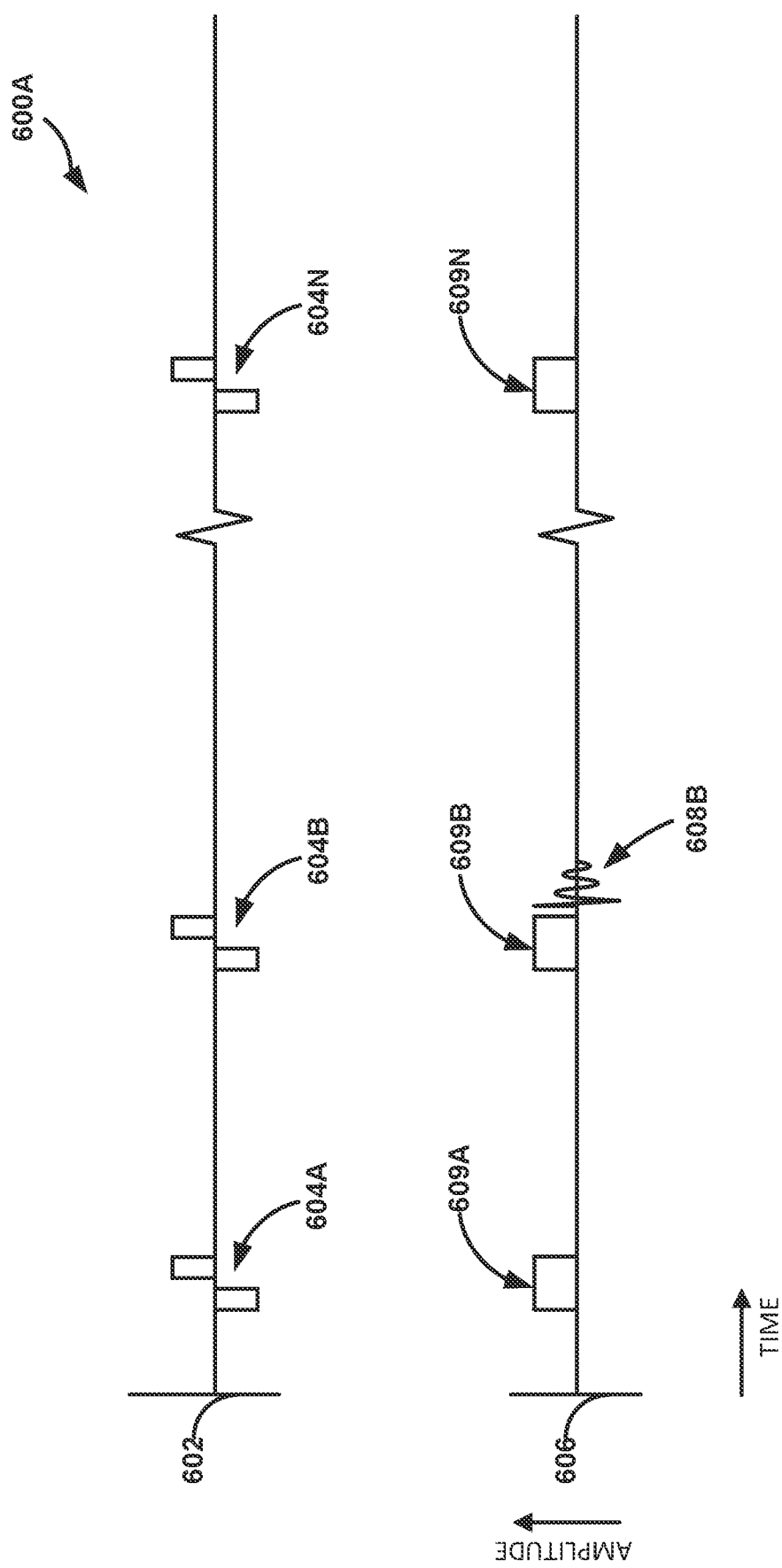
FIG. 6A is a timing diagram illustrating an example of electrical stimulation pulses, respective stimulation signals, and respective sensed ECAPs, in accordance with one or more techniques of this disclosure.

FIG. 6A is a timing diagram 600A illustrating an example of electrical stimulation pulses, respective stimulation signals, and respective sensed ECAPs, in accordance with one or more techniques of this disclosure. For convenience, FIG. 6A is described with reference to IMD 200 of FIG. 2. As illustrated, timing diagram 600A includes first channel 602, a plurality of stimulation pulses 604A-604N (collectively "stimulation pulses 604"), second channel 606, a plurality of respective ECAPs 608A-608N (collectively "ECAPs 608"), and a plurality of stimulation signals 609A-609N (collectively "stimulation signals 609"). In some examples, stimulation pulses 604 may represent control pulses which are configured to elicit ECAPs 608 that are detectible by IMD 200, but this is not required. Stimulation pulses 604 may represent any type of pulse that is deliverable by IMD 200. In the example of FIG. 6A, IMD 200 can deliver therapy with control pulses instead of, or without, informed pulses.

Timing diagram 600A of FIG. 6A may be substantially the same as timing diagram 500A FIG. 5A except that stimulation pulse 604A and stimulation pulse 604N do not evoke an ECAP that is detectible by IMD 200. Although stimulation pulse 604B emits ECAP 608B, which is detectible by IMD 200, it may be the case that IMD 200 does not sense enough detectible ECAPs for therapy determination in the example of FIG. 6A. As such, IMD 200 may determine one or more characteristics of stimulation signals 609 in order to determine one or more parameters of upcoming stimulation pulses following stimulation pulse 604N. For example, IMD 200 may determine an amplitude of at least a portion of each stimulation signal of stimulation signals 609 and determine the one or more parameters of the upcoming stimulation pulses based on the determined amplitudes. Although stimulation signals 609 are illustrated as square pulses, stimulation signals 609 may include other shapes and/or waveforms, in some examples. In some examples, each stimulation signal of stimulation signals 509 may include two or more phases. Processing circuitry 210 of IMD 200 may analyze the two or more phases of stimulation signals 509 in order to determine therapy.

Figure 6B:
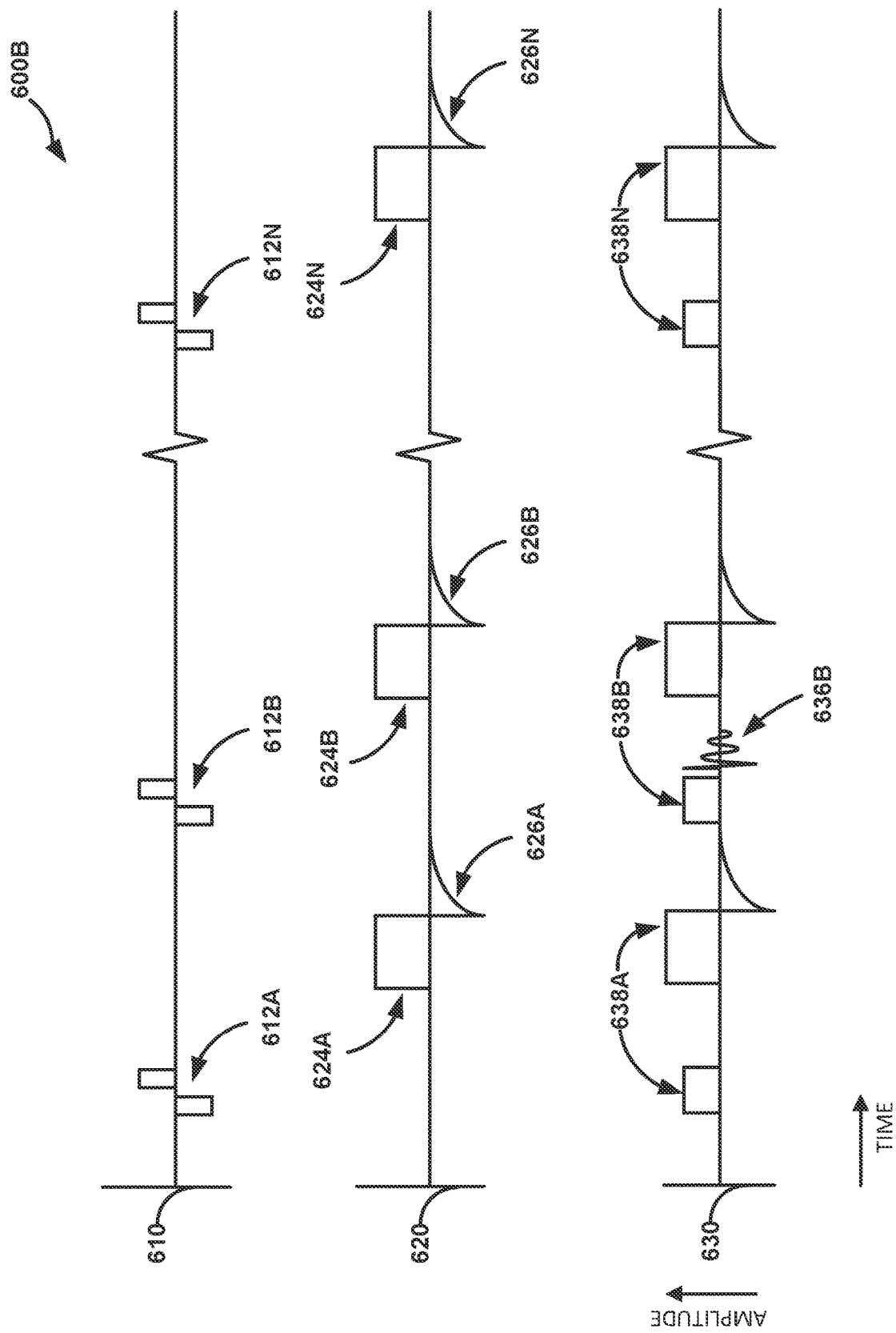
FIG. 6B is a timing diagram illustrating another example of electrical stimulation pulses, respective stimulation signals, and respective sensed ECAPs, in accordance with one or more techniques of this disclosure.

FIG. 6B is a timing diagram 600B illustrating another example of electrical stimulation pulses, respective stimulation signals, and respective sensed ECAPs, in accordance with one or more techniques of this disclosure. For convenience, FIG. 6B is described with reference to IMD 200 of FIG. 2. As illustrated, timing diagram 600B includes first channel 610, a plurality of control pulses 612A-612N (collectively "control pulses 612"), second channel 620, a plurality of informed pulses 624A-624N (collectively "informed pulses 624") including passive recharge phases 626A-626N (collectively "passive recharge phases 626"), third channel 630, a plurality of respective ECAPs 636A-636N (collectively "ECAPs 636"), and a plurality of stimulation signals 638A-638N (collectively "stimulation signals 638").

Timing diagram 600B of FIG. 6B may be substantially the same as timing diagram 500B FIG. 5B except that control pulse 612A and control pulse 612N do not evoke an ECAP that is detectible by IMD 200. Although control pulse 612B emits ECAP 636B, which is detectible by IMD 200, it may be the case that IMD 200 does not sense enough detectible ECAPs for therapy determination in the example of FIG. 6B. As such, IMD 200 may determine one or more characteristics of stimulation signals 638 in order to determine one or more parameters of upcoming stimulation pulses following control pulse 612N. For example, IMD 200 may determine an amplitude of at least a portion of each stimulation signal of stimulation signals 638 and determine the one or more parameters of the upcoming stimulation pulses based on the determined amplitudes. Although stimulation signals 638 are illustrated as square pulses, stimulation signals 639 may include other shapes and/or waveforms, in some examples. In some examples, each stimulation signal of stimulation signals 638 may include two or more phases. Processing circuitry 210 of IMD 200 may analyze the two or more phases of stimulation signals 638 in order to determine therapy.

Figure 7:
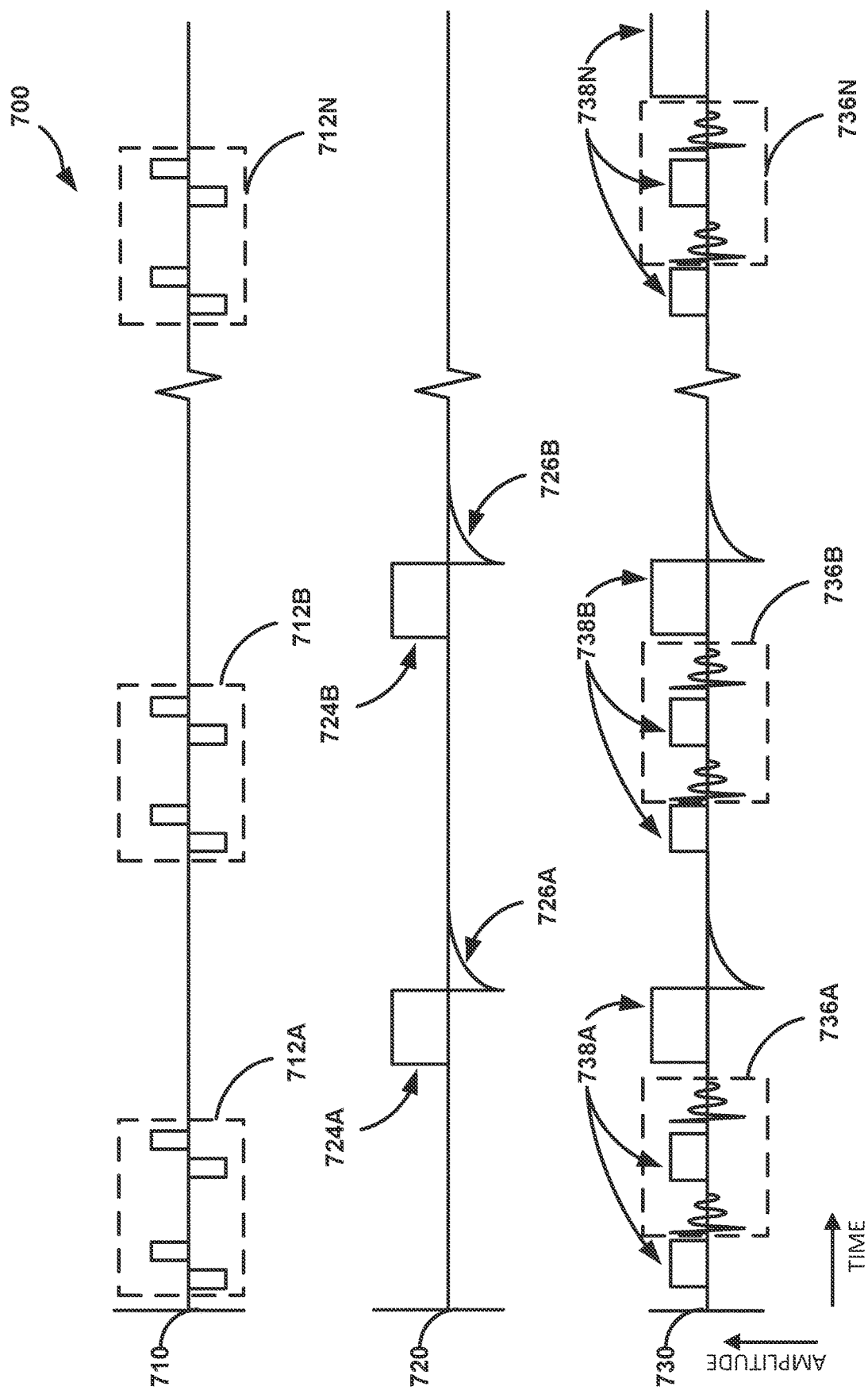
FIG. 7 is a timing diagram illustrating another example of electrical stimulation pulses, respective stimulation signals, and respective ECAPs, in accordance with one or more techniques of this disclosure.

FIG. 7 is a timing diagram 700 illustrating another example of electrical stimulation pulses, respective stimulation signals, and respective ECAPs, in accordance with one or more techniques of this disclosure. For convenience, FIG. 7 is described with reference to IMD 200 of FIG. 2. As illustrated, timing diagram 700 includes first channel 710, a plurality of control pulses 712A-712N (collectively "control pulses 712"), second channel 720, a plurality of informed pulses 724A-724B (collectively "informed pulses 724") including passive recharge phases 726A-726B (collectively "passive recharge phases 726"), third channel 730, a plurality of respective ECAPs 736A-736N (collectively "ECAPs 736"), and a plurality of stimulation interference signals 738A-738N (collectively "stimulation interference signals 738"). FIG. 7 may be substantially similar to FIG. 5B, except for the differences detailed below.

Two or more (e.g. two) control pulses 712 may be delivered during each time event (e.g., window) of a plurality of time events, and each time event represents a time between two consecutive informed pulses 724. For example, during each time event, a first control pulse may be directly followed by a first respective ECAP, and subsequent to the completion of the first respective ECAP, a second control pulse may be directly followed by a second respective ECAP. Informed pulses may commence following the second respective ECAP. In other examples not illustrated here, three or more control pulses 712 may be delivered, and respective ECAP signals sensed, during each time event of the plurality of time events.

Figure 8:
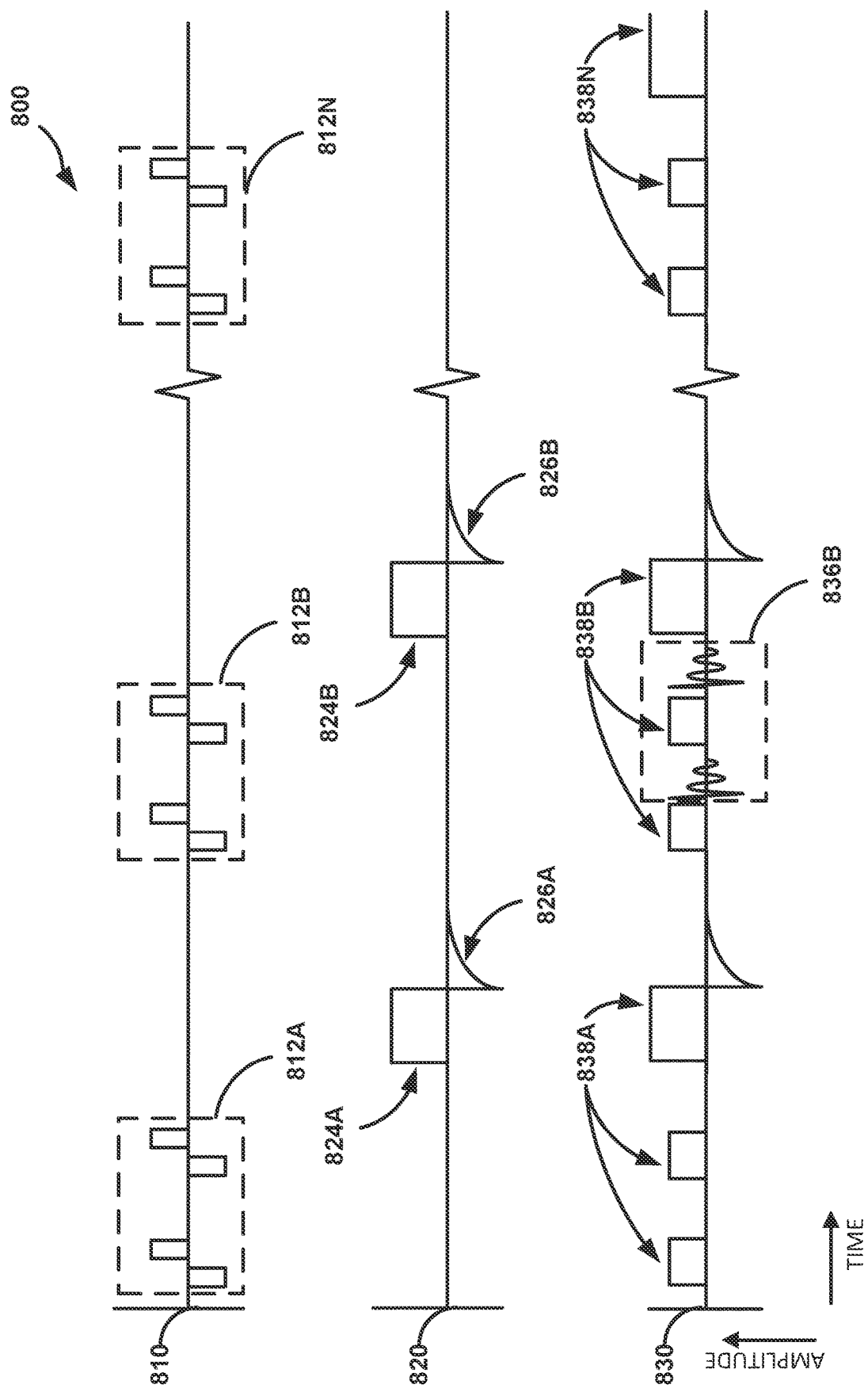
FIG. 8 is a timing diagram illustrating another example of electrical stimulation pulses, respective stimulation signals, and respective ECAPs, in accordance with one or more techniques of this disclosure.

FIG. 8 is a timing diagram 800 illustrating another example of electrical stimulation pulses, respective stimulation signals, and respective ECAPs, in accordance with one or more techniques of this disclosure. For convenience, FIG. 8 is described with reference to IMD 200 of FIG. 2. As illustrated, timing diagram 800 includes first channel 810, a plurality of control pulses 812A-812N (collectively "control pulses 812"), second channel 820, a plurality of informed pulses 824A-824B (collectively "informed pulses 824") including passive recharge phases 826A-826B (collectively "passive recharge phases 826"), third channel 830, respective ECAPs 836B (collectively "ECAPs 836"), and a plurality of stimulation interference signals 838A-838N (collectively "stimulation interference signals 838"). Timing diagram 800 of FIG. 8 may be substantially the same as timing diagram 700 FIG. 7 except that control pulses 812A and control pulses 812N do not evoke ECAPs that are detectible by IMD 200. Although control pulses 812B emit ECAPs 836B, which are detectible by IMD 200, it may be the case that IMD 200 does not sense enough detectible ECAPs for therapy determination in the example of FIG. 8. As such, IMD 200 may determine one or more characteristics of stimulation signals 838 in order to determine one or more parameters of upcoming stimulation pulses following control pulses 812N.

Figure 9:
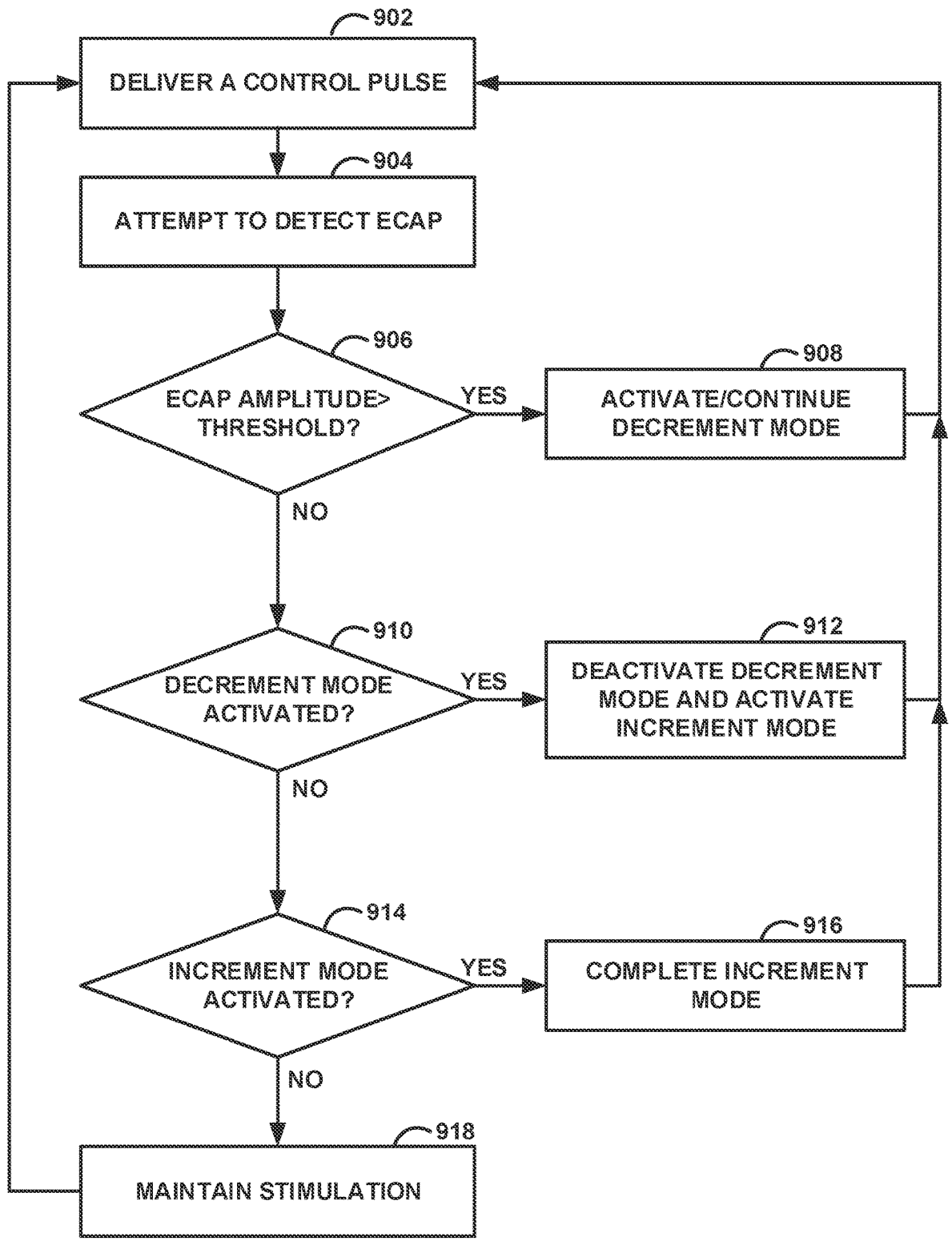
FIG. 9 is a flow diagram illustrating an example operation for controlling stimulation based on one or more sensed ECAPs, in accordance with one or more techniques of this disclosure.

FIG. 9 is a flow diagram illustrating an example operation for controlling stimulation based on one or more sensed ECAPs, in accordance with one or more techniques of this disclosure. For convenience, FIG. 9 is described with respect to IMD 200 of FIG. 2. However, the techniques of FIG. 9 may be performed by different components of IMD 200 or by additional or alternative medical devices.

Stimulation generation circuitry 202 of IMD 200 may deliver electrical stimulation therapy to a patient (e.g., patient 105). In order to control the electrical stimulation therapy, processing circuitry 210 may direct the delivery of at least some stimulation pulses according to therapy stimulation programs 214 of storage device 212, where the electrical stimulation therapy may include a plurality of control pulses and/or informed pulses. Informed pulses may, in some cases, produce ECAPs detectable by IMD 200. However, in other cases, an electrical polarization of an informed pulse may interfere with sensing of an ECAP responsive to the informed pulse. In some examples, to evoke ECAPs which are detectable by IMD 200, stimulation generation circuitry 202 delivers a plurality of control pulses, the plurality of control pulses being interleaved with at least some informed pulses of the plurality of informed pulses. Processing circuitry 210 may control the delivery of control pulses according to ECAP test stimulation programs 216. Since the control pulses may be interleaved with the informed pulses, sensing circuitry 206 of IMD 200 may detect a plurality of ECAPs, where sensing circuitry 206 is configured to detect each ECAP of the plurality of ECAPs after a control pulse of the plurality of control pulses and prior to a subsequent informed pulse of the plurality of informed pulses. In this way, IMD 200 may evoke the plurality of ECAPs in target tissue by delivering control pulses without the informed pulses obstructing IMD 200 from sensing the ECAPs.

As illustrated in FIG. 9, processing circuitry 210 directs stimulation generation circuitry 202 to deliver a control pulse (902). Stimulation generation circuitry 202 may deliver the control pulse to target tissue of patient 105 via any combination of electrodes 232, 234 of leads 230. In some examples, the control pulse may include a balanced, bi-phasic square pulse that employs an active recharge phase. However, in other examples, the control pulse may include a monophasic pulse followed by a passive recharge phase. In other examples, the control pulse may include an imbalanced bi-phasic portion and a passive recharge portion. Although not necessary, a bi-phasic control pulse may include an interphase interval between the positive and negative phase to promote propagation of the nerve impulse in response to the first phase of the bi-phasic pulse. The control pulse may have a pulse width of 300 μs, such as a bi-phasic pulse with each phase having a duration of approximately 100 μs.

After delivering the control pulse, IMD 200 attempts to detect an ECAP (904). For example, sensing circuitry 206 may monitor signals from any combination of electrodes 232, 234 of leads 230. In some examples, sensing circuitry 206 detects ECAPs from a particular combination of electrodes 232, 234. In some cases, the particular combination of electrodes for sensing ECAPs includes different electrodes than a set of electrodes 232, 234 used to deliver stimulation pulses. Alternatively, in other cases, the particular combination of electrodes used for sensing ECAPs includes at least one of the same electrodes as a set of electrodes used to deliver stimulation pulses to patient 105. In some examples, the particular combination of electrodes used for sensing ECAPs may be located on an opposite side of leads 230 from the particular combination of electrodes used to deliver stimulation pulses. IMD 200 may detect an ECAP responsive to the control pulse. IMD 200 may measure one or more characteristics of the responsive ECAP, such as ECAP amplitude, ECAP duration, peak-to-peak durations, or any combination thereof. For example, to measure an amplitude of the ECAP, IMD 200 may determine a voltage difference between an N1 ECAP peak and a P2 ECAP peak.

At block 906, processing circuitry 210 determines if the ECAP amplitude of the responsive ECAP is greater than an ECAP amplitude threshold. If the ECAP amplitude is greater than the ECAP amplitude threshold ("YES" branch of block 906), processing circuitry 210 activates/continues a decrement mode (908) in IMD 200. For example, if the decrement mode is already "turned on" in IMD 200 when processing circuitry determines that the ECAP amplitude is greater than the ECAP amplitude threshold, then processing circuitry 210 maintains IMD 200 in the decrement mode. If the decrement mode is "turned off" in IMD 200 when processing circuitry determines that the ECAP amplitude is greater than the ECAP amplitude threshold, then processing circuitry 210 activates the decrement mode. In some examples, the decrement mode may be stored in storage device 212 as a part of control policy 213. The decrement mode may be a set of instructions which causes IMD 200 to decrease one or more parameter values of each consecutive informed pulse from a respective predetermined value (e.g., a value determined by a stimulation program) and decrease one or more parameter values of each consecutive control pulse from a respective predetermined value (e.g., a value determined by a stimulation program). In other words, the parameter values may be reduced from the values that IMD 200 would use to define respective pulses in the absence of the ECAP amplitude exceeding the threshold ECAP amplitude. For example, when the decrement mode is activated, processing circuitry 210 may decrease an electric current amplitude of each consecutive informed pulse delivered by IMD 200 and decrease an electric current amplitude of each consecutive control pulse delivered by IMD 200. After processing circuitry 210 activates/continues the decrement mode, the example operation may return to block 902 and IMD 200 may deliver another control pulse.

If the ECAP amplitude is not greater than the ECAP amplitude threshold ("NO" branch of block 906), processing circuitry 210 determines whether the decrement mode is activated in IMD 200 (910). If the decrement mode is activated in IMD 200 ("YES" branch of block 910), processing circuitry 210 deactivates the decrement mode and activates an increment mode (912) in IMD 200. In some examples, the increment mode may be stored in storage device 212 as a part of control policy 213. The increment mode may be a set of instructions which causes IMD 200 to increase one or more parameter values of each consecutive informed pulse and increase one or more parameter values of each consecutive control pulse. For example, when the increment mode is activated, processing circuitry 210 may increase an electric current amplitude of each consecutive informed pulse delivered by IMD 200 and increase an electric current amplitude of each consecutive control pulse delivered by IMD 200. After processing circuitry 210 deactivates the decrement mode and activates the increment mode, the example operation may return to block 902 and IMD 200 may deliver another control pulse.

When the example operation of FIG. 9 arrives at block 910 and the decrement mode is not activated in IMD 200 ("NO" branch of block 910), processing circuitry 210 determines whether the increment mode is activated (914) in IMD 200. If the increment mode is activated in IMD 200 ("YES" branch of block 914), processing circuitry 210 may complete the increment mode (916) in IMD 200. In some examples, to complete the increment mode, processing circuitry 210 may increase the electric current amplitude of each consecutive informed pulse delivered by IMD 200 and increase the electric current amplitude of each consecutive control pulse delivered by IMD 200 until the pulse amplitude of the stimulation pulses reach an electric current amplitude (e.g., a predetermined value that may be set by the stimulation program selected for therapy) of the stimulation pulses delivered by IMD 200 prior to the activation of the decrement mode. In this manner, the process may not be referred to as a fully closed-loop system. Put another way, IMD 200 may monitor the high end (ECAP amplitude threshold) for adjusting stimulation pulses instead of monitoring any low end of the sensed ECAP amplitude. For example, IMD 200 may continue to increase the current amplitude of consecutive informed pulses without any feedback from the sensed ECAP, unless the sensed ECAP value again exceeds the ECAP amplitude threshold. After processing circuitry 210 completes the increment mode, the example operation may return to block 902 and IMD 200 may deliver another control pulse. When the example operation of FIG. 9 arrives at block 914 and the increment mode is not activated in IMD 200 ("NO" branch of block 914), processing circuitry 210 maintains stimulation (918) in IMD 200. Although FIG. 9 describes adjusting both informed pulses and control pulses, the technique of FIG. 9 may also apply when IMD 200 is delivering only control pulses (e.g., without informed pulses) to the patient for therapy.

Figure 10:
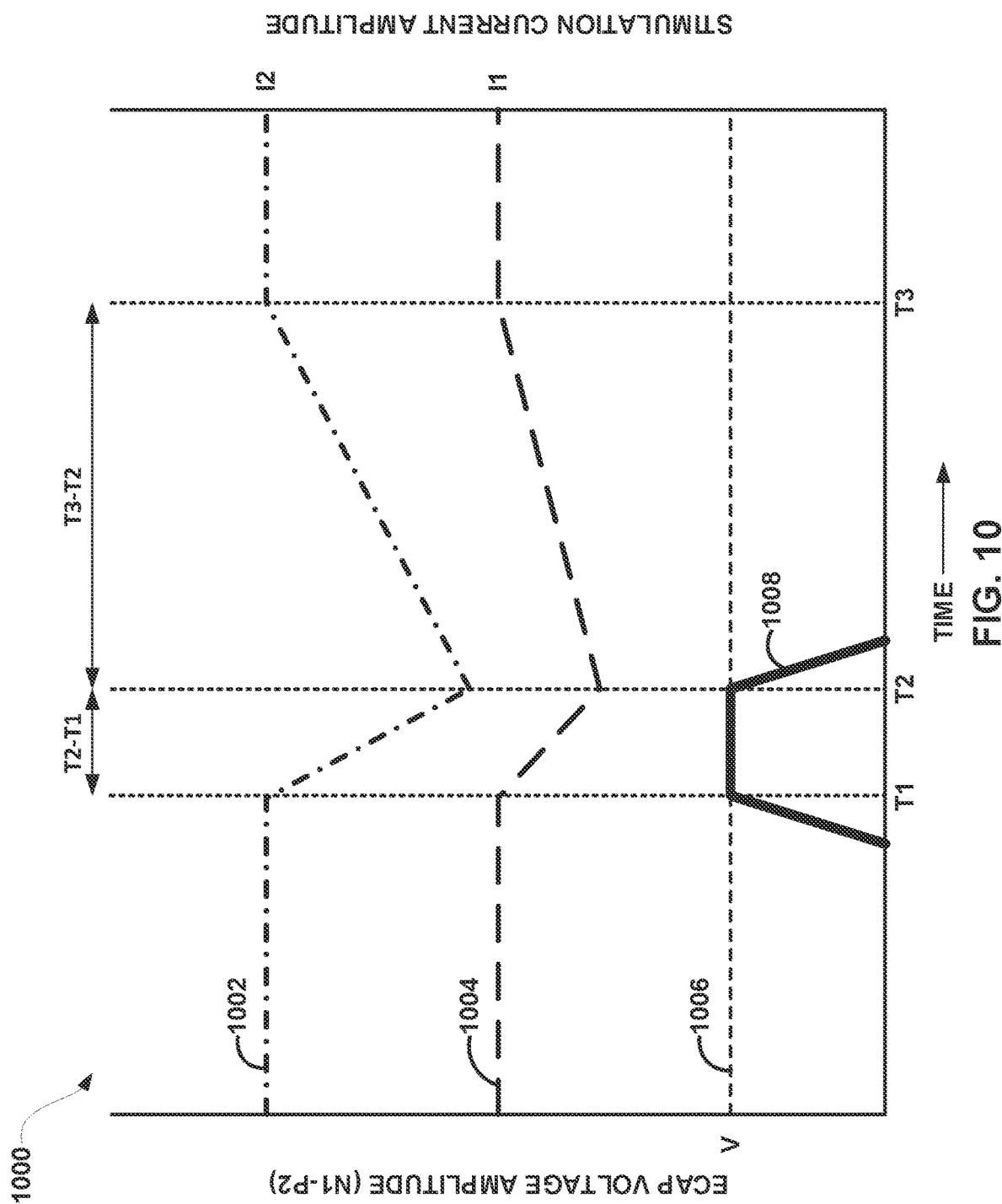
FIG. 10 illustrates a voltage/current/time graph which plots control pulse current amplitude, informed pulse current amplitude, ECAP voltage amplitude, and second ECAP voltage amplitude as a function of time, in accordance with one or more techniques of this disclosure.

FIG. 10 illustrates a voltage/current/time graph 1000 which plots control pulse current amplitude 1002, informed pulse current amplitude 1004, ECAP voltage amplitude 1008, and second ECAP voltage amplitude 1010 as a function of time, in accordance with one or more techniques of this disclosure. Additionally, FIG. 10 illustrates a threshold ECAP amplitude 1006. For convenience, FIG. 10 is described with respect to IMD 200 of FIG. 2. However, the techniques of FIG. 10 may be performed by different components of IMD 200 or by additional or alternative medical devices.

Voltage/current/time graph 1000 illustrates a relationship between sensed ECAP voltage amplitude and stimulation current amplitude. For example, control pulse current amplitude 1002 and informed pulse current amplitude 1004 are plotted alongside ECAP voltage amplitude 1008 as a function of time, thus showing how stimulation current amplitude changes relative to ECAP voltage amplitude. In some examples, IMD 200 delivers a plurality of control pulses and a plurality of informed pulses at control pulse current amplitude 1002 and informed pulse current amplitude 1004, respectively. Initially, IMD 200 may deliver a first set of control pulses, where IMD 200 delivers the first set of control pulses at current amplitude I2. Additionally, IMD 200 may deliver a first set of informed pulses, where IMD 200 delivers the first set of control pulses at current amplitude I1. I1 and I2 may be referred to as a predetermined value for the amplitude of respective control and informed pulses. This predetermined value may be a programmed value or otherwise selected value that a stimulation program has selected to at least partially define stimulation pulses to the patient in the absence of transient conditions (e.g., when the ECAP amplitude is below a threshold ECAP value). The first set of control pulses and the first set of informed pulses may be delivered prior to time T1. In some examples, I1 is 4 milliamps (mA) and I2 is 8 mA. Although control pulse current amplitude 1002 is shown as greater than informed pulse current amplitude 1004, control pulse current amplitude 1002 may be less than or the same as informed pulse current amplitude 1004 in other examples.

While delivering the first set of control pulses and the first set of informed pulses, IMD 200 may record ECAP voltage amplitude 1008. During dynamic and transient conditions which occur in patient 105 such as coughing, sneezing, laughing, Valsalva maneuvers, leg lifting, cervical motions, or deep breathing, ECAP voltage amplitude 1008 may increase if control pulse current amplitude 1002 and informed pulse current amplitude 1004 are held constant. This increase in ECAP voltage amplitude 1008 may be caused by a reduction in the distance between the electrodes and nerves. For example, as illustrated in FIG. 10, ECAP voltage amplitude 1008 may increase prior to time T1 while stimulation current amplitude is held constant. An increasing ECAP voltage amplitude 1008 may indicate that patient 105 is at risk of experiencing transient overstimulation due to the control pulses and the informed pulses delivered by IMD 200. To prevent patient 105 from experiencing transient overstimulation, IMD 200 may decrease control pulse current amplitude 1002 and informed pulse current amplitude 1004 in response to ECAP voltage amplitude 1008 exceeding the threshold ECAP amplitude 1006. For example, if IMD 200 senses an ECAP having an ECAP voltage amplitude 1008 meeting or exceeding threshold ECAP amplitude 1006, as illustrated in FIG. 10 at time T1, IMD 200 may enter a decrement mode where control pulse current amplitude 1002 and informed pulse current amplitude 1004 are decreased. In some examples, the threshold ECAP amplitude 1006 is selected from a range of approximately 5 microvolts (μV) to approximately 30 μV, or from a range of approximately 10 microvolts (μV) to approximately 20 μV. For example, the threshold ECAP amplitude 1006 is 15 μV. In other examples, the threshold ECAP amplitude 1006 is less than or equal to 5 μV or greater than or equal to 30 μV.

IMD 200 may respond relatively quickly to the ECAP voltage amplitude 1008 exceeding the threshold ECAP amplitude 1006. For example, IMD may be configured to detect threshold exceeding ECAP amplitudes within 20 milliseconds (ms). If IMD 200 delivers control pulses at a frequency of 50 Hz, the period of time for a single sample that includes delivering the control pulse and detecting the resulting ECAP signal may be 20 ms or less. However, since an ECAP signal may occur within one or two ms of delivery of the control pulse, IMD 200 may be configured to detect an ECAP signal exceeding the threshold ECAP amplitude in less than 10 ms. For transient conditions, such as a patient coughing or sneezing, these sampling periods would be sufficient to identify ECAP amplitudes exceeding the threshold and a responsive reduction in subsequent pulse amplitudes before the ECAP amplitude would have reached higher levels that may have been uncomfortable for the patient.

The decrement mode may, in some cases, be stored in storage device 212 of IMD 200 as a part of control policy 213. In the example illustrated in FIG. 10, the decrement mode is executed by IMD 200 over a second set of control pulses and a second set of informed pulses which occur between time T1 and time T2. In some examples, to execute the decrement mode, IMD 200 decreases the control pulse current amplitude 1002 of each control pulse of the second set of control pulses according to a first function with respect to time. In other words, IMD 200 decreases each consecutive control pulse of the second set of control pulses proportionally to an amount of time elapsed since a previous control pulse. Additionally, during the decrement mode, IMD 200 may decrease the informed pulse current amplitude 1004 of each informed pulse of the second set of informed pulses according to a second function with respect to time. Although linear first and second functions are shown, the first and/or second function may be non-linear, such as logarithmic (e.g., the rate of change decreases over time), exponential (e.g., the rate of change increases over time), parabolic, step-wise, multiple different functions, etc., in other examples. During a period of time in which IMD 200 is operating in the decrement mode (e.g., time interval T2-T1), ECAP voltage amplitude 1008 of ECAPs sensed by IMD 200 may be greater than or equal to threshold ECAP amplitude 1006.

In the example illustrated in FIG. 2, IMD 200 may sense an ECAP at time T2, where the ECAP has an ECAP voltage amplitude 1008 that is less than threshold ECAP amplitude 1006. The ECAP sensed at time T2 may, in some cases, be the first ECAP sensed by IMD 200 with a below-threshold amplitude since IMD 200 began the decrement mode at time T1. Based on sensing the ECAP at time T2, IMD 200 may deactivate the decrement mode and activate an increment mode. The increment mode may, in some cases, be stored in storage device 212 of IMD 200 as a part of control policy 213. IMD 200 may execute the increment mode over a third set of control pulses and a third set of informed pulses which occur between time T2 and time T3. In some examples, to execute the increment mode, IMD 200 increases the control pulse current amplitude 1002 of each control pulse of the third set of control pulses according to a third function with respect to time. In other words, IMD 200 increases each consecutive control pulse of the third set of control pulses proportionally to an amount of time elapsed since a previous control pulse. Additionally, during the increment mode, IMD 200 may increase the informed pulse current amplitude 1004 of each informed pulse of the third set of informed pulses according to a fourth function with respect to time.

As shown in FIG. 10, IMD 200 is configured to decrease amplitude at a faster rate than increasing amplitude after ECAP voltage amplitude 1008 falls below threshold ECAP amplitude 1006. In other examples, the rate of change during the decrement mode and increment mode may be similar. In other examples, IMD 200 may be configured to increase amplitude of informed and control pulses at a faster rate than when decreasing amplitude. The rate of change in amplitude of the pulses may be relatively instantaneously (e.g., a very fast rate) in other examples. For example, in response to ECAP voltage amplitude 1008 exceeding threshold ECAP amplitude 1006, IMD 200 may immediately drop the amplitude of one or both of control pulse current amplitude 1002 or informed pulse current amplitude 1004 to a predetermined or calculated value. Then, in response to ECAP voltage amplitude 1008 dropping back below threshold ECAP amplitude 1006, IMD 200 may enter increment mode as described above.

When control pulse current amplitude 1002 and informed pulse current amplitude 1004 return to current amplitude I2 and current amplitude I1, respectively, IMD 200 may deactivate the increment mode and deliver stimulation pulses at constant current amplitudes. By decreasing stimulation in response to ECAP amplitudes exceeding a threshold and subsequently increasing stimulation in response to ECAP amplitudes falling below the threshold, IMD 200 may prevent patient 105 from experiencing transient overstimulation or decrease a severity of transient overstimulation experienced by patient 105, whether the decrease is in terms of the length of the experience, the relative intensity, or both.

FIG. 10 is described in the situation in which IMD 200 delivers both control pulse and informed pulses. However, IMD 200 may apply the technique of FIG. 10 to the situation in which only control pulses are delivered to provide therapy to the patient. In this manner, IMD 200 would similarly enter a decrement mode or increment mode for control pulse current amplitude 1002 based on the detected ECAP voltage amplitude 1008 without adjusting the amplitude or other parameter of any other type of stimulation pulse.

Figure 11:
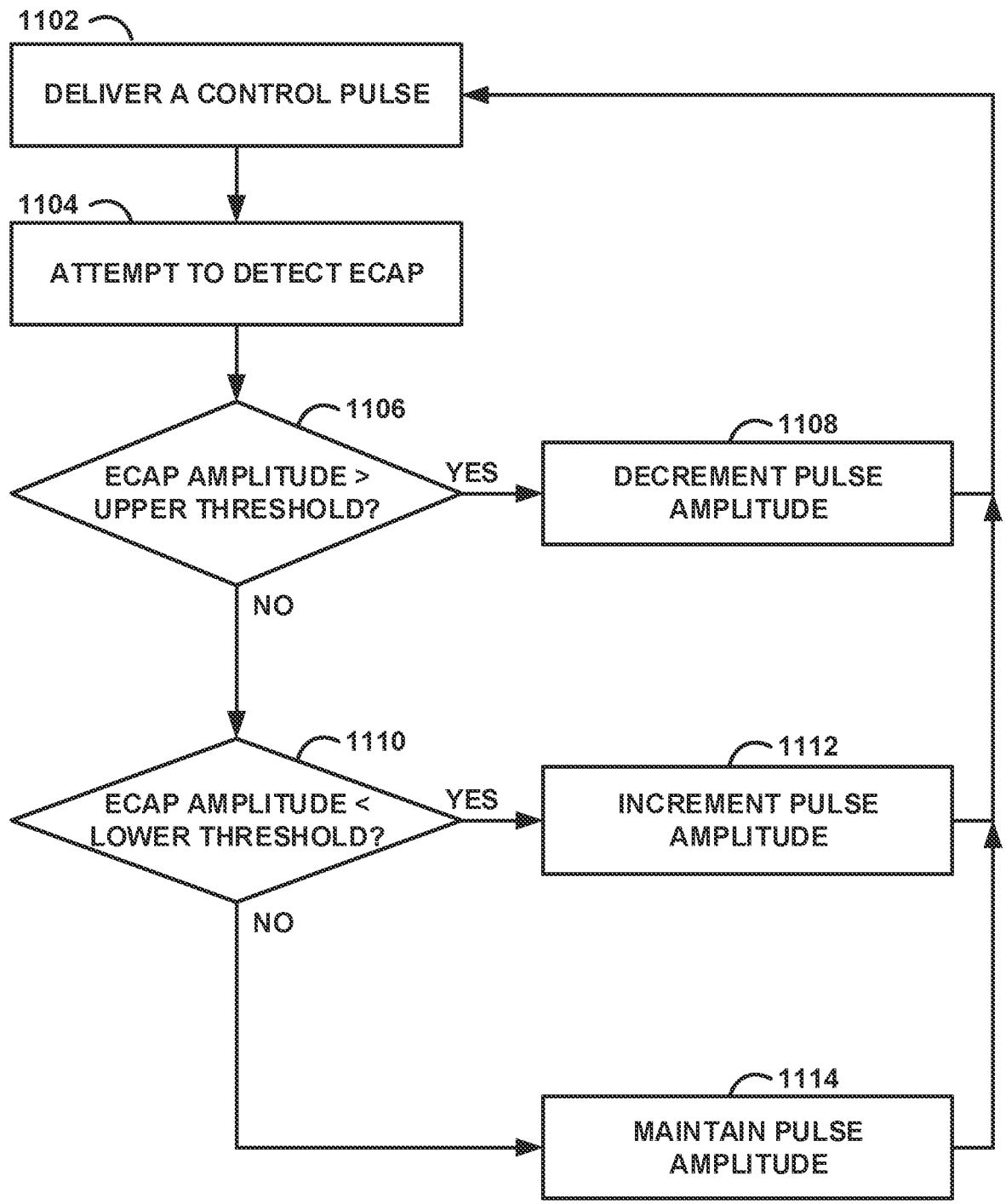
FIG. 11 is a flow diagram illustrating an example operation for controlling stimulation based on one or more sensed ECAPs, in accordance with one or more techniques of this disclosure.

FIG. 11 is a flow diagram illustrating an example operation for controlling stimulation based on one or more sensed ECAPs, in accordance with one or more techniques of this disclosure. FIG. 11 is similar to FIG. 9 above, except that FIG. 11 employs a buffer defined by an upper threshold and a lower threshold that define when amplitude values are increased or decreased. For convenience, FIG. 11 is described with respect to IMD 200 of FIG. 2. However, the techniques of FIG. 11 may be performed by different components of IMD 200 or by additional or alternative medical devices.

Stimulation generation circuitry 202 of IMD 200 may deliver electrical stimulation therapy to a patient (e.g., patient 105). In order to control the electrical stimulation therapy, processing circuitry 210 may direct the delivery of at least some stimulation pulses according to therapy stimulation programs 214 of storage device 212, where the electrical stimulation therapy may include a plurality of control pulses and/or informed pulses. Informed pulses may, in some cases, produce ECAPs detectable by IMD 200. However, in other cases, an electrical polarization of an informed pulse may interfere with sensing of an ECAP responsive to the informed pulse. In some examples, to evoke ECAPs which are detectable by IMD 200, stimulation generation circuitry 202 delivers a plurality of control pulses, the plurality of control pulses being interleaved with at least some informed pulses of the plurality of informed pulses. Processing circuitry 210 may control the delivery of control pulses according to ECAP test stimulation programs 216. Since the control pulses may be interleaved with the informed pulses, sensing circuitry 206 of IMD 200 may detect a plurality of ECAPs, where sensing circuitry 206 is configured to detect each ECAP of the plurality of ECAPs after a control pulse of the plurality of control pulses and prior to a subsequent informed pulse of the plurality of informed pulses. In this way, IMD 200 may evoke the plurality of ECAPs in target tissue by delivering control pulses without the informed pulses obstructing IMD 200 from sensing the ECAPs.

As illustrated in FIG. 11, processing circuitry 210 directs stimulation generation circuitry 202 to deliver a control pulse (1102). Stimulation generation circuitry 202 may deliver the control pulse to target tissue of patient 105 via any combination of electrodes 232, 234 of leads 230. In some examples, the control pulse may include a balanced, bi-phasic square pulse that employs an active recharge phase. However, in other examples, the control pulse may include a monophasic pulse followed by a passive recharge phase. In other examples, the control pulse may include an imbalanced bi-phasic portion and a passive recharge portion. Although not necessary, a bi-phasic control pulse may include an interphase interval between the positive and negative phase to promote propagation of the nerve impulse in response to the first phase of the bi-phasic pulse. The control pulse may have a pulse width of approximately 300 µs, such as a bi-phasic pulse with each phase having a duration of approximately 100 µs.

After delivering the control pulse, IMD 200 attempts to detect an ECAP (1104). For example, sensing circuitry 206 may monitor signals from any combination of electrodes 232, 234 of leads 230. In some examples, sensing circuitry 206 detects ECAPs from a particular combination of electrodes 232, 234. In some cases, the particular combination of electrodes for sensing ECAPs includes different electrodes than a set of electrodes 232, 234 used to deliver stimulation pulses. Alternatively, in other cases, the particular combination of electrodes used for sensing ECAPs includes at least one of the same electrodes as a set of electrodes used to deliver stimulation pulses to patient 105. In some examples, the particular combination of electrodes used for sensing ECAPs may be located on an opposite side of leads 230 from the particular combination of electrodes used to deliver stimulation pulses. IMD 200 may detect an ECAP responsive to the control pulse. IMD 200 may measure one or more characteristics of the responsive ECAP, such as ECAP amplitude, ECAP duration, peak-to-peak durations, or any combination thereof. For example, to measure an amplitude of the ECAP, IMD 200 may determine a voltage difference between an N1 ECAP peak and a P2 ECAP peak.

At block 1106, processing circuitry 210 determines if the ECAP amplitude of the responsive ECAP is greater than an upper ECAP amplitude threshold. If the ECAP amplitude is greater than the upper ECAP amplitude threshold ("YES" branch of block 1106), processing circuitry 210 activates/continues a decrement mode (1108) in IMD 200. For example, if the decrement mode is already "turned on" in IMD 200 when processing circuitry determines that the ECAP amplitude is greater than the upper ECAP amplitude threshold, then processing circuitry 210 maintains IMD 200 in the decrement mode. If the decrement mode is "turned off" in IMD 200 when processing circuitry determines that the ECAP amplitude is greater than the upper ECAP amplitude threshold, then processing circuitry 210 activates the decrement mode to reduce the pulse amplitude from a predetermined value programmed for stimulation. In some examples, the decrement mode may be stored in storage device 212 as a part of control policy 213. The decrement mode may be a set of instructions which causes IMD 200 to decrease one or more parameter values of each consecutive informed pulse and decrease one or more parameter values of each consecutive control pulse. For example, when the decrement mode is activated, processing circuitry 210 may decrease an electric current amplitude of each consecutive informed pulse delivered by IMD 200 and decrease an electric current amplitude of each consecutive control pulse delivered by IMD 200. After processing circuitry 210 activates/continues the decrement mode, the example operation may return to block 1102 and IMD 200 may deliver another control pulse.

If the ECAP amplitude is not greater than the ECAP amplitude threshold ("NO" branch of block 1106), processing circuitry 210 determines whether the ECAP amplitude is less than a lower ECAP amplitude threshold in block 1110. If the ECAP amplitude is less than the lower ECAP amplitude threshold ("YES" branch of block 1110), processing circuitry 210 activates an increment mode (1112) in IMD 200. In some examples, the increment mode may be stored in storage device 212 as a part of control policy 213. The increment mode may be a set of instructions which causes IMD 200 to increase one or more parameter values of each consecutive informed pulse and increase one or more parameter values of each consecutive control pulse. For example, when the increment mode is activated, processing circuitry 210 may increase an electric current amplitude of each consecutive informed pulse delivered by IMD 200 and increase an electric current amplitude of each consecutive control pulse delivered by IMD 200. After processing circuitry 210 activates the increment mode, the example operation may return to block 1102 and IMD 200 may deliver another control pulse. Processing circuitry 210 may continue to increment the pulse amplitude until the pulse amplitude returns to the predetermined value of the amplitude programmed for delivery prior to the ECAP amplitude exceeding the upper ECAP amplitude threshold.

If the ECAP amplitude is not less than the lower ECAP amplitude threshold ("NO" branch of block 1110), processing circuitry 1114 maintains the pulse amplitude currently used to at least partially define parameter values. In this manner, when the ECAP amplitude is between the upper ECAP amplitude threshold and the lower ECAP amplitude threshold, processing circuitry 210 does not increase the amplitude value back to the predetermined value or decreased the amplitude. This "buffer" zone may reduce oscillating amplitude values when the ECAP amplitudes are similar to the ECAP amplitude threshold. These oscillating amplitude values may be perceived as uncomfortable or unwanted by the patient. However, once the ECAP amplitude drops below the lower ECAP amplitude threshold, processing circuitry 210 can return the amplitude value back to the predetermined amplitude value intended for therapy.

In some examples, the upper ECAP amplitude threshold and the lower ECAP amplitude threshold are defined. In other examples, processing circuitry 210 may define the upper ECAP amplitude threshold and/or the lower ECAP amplitude threshold as a buffer or deviation from a single defined ECAP threshold value. For example, processing circuitry 210 may define the lower ECAP amplitude threshold based on an upper ECAP amplitude threshold defined by a user or calculated from initial patient perception thresholds and/or discomfort thresholds. Although FIG. 11 describes adjusting amplitudes for both informed pulses and control pulses, the technique of FIG. 11 may also apply when IMD 200 is delivering only control pulses (e.g., without informed pulses) to the patient for therapy.

Figure 12:
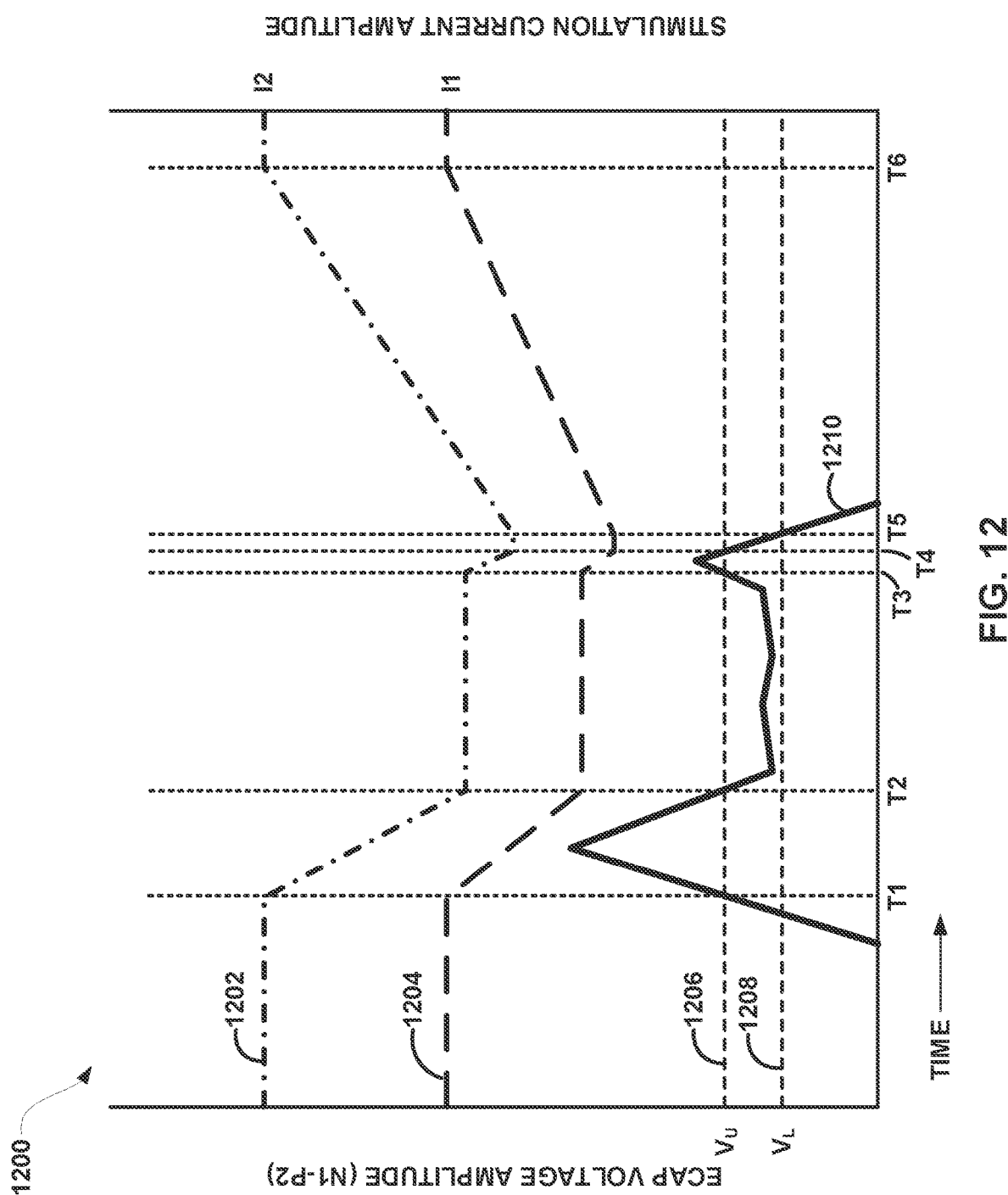
FIG. 12 illustrates a voltage/current/time graph which plots control pulse current amplitude, informed pulse current amplitude, and ECAP voltage amplitude as a function of time, in accordance with one or more techniques of this disclosure.

FIG. 12 illustrates a voltage/current/time graph 1200 which plots control pulse current amplitude 1202, informed pulse current amplitude 1204, and ECAP voltage amplitude 1210 as a function of time, in accordance with one or more techniques of this disclosure. Additionally, FIG. 12 illustrates upper threshold ECAP amplitude 1206 and lower threshold ECAP amplitude 1208. FIG. 12 may be similar to FIG. 10, but FIG. 12 illustrates a technique in which two thresholds for ECAP voltage amplitude 1210 are employed to provide a buffer that may reduce possible oscillations in pulse amplitude if the ECAP amplitude oscillates near a single ECAP amplitude threshold. For convenience, FIG. 10 is described with respect to IMD 200 of FIG. 2. However, the techniques of FIG. 12 may be performed by different components of IMD 200 or by additional or alternative medical devices.

Voltage/current/time graph 1200 illustrates a relationship between sensed ECAP voltage amplitude and stimulation current amplitude. For example, control pulse current amplitude 1202 and informed pulse current amplitude 1204 are plotted alongside ECAP voltage amplitude 1210 as a function of time, thus showing how IMD 200 is configured to change stimulation current amplitude relative to detected ECAP voltage amplitude (or some other ECAP characteristic value). In some examples, IMD 200 delivers a plurality of control pulses and a plurality of informed pulses at control pulse current amplitude 1202 and informed pulse current amplitude 1204, respectively. Initially, IMD 200 may deliver a first set of control pulses, where IMD 200 delivers the first set of control pulses at current amplitude I2. Additionally, IMD 200 may deliver a first set of informed pulses, where IMD 200 delivers the first set of informed pulses at current amplitude I1. I1 and I2 may be referred to as a predetermined value for the amplitude of respective control and informed pulses. This predetermined value may be a programmed value or otherwise selected value that a stimulation program has selected to at least partially define stimulation pulses to the patient in the absence of transient conditions (e.g., when the ECAP amplitude is below a threshold ECAP value). The first set of control pulses and the first set of informed pulses may be delivered prior to time T1. In some examples, I1 is 4 milliamps (mA) and I2 is 8 mA. Although informed pulse current amplitude 1202 is shown as greater than control pulse current amplitude 1204, informed pulse current amplitude 1202 may be less than or the same as control pulse current amplitude 1204 in other examples.

While delivering the first set of control pulses and the first set of informed pulses, IMD 200 may determine ECAP voltage amplitude 1210 from respective ECAP signals. During dynamic and transient conditions which occur in patient 105 such as coughing, sneezing, laughing, Valsalva maneuvers, leg lifting, cervical motions, or deep breathing, ECAP voltage amplitude 1210 may increase if control pulse current amplitude 1202 and informed pulse current amplitude 1204 are held constant. This increase in ECAP voltage amplitude 1210 may be caused by a reduction in the distance between the electrodes and nerves. For example, as illustrated in FIG. 12, ECAP voltage amplitude 1208 may increase prior to time T1 while stimulation current amplitude is held constant. An increasing ECAP voltage amplitude 1208 may indicate that patient 105 is at risk of experiencing transient overstimulation due to the control pulses and the informed pulses delivered by IMD 200. However, IMD 200 may not take any action until ECAP voltage amplitude 1210 exceeds, or is greater than, upper threshold ECAP amplitude 1206. To prevent patient 105 from experiencing transient overstimulation, IMD 200 may decrease control pulse current amplitude 1202 and informed pulse current amplitude 1204 in response to ECAP voltage amplitude 12010 exceeding the upper threshold ECAP amplitude 1206. For example, if IMD 200 senses an ECAP having an ECAP voltage amplitude 1210 meeting or exceeding upper threshold ECAP amplitude 1206, as illustrated in FIG. 12 at time T1, IMD 200 may enter a decrement mode where IMD 200 decreases control pulse current amplitude 1202 and informed pulse current amplitude 1204. In some examples, the upper threshold ECAP amplitude 1206 is selected from a range of approximately 5 microvolts (Or) to approximately 30 μV, or from a range of approximately 10 microvolts (Or) to approximately 20 μV. For example, the upper threshold ECAP amplitude 1206 is 15 μN. In other examples, the upper threshold ECAP amplitude 1206 is less than or equal to 5 μV or greater than or equal to 30 μV. In some examples, IMD 200 may determine upper threshold ECAP amplitude 1206 from a target threshold, such that upper threshold ECAP amplitude 1206 is above the target threshold and lower threshold ECAP amplitude 1208 is below the target threshold.

IMD 200 may respond relatively quickly to the ECAP amplitude 1210 exceeding the upper threshold ECAP amplitude 1206. For example, IMD may be configured to detect threshold exceeding ECAP amplitudes within 20 milliseconds (ms). If IMD 200 delivers control pulses at a frequency of 50 Hz, the period of time for a single sample that includes delivering the control pulse and detecting the resulting ECAP signal may be 20 ms or less. However, since an ECAP signal may occur within one or two ms of delivery of the control pulse, IMD 200 may be configured to detect an ECAP signal exceeding the threshold ECAP amplitude in less than 10 ms. For transient conditions, such as a patient coughing or sneezing, these sampling periods would be sufficient to identify ECAP amplitudes exceeding the threshold and a responsive reduction in subsequent pulse amplitudes before the ECAP amplitude would have reached higher levels that may have been uncomfortable for the patient.

The decrement mode may, in some cases, be stored in storage device 212 of IMD 200 as a part of control policy 213. In the example illustrated in FIG. 10, the decrement mode is executed by IMD 200 over a second set of control pulses and a second set of informed pulses which occur between time T1 and time T2. In some examples, to execute the decrement mode, IMD 200 decreases the control pulse current amplitude 1202 of each control pulse of the second set of control pulses according to a first function with respect to time. In other words, IMD 200 decreases each consecutive control pulse of the second set of control pulses proportionally to an amount of time elapsed since a previous control pulse. Additionally, during the decrement mode, IMD 200 may decrease the informed pulse current amplitude 1204 of each informed pulse of the second set of informed pulses according to a second function with respect to time. Although linear first and second functions are shown, the first and/or second function may be non-linear, such as logarithmic (e.g., the rate of change decreases over time), exponential (e.g., the rate of change increases over time), parabolic, step-wise, multiple different functions, etc., in other examples. During a period of time in which IMD 200 is operating in the decrement mode (e.g., time interval T2-T1), ECAP voltage amplitude 1210 of ECAPs sensed by IMD 200 may be greater than or equal to upper threshold ECAP amplitude 1206.

In the example illustrated in FIG. 12, IMD 200 may sense an ECAP at time T2, where the ECAP has an ECAP voltage amplitude 1210 that is less than upper threshold ECAP amplitude 1206. However, ECAP voltage amplitude 1210 may still be greater than lower threshold ECAP amplitude 1208. Within this zone between upper threshold ECAP amplitude 1206 and lower threshold ECAP amplitude 1208, IMD 200 may maintain control pulse current amplitude 1202 and informed pulse current amplitude 1204 (e.g., between T2 and T3). By not immediately increasing the amplitudes for both control pulse current amplitude 1202 and informed pulse current amplitude 1204 in response to ECAP voltage amplitude 1210 dropping below upper threshold ECAP amplitude 1206, IMD 200 may prevent these pulse amplitudes from increasing again only to be subjected to another spike in ECAP voltage amplitude 1210. These subsequent spikes could be perceived by the patient has undesirable waves or oscillations in therapy intensity. Lower threshold ECAP amplitude 1208 may be set as a percentage of, or absolute value below, upper threshold ECAP amplitude 1206 or a target threshold. In some examples, the zone between upper threshold ECAP amplitude 1206 and lower threshold ECAP amplitude 1208 may have a predetermined magnitude and/or be adjustable by a patient or physician. For example, upper threshold ECAP amplitude 1206 and/or lower threshold ECAP amplitude 1208 may be adjusted to increase the zone if the patient still experiences oscillations in therapy intensity.

At T3, IMD 200 may again detect that ECAP voltage amplitude 1210 exceeds upper threshold ECAP amplitude 1206 and responsively decrease control pulse current amplitude 1202 and informed pulse current amplitude 1204 even further. At time T4, ECAP voltage amplitude 1210 drops below upper threshold ECAP amplitude 1206 but is still greater than lower threshold ECAP amplitude 1208. Therefore, between times T4 and T5, IMD 200 may maintain control pulse current amplitude 1202 and informed pulse current amplitude 1204. At time T5, IMD 200 determines that ECAP voltage amplitude 1210 drops below and is less than lower threshold ECAP amplitude 1208. In response to ECAP voltage amplitude 1210 dropping below lower threshold ECAP amplitude 1208, IMD 200 may begin to increase control pulse current amplitude 1202 and informed pulse current amplitude 1204 back up to the respective predetermined values I1 and I2 at time T6. If ECAP voltage amplitude 1210 would have again exceeded upper threshold ECAP amplitude 1206 before time T6, IMD 200 would have reduced control pulse current amplitude 1202 and informed pulse current amplitude 1204 as discussed above with respect to the time period between T1 and T2.

The rate of change in amplitude of the pulses may be relatively instantaneously (e.g., a very fast rate) in other examples. For example, in response to ECAP voltage amplitude 1210 exceeding upper threshold ECAP amplitude 1206, IMD 200 may immediately drop the amplitude of one or both of control pulse current amplitude 1202 or informed pulse current amplitude 1204 to a predetermined or calculated value. Then, in response to ECAP voltage amplitude 1210 dropping back below lower threshold ECAP amplitude 1208, IMD 200 may enter increment mode as described above.

When control pulse current amplitude 1002 and informed pulse current amplitude 1004 return to current amplitude I2 and current amplitude I1 (e.g., the predetermined value or programmed value for each type pulse), respectively, IMD 200 may deactivate the increment mode and deliver stimulation pulses at constant current amplitudes once again. By decreasing stimulation in response to ECAP amplitudes exceeding the upper threshold and subsequently increasing stimulation in response to ECAP amplitudes falling below the lower threshold, IMD 200 may prevent patient 105 from experiencing transient overstimulation or decrease a severity of transient overstimulation experienced by patient 105, while also reducing potential oscillations that could occur with a single threshold, whether the decrease is in terms of the length of the experience, the relative intensity, or both.

FIG. 12 is described in the situation in which IMD 200 delivers both control pulse and informed pulses. However, IMD 200 may apply the technique of FIG. 10 to the situation in which only control pulses are delivered to provide therapy to the patient and elicit detectable ECAP signals. In this manner, IMD 200 would similarly enter a decrement mode or increment mode for control pulse current amplitude 1202 based on the detected ECAP voltage amplitude 1210 without adjusting the amplitude or other parameter of any other type of stimulation pulse.

Figure 13:
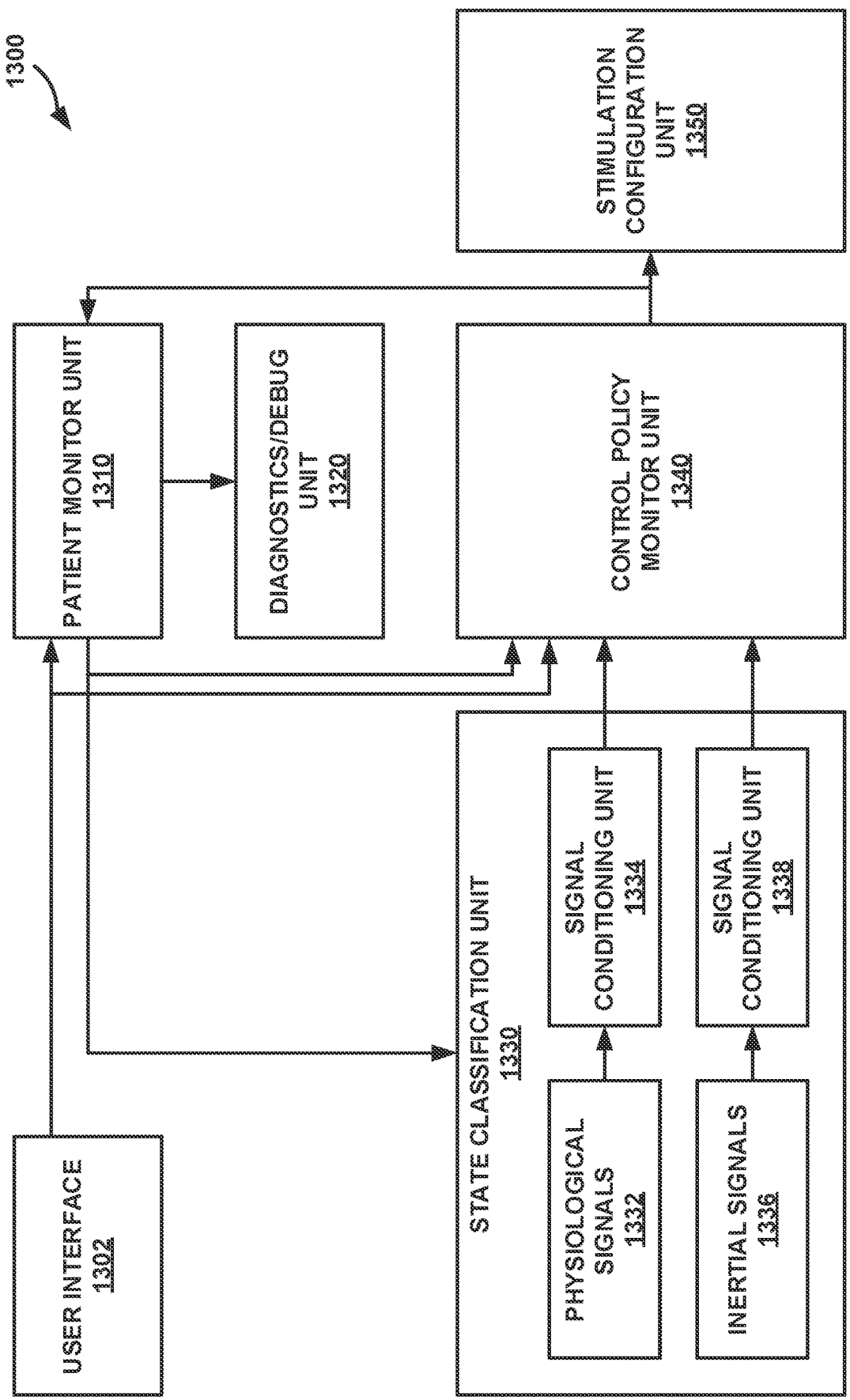
FIG. 13 is a block diagram illustrating a system for determining a control policy of an IMD, in accordance with one or more techniques of this disclosure.

FIG. 13 is a block diagram illustrating a system 1300 for determining a control policy 1300 of an IMD, in accordance with one or more techniques of this disclosure. As seen in FIG. 13, system 1300 includes user interface 1302, control policy monitor unit 1310, diagnostics/debug unit 1320, state classification unit 1330, control policy unit 1340, and stimulation configuration unit 1350.

In some examples, state classification unit 1330 may estimate the state of a monitored system based on input data. For example, ECAPs may represent inputs to state classification unit 1330 to estimate tissue activation (e.g., ECAP characteristic values) during the delivery of one or more stimulation pulses to target tissue of a patient (e.g., spinal cord 120 of patient 105). State classification unit 1330 may generate one or more outputs for sending to control policy unit 1340. In turn, control policy unit 1340 may receive the one or more outputs from state classification unit 1330 and receive one or more additional inputs from other parts of the system or external sources (e.g., conditioned signals, patient input, control policy monitor unit 1310). Control policy unit 1340 may determine a control policy based on the received inputs, where the control policy drives one or more therapy configuration updates at stimulation configuration unit 1350. It may be beneficial to make adjustments to state classification unit 1330 and control policy unit 1340 as patient symptoms and other factors change (e.g., lead migration).

System 1300 may monitor attributes of input data (e.g., outputs of state classification unit 1330 and outputs of control policy monitor unit 1310) and generate a control policy in order to improve a performance of IMD 110 as compared with systems that do not use input data to determine a control policy. For example, system 1300 may decrease a number of patient interactions required to update a system configuration and decrease a number of sudden unwanted changes in a perceived level of paresthesia delivered by IMD 110 (e.g., transient overstimulation events) as compared with systems that do not determine control policy based on measured signals. Additionally, control policy unit 1340 may adjust stimulation delivered by IMD 110 based on a time of day.

As seen in FIG. 13, input signals, e.g., physiological signals 1332 and inertial signals 1336, may be conditioned by signal conditioning unit 1334 and signal conditioning unit 1338, respectively. In some examples, physiological signals 1332 may include cardiac signals (e.g., heart rate, heart rate variability, blood pressure, and blood pressure variability), respiratory signals (e.g., respiratory rate and respiratory rate variability), and ECAPs. In some examples, inertial signals 1336 may include accelerometer data and/or gyroscope data which indicate patient motion and patient posture. During conditioning, one or more features may be calculated to identify one or more attributes of the input signals. State classification unit 1330 may use these attributes to categorize a state of stimulation delivered by IMD 110 (e.g., too much tissue or too little tissue activated). The determined state may be leveraged as an input to the control policy determined by control policy unit 1340. Other inputs to the control policy unit 1340 may include one or more user inputs from user interface 1302 and one or more inputs from control policy monitor unit 1310. After control policy unit 1340 determines a control policy based on the inputs, control policy unit 1340 may output an instruction to set one or more stimulation parameters using stimulation configuration unit 1350.

In some examples, one or more configurable parameters that define the control policy can be determined by control policy unit 1340. The one or more parameters may include, for example, an upper bound and a lower bound of a buffer zone, an overstimulation threshold, a maximum stimulation amplitude, a minimum stimulation amplitude, a stimulation increment step size, a stimulation increment step duration, a stimulation decrement step size, a stimulation decrement step duration, and a scaling factor between control pulse amplitude and informed pulse amplitude. The attributes monitored by control policy monitor unit 1310 may include, for example, any one or combination of a number of state changes within a period of time, a number, frequency, or time of day of patient adjustments, a lack of control policy state changes, reported undesirable stimulation events, and changes in stimulation amplitude.

In some examples, processing circuitry (e.g., processing circuitry of IMD 110 and/or processing circuitry of external programmer 150) may execute any one or combination of control policy monitor unit 1310, diagnostics/debug unit 1320, state classification unit 1330, control policy unit 1340, and stimulation configuration unit 1350.

Figure 14:
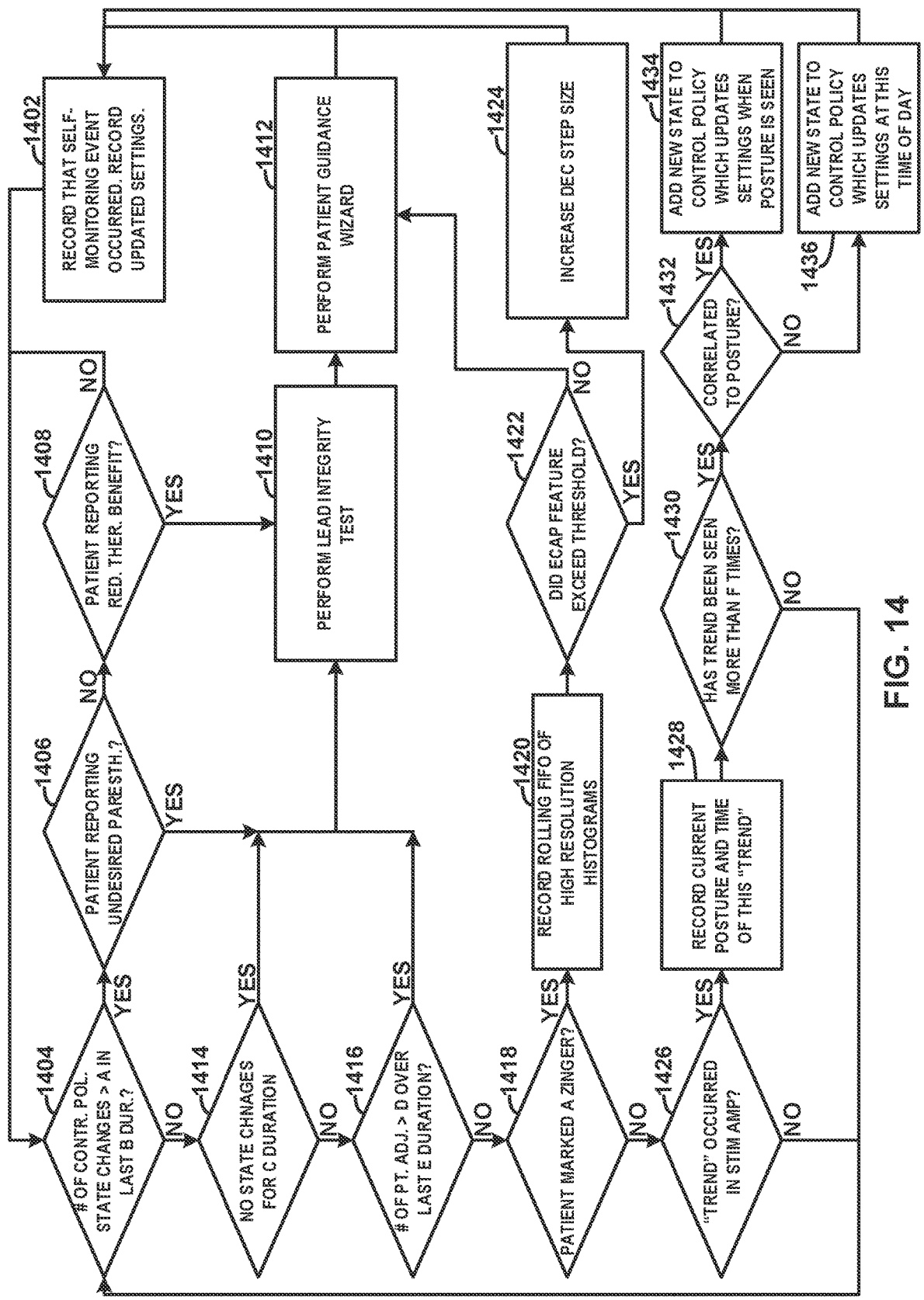
FIG. 14 is a flow diagram illustrating an example operation for adjusting a control policy for the IMD of FIG. 1, in accordance with one or more techniques of this disclosure.

FIG. 14 is a flow diagram illustrating an example operation for adjusting the control policy for IMD 110, in accordance with one or more techniques of this disclosure. FIG. 14 is described with respect to IMD 110, and external programmer 150 of FIG. 1, IMD 200 of FIG. 2, and external programmer 300 of FIG. 3. However, the techniques of FIG. 14 may be performed by different components of IMD 110, external programmer 150, IMD 200, and external programmer 300, or by additional or alternative medical devices.

Processing circuitry may record an occurrence of a self-monitoring event and record one or more update settings (1402) associated with the self-monitoring event. Processing circuitry may determine whether a number of control policy state changes within a first duration is greater than a threshold number of control policy state changes (1404). When the number of control policy state changes is greater than the threshold number of control policy state changes ("YES" branch of block 1404), processing circuitry may determine whether a patient indication of an undesired paresthesia (1406) is received. When a patient indication of an undesired paresthesia is not received ("NO" branch of block 1406), processing circuitry may determine whether a patient indication of a reduced therapeutic benefit is received (1408). When a patient indication of a reduced therapeutic benefit is not received ("NO" branch of block 1408), processing circuitry may determine that no control policy changes are required.

When a patient indication of an undesired paresthesia is received ("YES" branch of block 1406) or when a patient indication of a reduced therapeutic benefit is received ("YES" branch of block 1408), processing circuitry may perform a lead integrity test of one or more of leads 130 (1410). Subsequently, processing circuitry \ may execute a "patient guidance wizard" algorithm (1412). After executing the patient guidance wizard algorithm, processing circuitry may recommend one or more control policy changes for implementation by IMD 110.

When the number of control policy state changes is not greater than the threshold number of control policy state changes ("NO" branch of block 1404), processing circuitry may determine whether zero state changes occur during a second duration (1414). If zero state changes occur during the second duration ("YES" branch of block 1414), processing circuitry may perform the lead integrity test (1410) on one or more of leads 130. If more than zero state changes occur during the second duration ("NO" branch of block 1414), processing circuitry determines whether a number of patient parameter adjustments is greater than a threshold number of patient parameter adjustments during a third duration (1416). If the number of patient parameter adjustments is greater than the threshold number of patient parameter adjustments during the third duration ("YES" branch of block 1416), processing circuitry may perform the lead integrity test (1410) on one or more of leads 130. If the number of patient parameter adjustments is not greater than the threshold number of patient parameter adjustments during the third duration ("NO" branch of block 1416), external programmer 150 may determine whether an indication of an uncomfortable sensation is received (1418). An uncomfortable sensation may be referred to herein as a "zinger." Processing circuitry may be configured to communicate with an external programmer, such as external programmer 300 of FIG. 3. User interface 356 may receive a user input indicating an undesirable attribute of a sensation and direct the user input to processing circuitry.

When processing circuitry determines that indication of an uncomfortable sensation is received ("YES" branch of block 1418), processing circuitry outputs a request to record histogram data stored by a rolling buffer (1420) of IMD 110. In some examples, processing circuitry may receive the histogram data and analyze the histogram data, which represents histogram data of a set of ECAPs which are sensed by IMD 110 responsive to stimulation pulses delivered by IMD 110. In order to analyze the histogram data, processing circuitry may determine whether one or more ECAP features exceed an ECAP feature threshold (1422). For example, if the histogram data indicates that one or more ECAP features do not exceed an ECAP feature threshold ("NO" branch of block 1422), processing circuitry may initiate the patient guidance wizard (1412) in order to obtain information relating to the uncomfortable sensation indicated by the patient. When the histogram data indicates that one or more ECAP features does exceed an ECAP feature threshold ("YES" branch of block 1422), processing circuitry may output a recommendation to change a control policy of IMD 110 by increasing a decrement step size (1424) of one or more stimulation pulses delivered by IMD 110. For example, IMD 110 may be programmed to decrement stimulation pulses in response to detecting an increase in ECAP amplitudes. By increasing the decrement step size, processing circuitry may decrease a likelihood that patient 105 experiences a transient overstimulation event in the future.

When processing circuitry determines that indication of an uncomfortable sensation is not received ("NO" branch of block 1418), processing circuitry may determine whether a trend exists in amplitudes of stimulation pulses delivered by IMD 110 over a period of time (1426). When processing circuitry identifies a trend ("YES" branch of block 1426), processing circuitry determines, based on accelerometer data, a current posture of patient 105 and records a current time of day during the period of time in which the trend occurs (1428). The trend may represent a trend of stimulation amplitudes that induces a desired sensation in patient 105 while the patient is assuming the posture. Processing circuitry may determine whether the trend has occurred more than a threshold number of times over a period of time (1430). If the trend has occurred more than the threshold number of times ("YES" branch of block 1430), processing circuitry may determine whether the trend is correlated with a posture of patient 105 (1432). If processing circuitry determines that the trend is correlated with posture ("YES" branch of block 1432), processing circuitry may add a new state to a control policy of IMD 110 (1434) which updates one or more stimulation parameters when the trend is detected. If processing circuitry determines that the trend is not correlated with posture ("NO" branch of block 1432), processing circuitry may add a new state to a control policy of IMD 110 (1436) which updates one or more stimulation parameters at the time of day in which the trend was detected.

Figure 15:
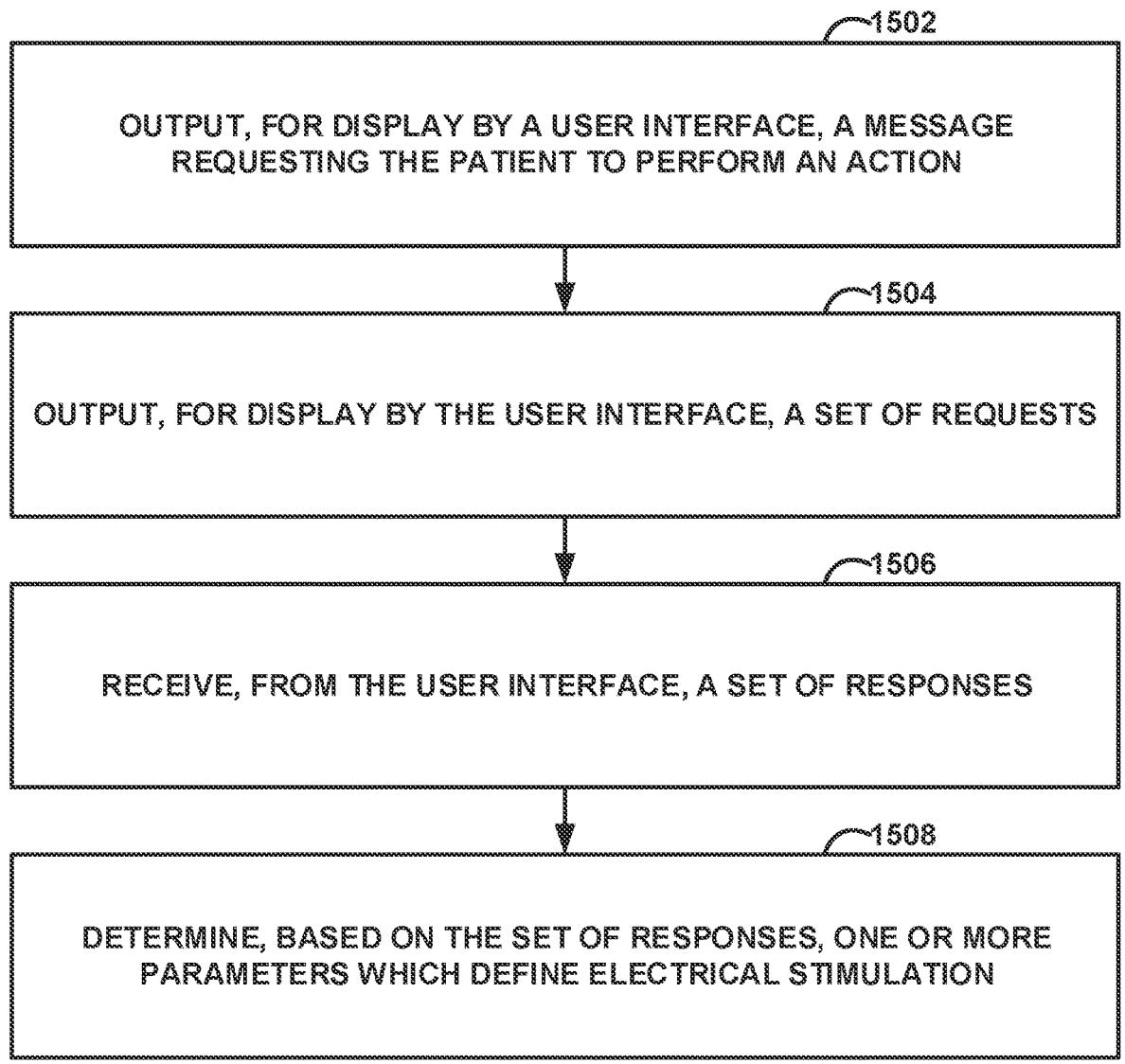
FIG. 15 is a flow diagram illustrating an example operation for generating a recommendation for controlling one or more therapy parameters, in accordance with one or more techniques of this disclosure.

FIG. 15 is a flow diagram illustrating an example operation for generating a recommendation for controlling one or more therapy parameters, in accordance with one or more techniques of this disclosure. For convenience, FIG. 15 is described with respect to IMD 110, and external programmer 150 of FIG. 1, IMD 200 of FIG. 2, and external programmer 300 of FIG. 3. However, the techniques of FIG. 15 may be performed by different components of IMD 110, external programmer 150, IMD 200, and external programmer 300, or by additional or alternative medical devices.

Processing circuitry may execute an algorithm for recommending changes to a control policy which determines one or more parameters for electrical stimulation delivered by IMD 110. For example, it may be beneficial to customize electrical stimulation parameters on a patient-by-patient basis, since leads 130 may be implanted slightly differently in each patient. For example, a distance between electrodes 232, 234 and target tissue of patient 105 may be different than the distance between electrodes and target tissue of another patient. Additionally, leads 130 may migrate within patient 105 over a period of time, thus changing the stimulation parameters required for patient 105 to experience a desired effect. Processing circuitry may execute the algorithm in order to obtain information for determining one or more parameter recommendations in order to prevent IMD 110 from delivering transient overstimulation to patient 105.

Processing circuitry may output, for display by a user interface (e.g., user interface 356 of FIG. 3), a message requesting patient 105 to perform an action (1502). The message for display by the user interface may be in the form of text, e.g., "COUGH ONCE," "PLEASE ARCH YOUR BACK," but this is not required. The message may include symbols, such as symbols depicting the action which patient 105 is prompted to perform. In some examples, processing circuitry may output the message in response to receiving an instruction to execute an algorithm. In some examples, processing circuitry outputs the message without receiving a prompt to output the message. Processing circuitry may receive a message indicating that the action is complete, but this is not required. In some examples, processing circuitry may proceed with the algorithm without receiving indication that the action by patient 105 is complete.

Processing circuitry may output, for display by the user interface, a set of requests (1504). Processing circuitry may output the set of requests for display by user interface in a sequence. That is, processing circuitry may output a first request for display, followed by a second request for display, followed by a third request for display, and so on. The set of requests may represent requests for information, such as requests for information as to an existence or a nature of one or more sensations experienced by patient 105 which relate to the action performed by patient 105. For example, the set of requests may include one or more requests prompting the user to indicate whether the action caused an undesirable attribute during the action and/or after the action. The set of requests may also include one or more requests prompting the user to indicate an identity (e.g., intense sensation, increased location, pulsating sensation, tingling sensation, pressure sensation, tapping sensation, vibration sensation, or any combination thereof) of the undesirable attribute.

In some examples, processing circuitry may output the one or more requests prompting the user to indicate the identity of the sensation as a menu of sensations for selection via the user interface. In some examples, processing circuitry may output the one or more requests prompting the user to indicate the identity of the sensation as a sequence of requests. Each request of the sequence of requests may include a prompt for patient 105 to indicate whether a particular sensation occurred responsive to the action.

Processing circuitry may receive, from the user interface, a set of responses (1506). In some examples, the set of responses may include a response corresponding to each request of the set of requests, but this is not required. In some examples, the set of responses might not include a response to one or more requests of the set of requests. When a first request of the set of requests includes a prompt for the user to indicate whether the action caused an undesirable attribute during the action, a first response of the set of responses may include either a "yes" response or a "no" response indicating whether the action caused an undesirable attribute. In some examples, processing circuitry may receive the set of responses as a sequence of responses. For example, the set of requests and the set of responses may be interleaved such that processing circuitry receives a response to a respective request before outputting a subsequent request of the sequence of requests. Processing circuitry may determine, based on the set of responses, one or more parameters which define electrical stimulation (1508) delivered by IMD 110. Processing circuitry may determine the one or parameters based on whether the set of requests indicate an undesirable attribute, when an undesirable attribute occurs relative to an action, an identity of an undesirable attribute, or any combination thereof.

Figure 16:
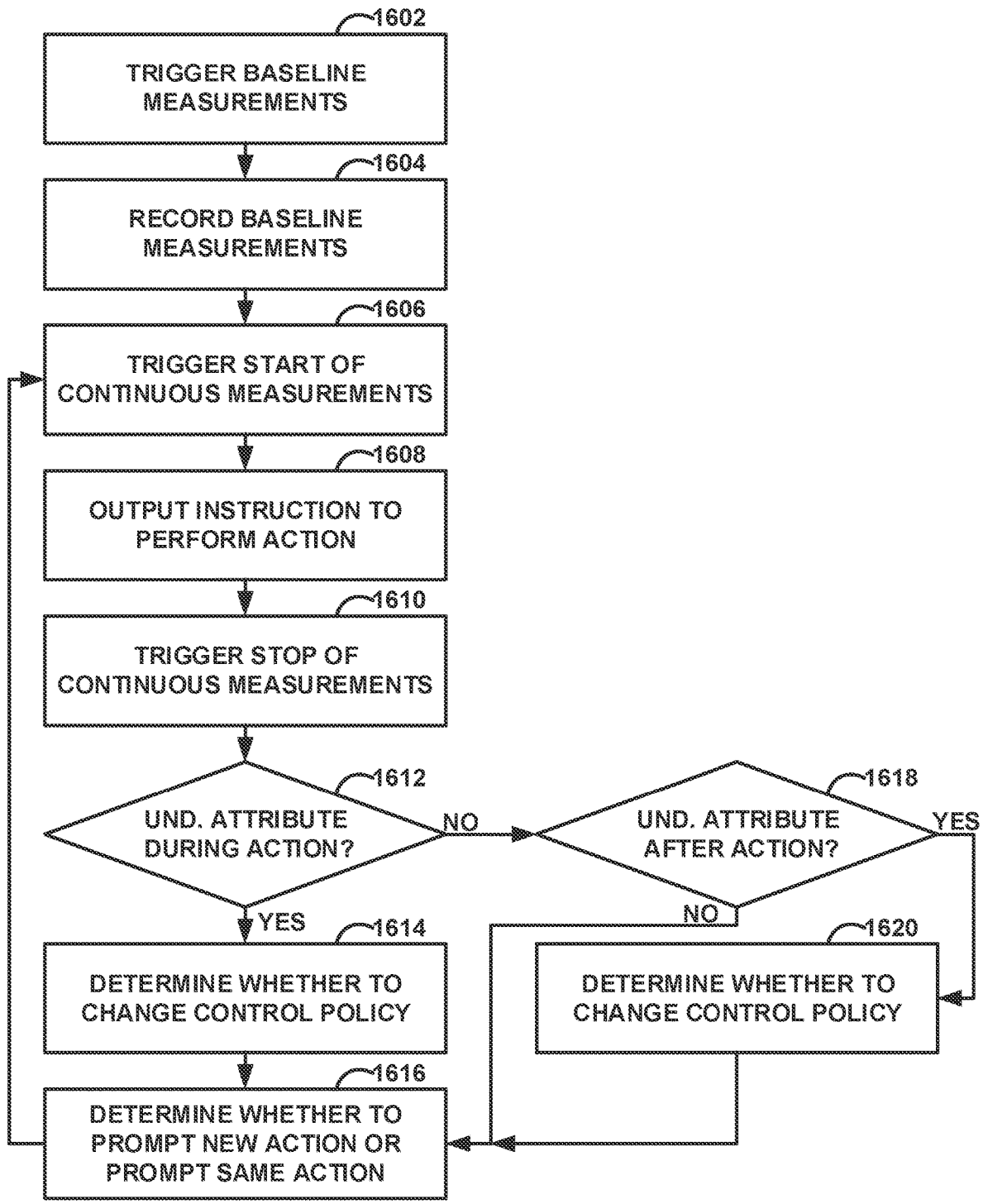
FIG. 16 is a flow diagram illustrating an example operation for outputting one or more requests and receiving one or more responses in order to adjust stimulation to a patient by the IMD of FIG. 1, in accordance with one or more techniques of this disclosure.

FIG. 16 is a flow diagram illustrating an example operation for outputting one or more requests and receiving one or more responses in order to adjust stimulation to a patient by IMD 110, in accordance with one or more techniques of this disclosure. FIG. 16 is described with respect to IMD 110, and external programmer 150 of FIG. 1, IMD 200 of FIG. 2, and external programmer 300 of FIG. 3. However, the techniques of FIG. 16 may be performed by different components of IMD 110, external programmer 150, IMD 200, and external programmer 300, or by additional or alternative medical devices.

In some examples, the example operation of FIG. 16 includes outputting one or more requests and receiving one or more responses to these requests in order to determine one or more parameters for delivering electrical stimulation to patient 105. Processing circuitry may trigger IMD 110 to collect one or more baseline measurements (1602). For example, before guiding patient 105 to perform any actions, processing circuitry may trigger a recording of baseline data in the neurostimulator and processing circuitry may prompt patient 105 to rate various perceptual levels. The baseline measurements may include, for example, accelerometer data, temperature data, blood oxygenation data, ECAP data, heart rate, blood pressure, tissue impedance, or any combination thereof. Subsequently, IMD 110 may record baseline measurements (1604).

Processing circuitry may trigger IMD 110 to start continuous measurements (1606). For example, before guiding patient 105 to perform one or more actions, processing circuitry may trigger the IMD 110 to start a continuous recording of parameters such as stimulation amplitude, ECAP features, a current classification of a feature (e.g., a stimulation feature and/or an ECAP feature), current control policy state, or any combination thereof. Subsequently, processing circuitry may output an instruction for patient 105 to perform an action (1608). In some examples, block 1608 may be an example of block 1502 of FIG. 15. After outputting the instruction, processing circuitry may trigger IMD 110 to stop recording the continuous measurements (1610). In some examples, processing circuitry may instruct IMD 110 to perform the continuous measurements so that data corresponding to one or more patient parameters during the performance of the action is accessible for analysis. In some cases, processing circuitry may analyze ECAP data during the performance of the action in order to determine one or more stimulation parameter adjustments for avoiding transient overstimulation.

Processing circuitry may output a request representing a prompt to indicate whether an undesirable attribute of a sensation occurred during a performance of the action (1612). If processing circuitry receives a response indicating that an undesirable attribute occurred during the action ("YES" branch of block 1612), processing circuitry may determine whether to change the control policy (1614) which determines electrical stimulation delivered by IMD 110. Processing circuitry may determine whether to prompt patient 105 to perform or a new action or prompt patient 105 to perform the same action (1616). If processing circuitry receives a response indicating that an undesirable attribute did not occur during the action ("NO" branch of block 1612), processing circuitry may output a prompt to indicate whether an undesirable attribute occurred after a performance of the action (1618).

If processing circuitry receives a response indicating that an undesirable attribute occurred after the action ("YES" branch of block 1618), processing circuitry may determine whether to change a control policy (1620) which determines electrical stimulation delivered by IMD 110 and subsequently the example operation proceeds to block 1616. If processing circuitry receives a response indicating that an undesirable attribute did not occur after the action ("NO" branch of block 1618), the example operation proceeds to block 1616.

Figure 17A:
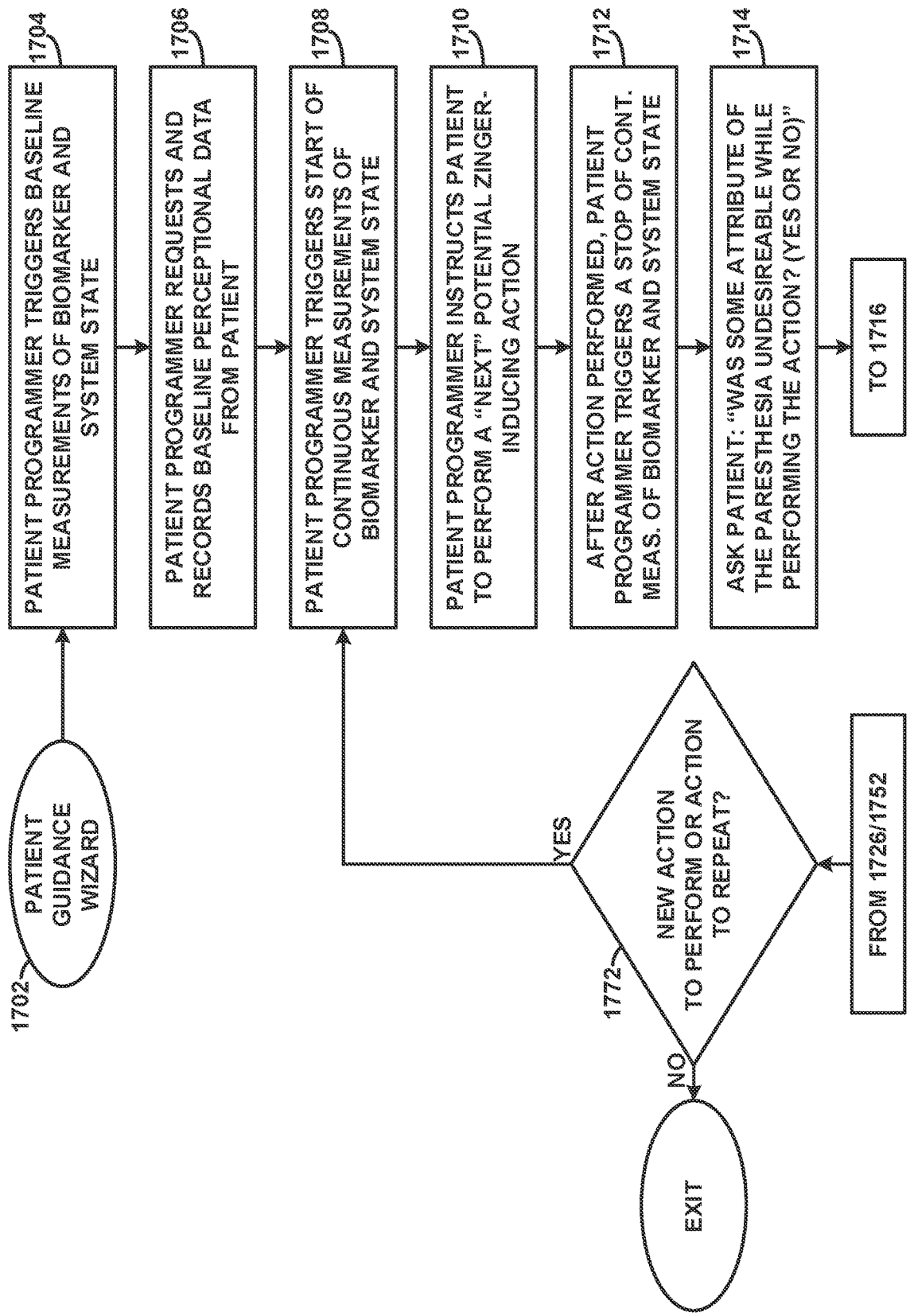
FIGS. 17A-17B are flow diagrams illustrating an example operation for outputting one or more requests and receiving one or more responses, in accordance with one or more techniques of this disclosure.
Figure 17B:
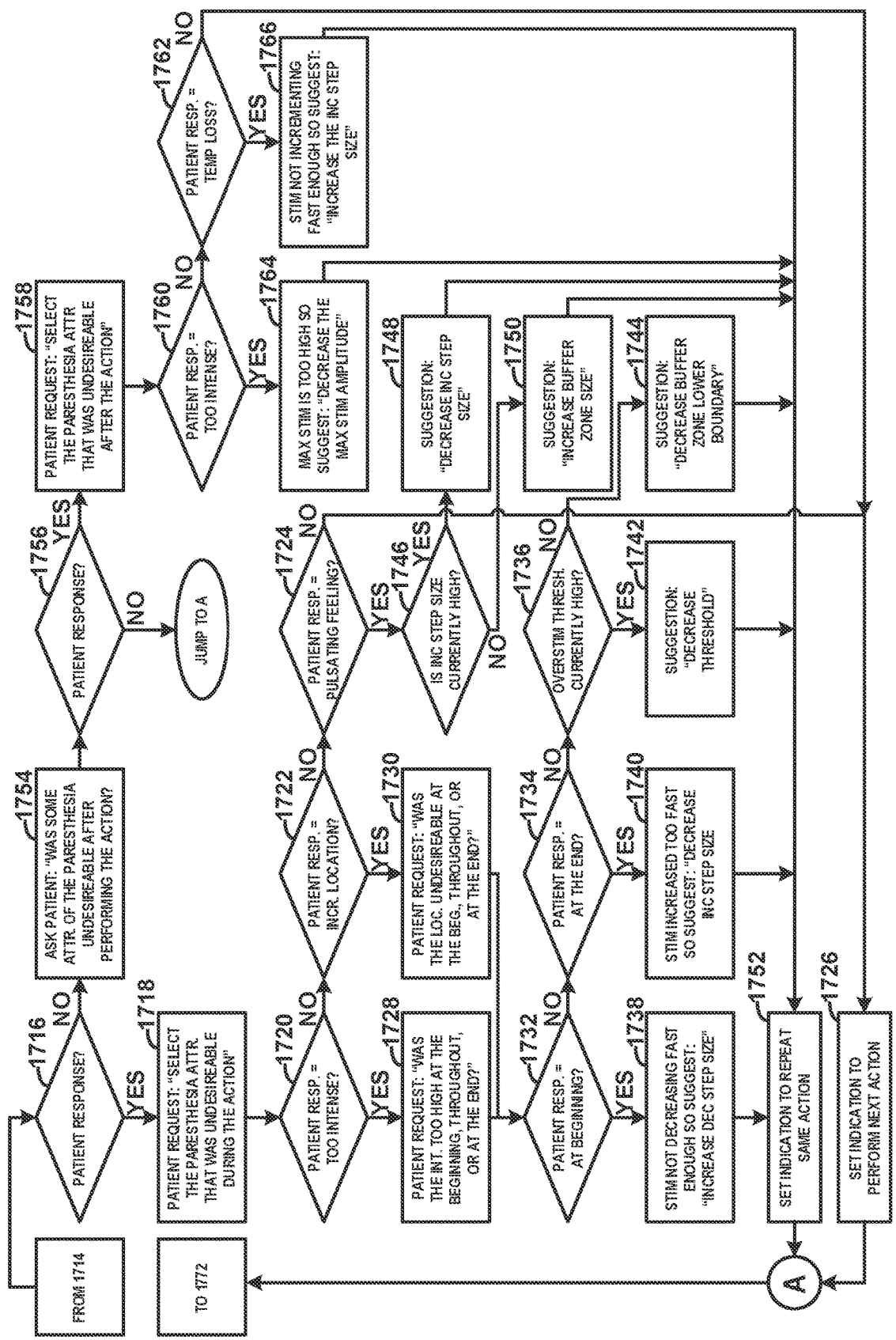

FIGS. 17A-17B are flow diagrams illustrating an example operation for outputting one or more requests and receiving one or more responses, in accordance with one or more techniques of this disclosure. FIGS. 17A-17B are described with respect to IMD 110, and external programmer 150 of FIG. 1, IMD 200 of FIG. 2, and external programmer 300 of FIG. 3. However, the techniques of FIGS. 17A-17B may be performed by different components of IMD 110, external programmer 150, IMD 200, and external programmer 300, or by additional or alternative medical devices.

In some examples, processing circuitry outputs an instruction for display by a user interface of a patient programmer (e.g., user interface 356 of external programmer 300), the instruction representing a prompt for patient 105 to perform an action. After patient 105 completes the action, external programmer 300 may "interview" patient 105 to gather information on specific attributes of one or more sensations felt by patient 105 during or close to a period of time in which patient 105 performs the action. In some examples, processing circuitry may use a current setting of the control policy combined with patient perceptual input to determine a recommended change in a control policy of IMD 110. The recommended change may be implemented automatically by processing circuitry, in some cases, or by a user (e.g., patient 105 or a clinician) in other cases. After the recommended change is implemented, processing circuitry may determine whether to output an instruction for patient 105 to repeat the action in order to perform a follow-up assessment to interview patient 105 again. It may be beneficial for processing circuitry to store patient responses over a period of time in order to employ smarter, improved methods of changing stimulation parameters and store information concerning other stimulation and lead properties (e.g., lead migration) as compared with techniques in which patient responses are not stored.

Processing circuitry may receive an indication to execute an interrogation program (1702). In some cases, the interrogation program may be referred to herein as "Patient Guidance Wizard." In some examples, the indication to execute the interrogation program represents a user input to a device (e.g., an input to user interface 356 of external programmer 300). In some examples, the indication to execute the interrogation program represents an automatic indication, such as a regular indication to execute the interrogation program at a point in time. In some examples, processing circuitry receives the indication in response to external programmer 300 turning on. In some examples, processing circuitry may receive the indication to execute the interrogation program in response to the example operation of FIG. 14 arriving at block 1412.

In order to start the interrogation program, processing circuitry triggers one or more baseline measurements (1704). In some examples, the one or more baseline measurements may include biomarker measurements and system state measurements. For example, the baseline measurements may include one or more of baseline ECAP measurements, baseline heart rate measurements, baseline respiratory rate measurements, baseline blood pressure measurements, and other types of baseline biometric measurements. The one or more baseline measurements may be useful for comparing with one or more parameter measurements captured throughout the interrogation program.

Additionally, processing circuitry may output one or more prompts for information concerning baseline perception levels of patient 105 and a baseline location of paresthesia sensation (1706). In turn, processing circuitry may receive information indicative of the baseline perception levels of patient 105 and the baseline location. Baseline perception levels may represent one or more sensations felt by patient 105 prior to performing any actions related to the interrogation program and the baseline location may represent the location of stimulation prior to performing any actions related to the interrogation program. The one or more prompts for information concerning baseline perception levels of patient 105 may include a prompt for a current status of paresthesia delivered by IMD 110. The prompt for the current status of the paresthesia may include a request for a numerical rating on a scale, such as a rating of the intensity of the stimulation from 1 to 10. In some examples, a "1" rating represents a faint tingling sensation, a "5" rating represents a moderate prickly sensation, and a "10 rating represents a heavy thumping sensation. Additionally, or alternatively, the prompt for the current status of the paresthesia may include a request for a baseline discomfort level of patient 105 with "1" representing the least amount of discomfort and "10" representing the greatest amount of discomfort. The prompt for the baseline location may include a request for an identification of a location (e.g., a location of the body) in which patient 105 feels stimulation.

The processing circuitry triggers IMD 110 to start collecting one or more continuous measurements (1708). As referred to herein, a "continuous measurement" may represent a parameter measurement which is recorded such that changes in the respective parameter may be viewed over the period of time in which the continuous measurement is taken. In other words, a continuous measurement may represent a sequence of samples of the respective parameter, where the sequence of samples is collected by IMD 110 at a sampling rate. In some examples, the one or more continuous measurements may include a continuous heart rate measurement, a continuous blood pressure measurement, a continuous respiratory measurement, a continuous accelerometer measurement, a continuous ECAP measurement, or any combination thereof. The continuous ECAP measurement may represent a continuous sense signal including one or more ECAPS, where processing circuitry is configured to identify the one or more ECAPS in the sense signal.

Processing circuitry outputs an instruction for patient 105 to perform an action (1710) for display by a user interface. The action may include any one or more of a set of transient patient actions such as a cough, a back arch, a Valsalva maneuver, a leg-lift, or another kind of movement. Transient patient actions may include any sort of movement that could possibly cause one or more electrodes of leads 130 to move closer to or farther away from target tissue of patient 105. As an example, responsive to outputting the instruction, user interface 356 may display the message "PLEASE COUGH ONCE," thus instructing the patient to cough in order to perform a transient patient action which may briefly change a distance between the one or more electrodes of leads 130 and target tissue of patient 105. In some examples, processing circuitry may receive, from external programmer 300 or another device, an indication that the action is complete. For example, when the action is one cough, patient 105 may provide an input indicating that the cough is complete to user interface 356, and external programmer 300 may forward the patient input to processing circuitry. Responsive to the action being complete, processing circuitry triggers a stop of collecting one or more continuous measurements (1712). In some examples, processing circuitry may save the one or more continuous measurements to a memory for analysis.

The interrogation program may include a set of requests delivered in a sequence, and a set of responses, where the set of requests at least partially depends on the set of responses. The set of requests and the set of responses may be interleaved. For example, processing circuitry may output a first request, receive a first response to the first request, output a second request based on the first response, receive a second response, and so on. As such, the interrogation program may represent a logical flow which may proceed based on the set of responses received by processing circuitry.

Processing circuitry may output, for display by user interface 356, a request to identify whether an undesirable attribute occurred during a performance of the action (1714). For example, processing circuitry may output a request which includes the message "Was some attribute of the paresthesia undesirable while performing the action? (Yes or No)." In this way, the request to identify whether an undesirable attribute occurred during the performance of the action may represent a first request of a set of requests, the first request prompting the user to identify whether the action caused an undesirable attribute (e.g., undesirable sensation). Processing circuitry may receive, from external programmer 300, a response to the request to identify whether the undesirable attribute occurred during the performance of the action (1716). Responsive to receiving a response which identifies that an undesirable attribute occurred during the performance of the action ("YES" branch of block 1716), processing circuitry may output one or more requests for an identification of an identity of the undesirable attribute (1718). For example, processing circuitry may output the message "Select the paresthesia attribute that was undesirable DURING the action: too intense, pulsating feeling, increased location, or none."

The one or more requests for the identification of the identity of the undesirable attribute may include a request corresponding to each undesirable attribute of a set of undesirable attribute including but not limited, e.g., high intensity, pulsating feeling, and increased or undesired location. Processing circuitry outputs a request for an indication as to whether an intensity of stimulation delivered by IMD 110 is uncomfortably high during the performance of the action (1720). In response to receiving a response that the intensity of the stimulation is not uncomfortably high during the performance of the action ("NO" branch of block 1720), processing circuitry outputs a request as to whether the undesirable attribute represents an increased location sensation (1722). In response to receiving a response that the undesirable attribute is not an increased location sensation ("NO" branch of block 1722), processing circuitry outputs a request as to whether the undesirable attribute represents an undesirable pulsating sensation (1724). In response to receiving a response that the undesirable attribute is not a pulsating sensation ("NO" branch of block 1722), processing circuitry may determine that the undesirable attribute is none of an uncomfortably high intensity, an increased location, or a pulsating sensation and the interrogation operation proceeds to block 1726 where processing circuitry sets an indication to request that patient 105 perform a "next" action which is different from the action corresponding to the current interrogation. It is not required for processing circuitry to output three requests (blocks 1720, 1722, 1724) each representing one of three sensations. Alternatively, in some cases, processing circuitry may output a single request including a menu of sensations for selection by patient 105.

In response to receiving a response that the intensity of the stimulation is uncomfortably high during the performance of the action ("YES" branch of block 1720), processing circuitry may output one or more requests for an identification of whether the uncomfortably high intensity occurs at a beginning of the action, occurs at an end of the action, or occurs throughout an entire period of time in which the action is performed (1728). Additionally, in response to receiving a response that the undesirable attribute is an increased location sensation ("YES" branch of block 1722), processing circuitry may output one or more requests for an identification of whether the uncomfortable increased location sensation occurs at a beginning of the action, occurs at an end of the action, or occurs throughout an entire period of time in which the action is performed (1730). In this way, processing circuitry may output a prompt for information as to when the undesirable attribute occurs relative to the action in both cases where the undesirable attribute represents an uncomfortably high intensity and where the undesirable attribute represents an uncomfortably increased location of stimulation.

Processing circuitry outputs a request for an identification of whether the undesirable attribute occurs at the beginning of the performance of the action (1732). Responsive to receiving a response that the undesirable attribute does not occur at the beginning of the performance of the action ("NO" branch of block 1732), processing circuitry outputs a request for an identification of whether the undesirable attribute occurs at the end of the performance of the action (1734). Responsive to receiving a response that the undesirable attribute does not occur at the end of the performance of the action ("NO" branch of block 1734), processing circuitry determines that the undesirable attribute occurs throughout the performance of the action and processing circuitry outputs a request for an identification of whether an overstimulation threshold of IMD 110 is currently higher than a desirable overstimulation threshold value (1736).

It may be beneficial for processing circuitry to determine whether the uncomfortable sensation occurs at the beginning of the action, at the end of the action, consistently throughout the performance of the action, or intermittently throughout the performance of the action. As such, processing circuitry may determine one or more control policy changes to be implemented such that the same action, when performed again, will not cause the same undesirable attribute felt by patient 105 during the interrogation operation of FIGS. 17A-17B.

In response to receiving a response that the undesirable attribute occurs at the beginning of the performance of the action ("YES" branch of block 1732), processing circuitry may generate a recommendation to increase a decrement step size of one or more stimulation pulses delivered by IMD 110 (1738). In response to receiving a response that the undesirable attribute occurs at the end of the performance of the action ("YES" branch of block 1734), processing circuitry may generate a recommendation to decrease an increment step size of one or more stimulation pulses delivered by IMD 110 (1740). The action which processing circuitry prompts patient 105 to perform may represent a transient patient action which moves one or more electrodes of lead 130 closer to target tissue of patient 105, causing IMD 110 to decrement an amplitude of stimulation pulses delivered to the target tissue at a beginning of the transient patient action and increment an amplitude of stimulation pulses delivered to the target tissue at an end of the transient patient action.

When processing circuitry receives an indication that an uncomfortable sensation occurs at the beginning of the action, it may be beneficial for processing circuitry to recommend increasing the decrement step size of stimulation pulses delivered by IMD 110 such that, if the recommendation is implemented, stimulation pulses are decreased at a greater rate of speed as compared with a time prior to the recommendation by processing circuitry. Additionally, when processing circuitry receives an indication that an uncomfortable sensation occurs at the end of the action, it may be beneficial for processing circuitry to recommend decreasing the increment step size of stimulation pulses delivered by IMD 110 such that, if the recommendation is implemented, stimulation pulses are increased at a lesser rate of speed as compared with a time prior to the recommendation by processing circuitry. Such recommendations by processing circuitry, if implemented, may decrease a likelihood that patient 105 experiences an uncomfortable stimulation (e.g., transient overstimulation) in the future while performing the same action prompted by processing circuitry as a part of the interrogation operation.

When processing circuitry receives an indication that the overstimulation threshold is currently higher than a desirable overstimulation threshold value ("YES" branch of block 1736), processing circuitry may generate a recommendation to decrease the overstimulation threshold. When processing circuitry receives an indication that the overstimulation threshold is not currently higher than a desirable overstimulation threshold value ("NO" branch of block 1736), processing circuitry may generate a recommendation to decrease a buffer zone lower boundary of one or more stimulation pulses delivered by IMD 110 (1744). The buffer zone may represent a range of ECAP amplitudes for which the IMD 110 holds stimulation element constant. As such, by decreasing the buffer zone lower boundary, IMD 110 may decrease the threshold for increasing stimulation amplitude.

When processing circuitry receives a response that the undesirable attribute represents an undesirable pulsating sensation ("YES" branch of block 1724), processing circuitry may determine whether an increment rate (e.g., increment step size) of one or more stimulation pulses delivered by IMD 110 is greater than a desirable increment rate value. When processing circuitry determines that the increment rate is greater than the desirable increment rate value ("YES" branch of block 1746), processing circuitry may generate a recommendation to decrease the increment rate (1748). When processing circuitry determines that the increment rate is not greater than the desirable increment rate value ("NO" branch of block 1746), processing circuitry may generate a recommendation to increase a size of a hysteresis band for more stimulation pulses delivered by IMD 110 (1750).

In response to generating the recommendation to increase the decrement rate (e.g., decrement step size) of one or more stimulation pulses delivered by IMD 110, generating the recommendation to decrease the increment rate of one or more stimulation pulses delivered by IMD 110, generating the recommendation to decrease the overstimulation threshold, generating a recommendation to increase a buffer zone size, or generating the suggestion to decrease the buffer zone lower boundary, processing circuitry may set an indication to prompt patient 105 to repeat the same action (1752) as the action prompted by processing circuitry during the present interrogation operation. As such, the interrogation operation of FIGS. 17A-17B may be repeated, causing processing circuitry to prompt patient 105 to perform the same action over again and allowing processing circuitry to evaluate the same action again.

When processing circuitry receives a response to request to identify whether an undesirable attribute occurred during a performance of the action indicating that an undesirable attribute did not occur during the performance of the action ("NO" branch of block 1716), processing circuitry may output a request for information as to whether an undesirable attribute occurs after the performance of the action (1754)

and processing circuitry may receive a response to the request (1756). When the response indicates an undesirable attribute did not occur after the performance of the action ("NO" branch of block 1756), processing circuitry may determine whether to repeat the interrogation operation. When the response indicates an undesirable attribute does occur after the performance of the action ("YES" branch of block 1756), processing circuitry may output, for display by the user interface, a request for information as to an identity of the undesirable attribute which occurs after the performance of the action (1758). For example, processing circuitry may output the message: "Select the paresthesia attribute that was undesirable AFTER the action: too intense, temporary loss of paresthesia, none" for display by the user interface. Processing circuitry may receive a response that the stimulation intensity is uncomfortably high (1760). In this case, processing circuitry generates a recommendation to decrease a maximum stimulation amplitude (1764). Processing circuitry may receive a response that the uncomfortable sensation represents a temporary loss of paresthesia (1762). In this case, processing circuitry generates a recommendation to increase an increment step size of one or more stimulation pulses generated by IMD 110 (1766).

If processing circuitry determines that the undesirable attribute occurring after the sensation is neither related to high intensity or temporary loss of paresthesia, the interrogation operation may proceed to block 1726 and processing circuitry may set an indication to perform the next action. In response to generating the recommendations of blocks 1764 and 1766, processing circuitry may set an indication to prompt patient 105 to repeat the same action (1752) as the action prompted by processing circuitry during the present interrogation operation. At block 1772, processing circuitry may determine whether to restart the interrogation operation by generating a request for patient 105 to perform an action or end the process.

Figure 18:
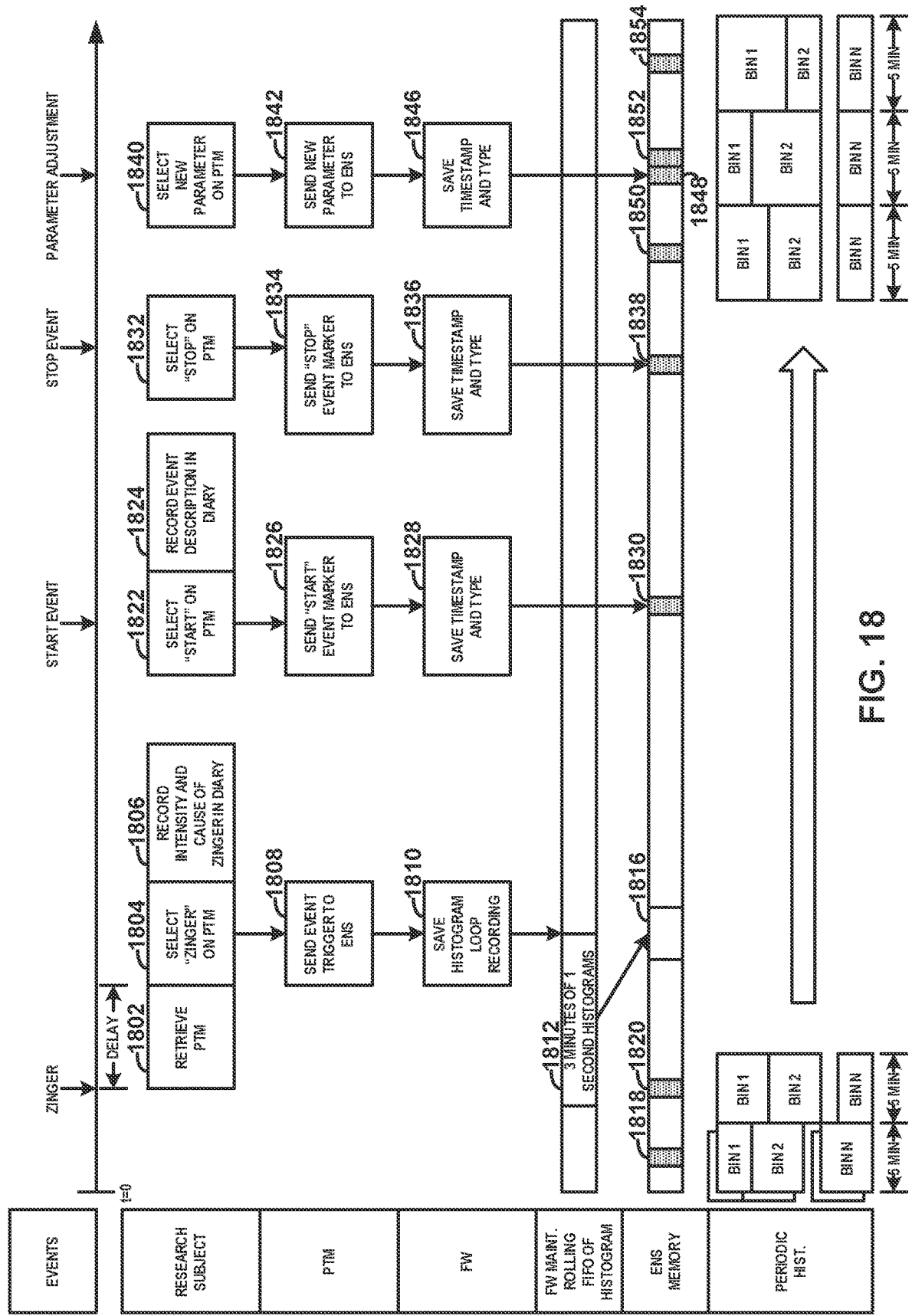
FIG. 18 is a flow diagram illustrating an example for saving one or more sets of histogram data, in accordance with one or more techniques of this disclosure.

FIG. 18 is a flow diagram illustrating an example for saving one or more sets of histogram data, in accordance with one or more techniques of this disclosure. FIG. 18 is described with respect to IMD 110 and external programmer 150 of FIG. 1, IMD 200 of FIG. 2, and external programmer 300 of FIG. 3. However, the techniques of FIG. 18 may be performed by different components of IMD 110, external programmer 150, IMD 200, and external programmer 300, or by additional or alternative medical devices.

When utilizing evoked compound action potentials (ECAPs) as inputs to estimate a volume of tissue activation during the delivery of electrical current to the nervous system (e.g., spinal cord), a need exists to record attributes of the physiological signal and delivery system which are then correlated to patient 105's perception of the therapy and/or therapy efficacy. If too much tissue is activated, the patient may feel a sharp increase in stimulation or perceived paresthesia from the stimulation delivered by IMD 110 or similar unwanted side-effects. If too little tissue is activated, the patient may experience a loss of therapeutic benefit and a return of symptoms. A control policy executed by IMD 110 measures the tissue activation and adjusts stimulation based on a volume of tissue activated.

During a configuration and adjustment of the control policy executed by IMD 110, measurements of one or more characteristics may be used to allow continued refinement of the control policy, including characteristics such as a patient input of an intensity of an undesirable attribute, various features of an ECAP at a time of the undesirable attribute, a stimulation amplitude at a time of the undesirable attribute, response times of the control policy at the time of the undesirable attribute, and background symptom levels. Data collection throughout the day is also needed even when the patient is not perceiving unwanted side-effects. For example, the control policy may be oversensitive to potential undesirable attributes and therefore drive the delivered stimulation amplitude down which in turn causes a return of symptoms and/or a loss of paresthesia. In these cases, the system could be responding too soon to measured biomarkers that are not accurately indicating a potential undesirable attribute. This data shall be used to evaluate how effective ECAP stimulation control is at improving pain management and patient comfort. This needs to be evaluated relative to optimization of the system parameters.

This disclosure describes one or more techniques for addressing a need to collect the attributes introduced above with a limited amount of memory located on IMD 110. For example, it might not be possible to continuously collect histogram data over several days or weeks and store the histogram data to a memory. As such, IMD 110 may periodically collect histogram data for a period of time, within the limits of the IMD 110 memory. The durations and resolutions of histograms generated by IMD 110 may be configurable.

IMD 110 may collect periodic sets of histogram data continuously in the background for one or more of a set of attributes. The set of attributes may include stimulation amplitudes, ECAP feature amplitudes, an amount of time in each control policy state, and motion signal amplitudes. In some examples, each set of histogram data may correspond to a window of time. In some examples, a duration of the window of time may be within a range from 3 minutes to 10 minutes (e.g., 5 minutes), but this is not required. The duration of the window of time of the histogram may be greater than 10 minutes or less than 3 minutes, in some examples. Since each patient's amplitude ranges for the attributes are different, the histogram bin "dividers" are configurable.

IMD 110 may also collect rolling buffer histogram data (smaller time duration of each histogram results in higher temporal resolution in overall recording). This histogram buffer is not saved to recording memory until an external indication is received from the patient indicating that an undesirable attribute was experienced. The idea is that the 3-minute buffer will be long enough in duration to capture the characteristics of the undesirable attribute which occurred before the patient trigger. When an undesirable attribute is experienced, the patient needs time to retrieve the patient programmer, start the programmer, and send the trigger.

Other external events may be correlated to the physiological conditions, such as when the patient starts and stops an activity (e.g. going for a walk, going to sleep) and when the patient adjusts some parameter of the system (e.g., control policy threshold). These events are recorded as time stamps which then can be indexed into the periodic histograms during post processing.

In some examples, patient 105 may retrieve external programmer 150 (1802) in response to experiencing an undesirable attribute. External programmer 150 receives a user input indicating an undesirable attribute (e.g., "zinger") (1804). Additionally, in some cases, external programmer 150 may receive data indicative of a cause of the undesirable attribute and an intensity of the undesirable attribute. The external programmer 150 records the intensity of the undesirable attribute and the cause of the undesirable attribute in storage device 354 (1806).

In response to receiving the user input indicating the undesirable attribute, external programmer 150 sends an event trigger to IMD 110 (1808), where the event trigger indicates the user identification of the undesirable attribute. IMD 110 may save histogram data stored in a rolling buffer of IMD 110 (1810). For example, the histogram data stored by the rolling buffer at a time in which IMD 110 receives the event trigger may include histogram data 1812. In order to permanently save histogram data 1812, IMD 110 may permanently save histogram data 1812 to a memory of IMD 110. The permanently stored histogram data may include histogram data 1816.

IMD 110 may, in some cases, permanently store sets of histogram data on a regular basis. For example, histogram data set 1818, histogram data set 1820, histogram data set 1850, histogram data set 1852, and histogram data set 1854 may represent histogram data sets which are stored by IMD 110 on a regular basis. In some examples, IMD 110 may automatically store histogram data sets according to a predetermined frequency (e.g., hourly, daily). These automatically recorded histogram data sets may each correspond to a window of time having a predetermined length (e.g., 5 minutes).

In some examples, IMD 110 may also permanently save information (e.g., an event type and a timestamp) corresponding to an event indicated by patient 105. For example, external programmer 150 may receive user input indicating a start of an event (1822). Additionally, external programmer 150 may also receive information indicative of a description of the event. External programmer 150 records the information indicative of the description of the event in a memory (1824). External programmer 150 sends a message indicating a first timestamp marking the start of the event to IMD 110 (1826). IMD 110 saves the first timestamp marking the start of the event and saves a type of the event (1828). The information including the first timestamp and the type is saved to the memory of IMD 110 as information 1830. External programmer 150 may receive user input indicating an end of an event (1832). External programmer 150 sends a message indicating a second timestamp marking the end of the event to IMD 110 (1834). IMD 110 saves the second timestamp marking the end of the event (1836). Second timestamp 1838 marks the end of the event in the memory of IMD 110.

The first timestamp and the second timestamp may be applied during an analysis of histogram data automatically captured by IMD 110. For example, processing circuitry may identify first histogram data that is collected by IMD 110 closest to the time of the first timestamp and processing circuitry may identify second histogram data that is collected by IMD 110 closest to the time of the second timestamp. Processing circuitry may, in some cases, identify one or more additional sets of histogram data which occur between the first set of histogram data and the second set of histogram data (e.g., during the event). The first histogram data may indicate one or more conditions at the start of the event and the second histogram data may indicate one or more conditions at the end of the event. Processing circuitry may analyze the first histogram data and the second histogram data in order to determine whether any of the one or more conditions have changed from the start of the event to the end of the event. Based on this analysis, processing circuitry may determine whether to recommend one or more alterations to the control policy of IMD 110. Additionally, the description of the event may be applied during the analysis of the histogram data automatically captured by IMD 110. Histogram data collected by IMD 110 during or close in time to the event may be analyzed as being associated with the event, so that processing circuitry may identify one or more trends associated with the event.

Processing circuitry may record one or more timestamps corresponding to parameter changes initiated by external programmer 150. For each instance that external programmer 150 initiates a change of one or more parameters which define stimulation delivered by IMD 110, processing circuitry may record a timestamp corresponding to the parameter change. For example, external programmer 150 may receive a user selection of a new parameter (1840). External programmer 150 initiates a change to the new parameter (1842) and record a timestamp corresponding to the change to the new parameter (1846). The timestamp may be saved to a memory of the IMD 110 and/or a memory of the external programmer 150 as information 1848.

The timestamp indicating the parameter change may be applied during an analysis of histogram data automatically captured by IMD 110. For example, histogram data 1852 is collected by IMD 110 close to a time of the timestamp indicating the parameter change (e.g., information 1848). Additionally, histogram data 1850 is collected by IMD 110 before the timestamp indicating the parameter change and histogram data 1854 is collected by IMD 110 before the timestamp indicating the parameter change. As such, processing circuitry may analyze histogram data 1850, histogram data 1852, and histogram data 1854 in order to determine an effect of the parameter change on one or more aspects (e.g., a size of one or more bins) of the histogram data. In some examples, based on this analysis, processing circuitry may generate a recommendation to change the control policy of IMD 110. In some examples, based on this analysis, processing circuitry may generate a recommendation to maintain the control policy of IMD 110 at a current state.

Figure 19:
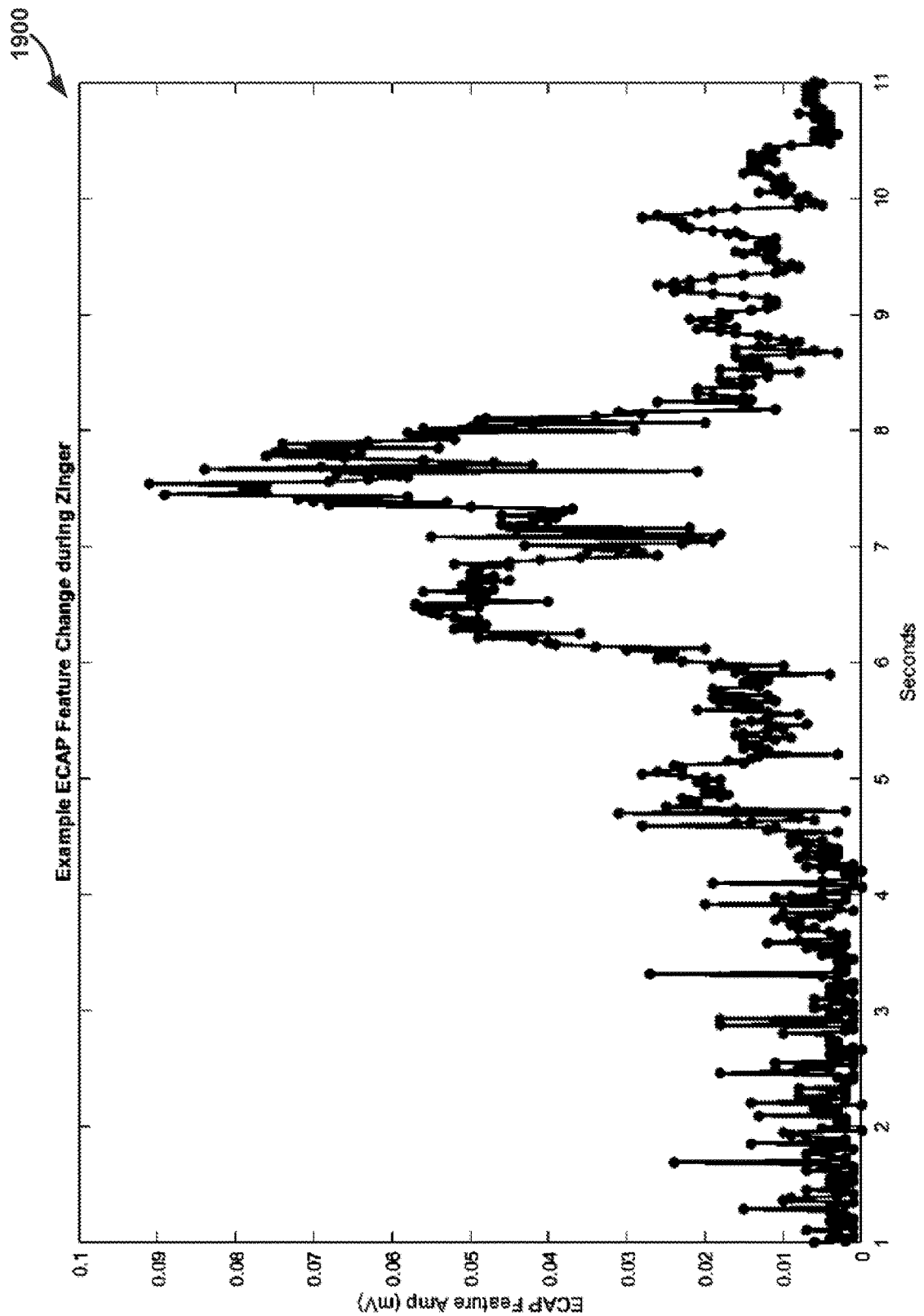
FIG. 19 is a graph illustrating ECAP amplitudes of a set of ECAPs sensed by the IMD of FIG. 1, in accordance with one or more techniques of this disclosure.

FIG. 19 is a graph 1900 illustrating ECAP amplitudes of a set of ECAPs sensed by IMD 110 over an 11 second period of time associated with a transient overstimulation event, in accordance with one or more techniques of this disclosure. In some examples, IMD 110 records the ECAPs at 50 Hz. As seen in graph 1900, ECAP amplitudes are greatest during seconds 6-8 of the plot. This increase in ECAP amplitudes may represent an uncomfortable attribute of a sensation experienced by the patient. As seen in FIG. 19, each one-second window of graph 1900 includes a set of data points, where each data point represents an amplitude of an ECAP measured by IMD 110 at the time corresponding to the position of the respective data point on the x-axis of graph 1900. Amplitudes of measured ECAPs vary within respective 1-second windows, and this variance may be seen in histogram data corresponding to the data points shown in graph 1900.

FIG. 20 is a graph 2000 which illustrates histogram data including a set of histograms corresponding to the data of graph 1900 in FIG. 19, in accordance with one or more techniques of this disclosure. As seen FIG. 20, graph 2000 includes a set of histograms 2010-2030. Although the set of histograms shown in graph 2000 includes 11 histograms (e.g., one histogram for each one second period of time of the total 11 second event), a set of histogram data representing 11 seconds may include more than 11 histograms or less than 11 histograms. For example, histogram data may include 3 minutes of one-second histograms, that is, 180 one-second histograms, in other examples. However, each "bin" of time for a respective histogram may be shorter or longer than 1 second in other examples. As seen in the example of FIG. 20, histograms 2020, 2022, and 2024 indicate that seconds 6-8 include more high-amplitude ECAPs than other histograms such as histogram 2010. This may indicate that patient 105 experiences transient over-stimulation at seconds 6-8 and the magnitude of those sensed ECAPs.

The following examples are example systems, devices, and methods described herein.

Example 1: A system includes: a user interface; and processing circuitry configured to: output, for display by the user interface, a message requesting the patient perform a set of actions; receive, from the user interface, user input indicative of a patient response associated with the set of actions; and determine, based on the user input, one or more adjustments to a control policy which controls electrical stimulation delivered by a medical device based on at least one evoked compound action potentials (ECAP) sensed by the medical device.

Example 2: The system of example 1, where the system further includes: communication circuitry configured to communicate with the medical device, where the processing circuitry is configured to output, to the medical device via the communication circuitry, an instruction to configure the one or more adjustments to the control policy.

Example 3: The system of any of examples 1-2, where the electrical stimulation includes a plurality of informed pulses and a plurality of control pulses, each control pulse of the plurality of control pulses eliciting a respective ECAP of the plurality of ECAPs, where the control policy controls, based on the plurality of ECAPs, one or more parameters corresponding to the plurality of control pulses delivered by the medical device, and where the control policy controls, based on the plurality of ECAPs, one or more parameters corresponding to the plurality of informed pulses delivered by the medical device.

Example 4: The system of any of examples 1-3, where the control policy controls one or more parameters of the electrical stimulation therapy delivered by the medical device, where the electrical stimulation therapy includes a plurality of stimulation pulses, and where to determine the one or more adjustments to the control policy, the processing circuitry is configured to: determine the one or more adjustments in order to cause the control policy to perform any one or combination of decrease a decrement step size or a decrement step rate of the plurality of stimulation pulses responsive to one or more events associated with the patient response, increase the decrement step size or the decrement step rate of the plurality of stimulation pulses responsive to the one or more events associated with the patient response, decrease an increment step size or an increment step rate of the plurality of stimulation pulses responsive to the one or more events associated with the patient response, and increase the increment step size or the increment step rate of the plurality of stimulation pulses responsive to the transient one or more events associated with the patient response.

Example 5: The system of any of examples 1-4, where the processing circuitry is further configured to: output, for display by the user interface, a set of requests, where each request of the set of requests includes a prompt for information relating to one or more patient sensations corresponding to the action, and where to receive the user input indicative of the patient response, the processing circuitry is configured to: receive, from the user interface, a set of responses, where each response of the set of responses represents a patient response to a respective request of the set of requests.

Example 6: The system of any of examples 1-5, where the processing circuitry is configured to: output, for display by the user interface, a first request of the set of requests, where the first request includes a prompt for the user to indicate whether the set of actions caused an undesirable sensation during the set of actions; and receive, from the user interface, a first response of the set of responses, where the first response includes a patient response that the set of actions caused an undesirable sensation during the set of actions or a patient response that the set of actions did not cause an undesirable sensation during the set of actions.

Example 7: The system of any of examples 1-6, where responsive to receiving the patient response that the set of actions caused an undesirable sensation during the set of actions, the processing circuitry is configured to: output, for display by the user interface, a group of second requests of the set of requests, where the group of second requests include a prompt for the user to identify the undesirable sensation from a menu of possible undesirable sensations; receive, from the user interface, a group of second responses of the set of responses, where the group of second responses include a user identification of the undesirable sensation from the menu of undesirable sensations; and determine, based on the group of second responses, the one or more adjustments to the control policy.

Example 8: The system of any of examples 1-7, where responsive to receiving the patient response that the set of actions did not cause an undesirable sensation during the set of actions, the processing circuitry is configured to: output, for display by the user interface, a second request of the set of requests, where the second request includes a prompt for the user to indicate whether the set of actions caused an undesirable sensation after the set of actions; and receive, from the user interface, a second response of the set of responses, where the second response includes a patient response that the set of actions caused an undesirable sensation after the set of actions or a patient response that the set of actions did not cause an undesirable sensation after the set of actions.

Example 9: The system of any of examples 1-8, where responsive to receiving the patient response that the set of actions caused an undesirable sensation after the set of actions, the processing circuitry is configured to: output, for display by the user interface, a group of third requests of the set of requests, where the group of third requests include a prompt for the user to identify the undesirable sensation from a menu of possible undesirable sensations; receive, from the user interface, a group of third responses of the set of responses, where the group of third responses include a user identification of the undesirable sensation from the menu of undesirable sensations; and determine, based on the group of third responses, the one or more adjustments to the control policy.

Example 10: The system of any of examples 1-9, where the set of actions is a first set of actions, where the message is a first message, and where responsive to receiving the patient response that the first set of actions did not cause an undesirable sensation after the first set of actions, the processing circuitry is configured to: determine whether to prompt the patient to perform a second set of actions; and responsive to determining to prompt the patient to perform a second set of actions, output a second message for display by the user interface, the second message requesting the patient to perform the second set of actions.

Example 11: The system of any of examples 1-10, where the processing circuitry is further configured to: output, prior to outputting the message requesting the patient to perform the set of actions, an instruction for the medical device to measure one or more parameters; and receive, from the medical device, data indicative of the one or more measured parameters, where the data corresponds to a period of time including the set of actions performed by the patient.

Example 12: The system of any of examples 1-11, where the one or more parameters include any one or combination of a stimulation amplitude of one or more stimulation pulses of the electrical stimulation therapy, characteristics of evoked compound action potentials (ECAPs) responsive to the one or more stimulation pulses, an electrogram (EGM) of the patient, a motion level of the patient, or any combination thereof.

Example 13: The system of any of examples 1-12, where the medical device includes an implantable medical device (IMD).

Example 14: The system of any of examples 1-13, where an external device includes the user interface.

Example 15: A method including: outputting, by processing circuitry for display by the user interface, a message requesting the patient perform a set of actions; receiving, by the processing circuitry from the user interface, user input indicative of a patient response associated with the set of actions; and determining, by the processing circuitry based on the user input, one or more adjustments to a control policy which controls electrical stimulation delivered by a medical device based on at least one evoked compound action potentials (ECAP) sensed by the medical device.

Example 16: The method of example 15, further including outputting, by the processing circuitry to the medical device via communication circuitry, an instruction to configure the one or more adjustments to the control policy.

Example 17: The method of any of examples 15-16, where the control policy controls one or more parameters of the electrical stimulation therapy delivered by the medical device, where the electrical stimulation therapy includes a plurality of stimulation pulses, and where to determining the one or more adjustments to the control policy includes: determining the one or more adjustments in order to cause the control policy to perform any one or combination of decrease a decrement step size or a decrement step rate of the plurality of stimulation pulses responsive to one or more events associated with the patient response, increase the decrement step size or the decrement step rate of the plurality of stimulation pulses responsive to the one or more events associated with the patient response, decrease an increment step size or an increment step rate of the plurality of stimulation pulses responsive to the one or more events associated with the patient response, and increase the increment step size or the increment step rate of the plurality of stimulation pulses responsive to the transient one or more events associated with the patient response.

Example 18: The method of any of examples 15-17, where the method further includes: outputting, by processing circuitry for display by the user interface, a set of requests, where each request of the set of requests includes a prompt for information relating to one or more patient sensations corresponding to the action, and where to receiving the user input indicative of the patient response includes: receiving, from the user interface, a set of responses, where each response of the set of responses represents a patient response to a respective request of the set of requests.

Example 19: The method of any of examples 15-18, where the method further includes: outputting, by processing circuitry for display by the user interface, a first request of the set of requests, where the first request includes a prompt for the user to indicate whether the set of actions caused an undesirable sensation during the set of actions; and receiving, by processing circuitry from the user interface, a first response of the set of responses, where the first response includes a patient response that the set of actions caused an undesirable sensation during the set of actions or a patient response that the set of actions did not cause an undesirable sensation during the set of actions.

Example 20: The method of any of examples 15-19, where responsive to receiving the patient response that the set of actions caused an undesirable sensation during the set of actions, the method further includes: outputting, by the processing circuitry for display by the user interface, a group of second requests of the set of requests, where the group of second requests include a prompt for the user to identify the undesirable sensation from a menu of possible undesirable sensations; receiving, by the processing circuitry from the user interface, a group of second responses of the set of responses, where the group of second responses include a user identification of the undesirable sensation from the menu of undesirable sensations; and determining, by the processing circuitry based on the group of second responses, the one or more adjustments to the control policy.

Example 21: The method of any of examples 15-20, where responsive to receiving the patient response that the set of actions did not cause an undesirable sensation during the set of actions, the method further includes: outputting, by the processing circuitry for display by the user interface, a second request of the set of requests, where the second request includes a prompt for the user to indicate whether the set of actions caused an undesirable sensation after the set of actions; and receiving, by the processing circuitry from the user interface, a second response of the set of responses, where the second response includes a patient response that the set of actions caused an undesirable sensation after the set of actions or a patient response that the set of actions did not cause an undesirable sensation after the set of actions.

Example 22: The method of any of examples 15-21, where responsive to receiving the patient response that the set of actions caused an undesirable sensation after the set of actions, the method further includes: outputting, by the processing circuitry for display by the user interface, a group of third requests of the set of requests, where the group of third requests include a prompt for the user to identify the undesirable sensation from a menu of possible undesirable sensations; receiving, by the processing circuitry from the user interface, a group of third responses of the set of responses, where the group of third responses include a user identification of the undesirable sensation from the menu of undesirable sensations; and determining, by the processing circuitry based on the group of third responses, the one or more adjustments to the control policy.

Example 23: The method of any of examples 15-22, where the set of actions is a first set of actions, where the message is a first message, and where responsive to receiving the patient response that the first set of actions did not cause an undesirable sensation after the first set of actions, the method further includes: determining, by the processing circuitry, whether to prompt the patient to perform a second set of actions; and responsive to determining to prompt the patient to perform a second set of actions, outputting, by the processing circuitry, a second message for display by the user interface, the second message requesting the patient to perform the second set of actions.

Example 24: The method of any of examples 15-23, further including: outputting, by the processing circuitry prior to outputting the message requesting the patient to perform the set of actions, an instruction for the medical device to measure one or more parameters; and receiving, by the processing circuitry from the medical device, data indicative of the one or more measured parameters, where the data corresponds to a period of time including the set of actions performed by the patient.

Example 25: A computer-readable medium including instructions that, when executed by a processor, causes the processor to: output, for display by the user interface, a message requesting the patient perform a set of actions; receive, from the user interface, user input indicative of a patient response associated with the set of actions; and determine, based on the user input, one or more adjustments to a control policy which controls electrical stimulation delivered by a medical device based on at least one evoked compound action potentials (ECAP) sensed by the medical device.

Example 26: A medical device including: stimulation generation circuitry configured to deliver electrical stimulation to a patient, where the electrical stimulation therapy includes a plurality of stimulation pulses; sensing circuitry configured to sense one or more evoked compound action potentials (ECAPs), where the sensing circuitry is configured to sense each ECAP of the one or more ECAPs elicited by a respective stimulation pulse of the plurality of stimulation pulses; and processing circuitry configured to store a set of histogram data corresponding to a set of ECAPs of the plurality of ECAPs, the set of ECAPs being sensed by the sensing circuitry over a window of time.

Example 27: The medical device of example 26, where the set of histogram data includes a set of histogram bins, where each histogram bin of the set of histogram bins corresponds to a range of ECAP parameter values, and where each histogram bin of the set of histogram bins includes a number of ECAPs of the set of ECAPs that are associated with a parameter value within the respective range of ECAP parameter values.

Example 28: The medical device of any of examples 26-27, where the processing circuitry is further configured to: receive information indicative of a patient response; and capture, in response to receiving the user input indicative of the patient response, the set of histogram data in a memory, where the set of histogram data includes data representative of the patient response.

Example 29: The medical device of any of examples 26-28, where to store the set of histogram data, the processing circuitry is configured to temporarily store the set of histogram data in a rolling buffer which updates as time progresses.

Example 30: The medical device of any of examples 26-29, where the processing circuitry is configured to: capture the set of histogram data stored in the rolling buffer at a time in which the processing circuitry receives the user input indicative of the patient response, where the window of time extends from a first time to a second time representing the time in which the processing circuitry receives the user input or a time after the processing circuitry receives the user input, and where the window of time includes a period of time in which the patient response occurs.

Example 31: The medical device of any of examples 26-30, where the processing circuitry is configured to: capture the set of histogram data stored in the rolling buffer at a time following the time in which the processing circuitry receives the user input indicative of the patient response, where the window of time extends from a first time to a second time representing the time in following the time in which the processing circuitry receives the user input, and where the window of time includes a period of time in which the patient response occurs.

Example 32: The medical device of any of examples 26-31, where the processing circuitry is configured to: receive a user request to set one or more histogram parameters for collecting the set of histogram data; and set, based on the user request, the one or more histogram parameters, where the one or more histogram parameters include a set of parameter ranges which define one or more histogram bins included in a set of histogram bins of the histogram data.

Example 33: The medical device of any of examples 26-32, where the set of histogram data includes: a first histogram corresponding to stimulation pulse amplitude values of a set of stimulation pulses delivered by the stimulation generation circuitry; and a second histogram corresponding to ECAP amplitude values of ECAPs sensed by the sensing circuitry responsive to the set of stimulation pulses delivered by stimulation generation circuitry.

Example 34: The medical device of any of examples 26-33, where the window of time is a first window of time, where the set of histogram data includes a first set of histogram data, and where the processing circuitry is further configured to: store a plurality of second sets of histogram data, where each second set of histogram data of the plurality of the second sets of histogram data correspond to one or more ECAPs being sensed by the sensing circuitry over a second window of time of a plurality of second windows of time; and capture each second set of histogram data of the plurality of second sets of histogram data to a memory.

Example 35: The medical device of any of examples 26-34, where the processing circuitry is configured to: receive a user report of a start of a patient activity; save a first timestamp corresponding to the start of the patient activity; receive a user report of an end of a patient activity; and save a second timestamp corresponding to the end of the patient activity, where the first timestamp corresponds to one of the plurality of second sets of histogram data and the second timestamp corresponds to one of the plurality of second sets of histogram data.

Example 36: A method including: delivering, by stimulation generation circuitry, electrical stimulation to a patient, where the electrical stimulation therapy includes a plurality of stimulation pulses; sensing, by sensing circuitry, one or more evoked compound action potentials (ECAPs), where the sensing circuitry is configured to sense each ECAP of the one or more ECAPs elicited by a respective stimulation pulse of the plurality of stimulation pulses; and storing, by processing circuitry, a set of histogram data corresponding to a set of ECAPs of the plurality of ECAPs, the set of ECAPs being sensed by the sensing circuitry over a window of time.

Example 37: The method of example 36, where the set of histogram data includes a set of histogram bins, where each histogram bin of the set of histogram bins corresponds to a range of ECAP parameter values, and where each histogram bin of the set of histogram bins includes a number of ECAPs of the set of ECAPs that are associated with a parameter value within the respective range of ECAP parameter values.

Example 38: The method of any of examples 36-37, where the method further includes: receiving, by the processing circuitry, information indicative of a patient response; and capturing, by the processing circuitry in response to receiving the user input indicative of the patient response, the set of histogram data in a memory, where the set of histogram data includes data representative of the patient response.

Example 39: The method of any of examples 36-38, where storing the set of histogram data includes temporarily storing the set of histogram data in a rolling buffer which updates as time progresses.

Example 40: The method of any of examples 36-39, where the method further includes: capturing, by the processing circuitry, the set of histogram data stored in the rolling buffer at a time in which the processing circuitry receives the user input indicative of the patient response, where the window of time extends from a first time to a second time representing the time in which the processing circuitry receives the user input or a time after the processing circuitry receives the user input, and where the window of time includes a period of time in which the patient response occurs.

Example 41: The method of any of examples 36-40, where the method further includes: capturing, by the processing circuitry, the set of histogram data stored in the rolling buffer at a time following the time in which the processing circuitry receives the user input indicative of the patient response, where the window of time extends from a first time to a second time representing the time in following the time in which the processing circuitry receives the user input, and where the window of time includes a period of time in which the patient response occurs.

Example 42: The method of any of examples 36-41, where the method further includes: receiving, by the processing circuitry, a user request to set one or more histogram parameters for collecting the set of histogram data; and setting, by the processing circuitry based on the user request, the one or more histogram parameters, where the one or more histogram parameters include a set of parameter ranges which define one or more histogram bins included in a set of histogram bins of the histogram data.

Example 43: The method of any of examples 36-42, where the window of time is a first window of time, where the set of histogram data includes a first set of histogram data, and where the method further includes: storing, by the processing circuitry, a plurality of second sets of histogram data, where each second set of histogram data of the plurality of the second sets of histogram data correspond to one or more ECAPs being sensed by the sensing circuitry over a second window of time of a plurality of second windows of time; and capturing, by the processing circuitry, each second set of histogram data of the plurality of second sets of histogram data to a memory.

Example 44: The method of any of examples 36-43, where the method further including: receiving, by the processing circuitry, a user report of a start of a patient activity; saving, by the processing circuitry a first timestamp corresponding to the start of the patient activity; receiving, by the processing circuitry, a user report of an end of a patient activity; and saving, by the processing circuitry, a second timestamp corresponding to the end of the patient activity, where the first timestamp corresponds to one of the plurality of second sets of histogram data and the second timestamp corresponds to one of the plurality of second sets of histogram data.

Example 45: A computer-readable medium including instructions that, when executed by a processor, causes the processor to: deliver electrical stimulation to a patient, where the electrical stimulation therapy includes a plurality of stimulation pulses; sense one or more evoked compound action potentials (ECAPs), where the sensing circuitry is configured to sense each ECAP of the one or more ECAPs elicited by a respective stimulation pulse of the plurality of stimulation pulses; and store a set of histogram data corresponding to a set of ECAPs of the plurality of ECAPs, the set of ECAPs being sensed by the sensing circuitry over a window of time.

The techniques described in this disclosure may be implemented, at least in part, in hardware, software, firmware, or any combination thereof. For example, various aspects of the techniques may be implemented within one or more microprocessors, DSPs, ASICs, FPGAs, or any other equivalent integrated or discrete logic QRS circuitry, as well as any combinations of such components, embodied in external devices, such as physician or patient programmers, stimulators, or other devices. The terms "processor" and "processing circuitry" may generally refer to any of the foregoing logic circuitry, alone or in combination with other logic circuitry, or any other equivalent circuitry, and alone or in combination with other digital or analog circuitry.

For aspects implemented in software, at least some of the functionality ascribed to the systems and devices described in this disclosure may be embodied as instructions on a computer-readable storage medium such as RAM, DRAM, SRAM, FRAM, magnetic discs, optical discs, flash memory, or forms of EPROM or EEPROM. The instructions may be executed to support one or more aspects of the functionality described in this disclosure.

In addition, in some aspects, the functionality described herein may be provided within dedicated hardware and/or software modules. Depiction of different features as modules or units is intended to highlight different functional aspects and does not necessarily imply that such modules or units must be realized by separate hardware or software components. Rather, functionality associated with one or more modules or units may be performed by separate hardware or software components or integrated within common or separate hardware or software components. Also, the techniques could be fully implemented in one or more circuits or logic elements. The techniques of this disclosure may be implemented in a wide variety of devices or apparatuses, including an IMD, an external programmer, a combination of an IMD and external programmer, an integrated circuit (IC) or a set of ICs, and/or discrete electrical circuitry, residing in an IMD and/or external programmer.

What is claimed is:

1. A system comprising:
   a user interface; and
   processing circuitry configured to:
      output, for display by the user interface, a message requesting the patient perform a set of physical movement actions;
      receive, from the user interface, user input indicative of a patient response associated with the set of physical movement actions; and
      determine, based on the user input, one or more adjustments to a control policy which controls electrical stimulation delivered by a medical device based on at least one evoked compound action potentials (ECAP) sensed by the medical device.

2. The system of claim 1, wherein the system further comprises:
   communication circuitry configured to communicate with the medical device,
   wherein the processing circuitry is configured to output, to the medical device via the communication circuitry, an instruction to configure the one or more adjustments to the control policy.

3. The system of claim 1,
   wherein the electrical stimulation comprises a plurality of informed pulses and a plurality of control pulses, each control pulse of the plurality of control pulses eliciting a respective ECAP of the plurality of ECAPS, wherein the control policy controls, based on the plurality of ECAPs, one or more parameters corresponding to the plurality of control pulses delivered by the medical device, and wherein the control policy controls, based on the plurality of ECAPs, one or more parameters corresponding to the plurality of informed pulses delivered by the medical device.

4. The system of claim 1, wherein the control policy controls one or more parameters of the electrical stimulation therapy delivered by the medical device, wherein the electrical stimulation therapy comprises a plurality of stimulation pulses, and wherein to determine the one or more adjustments to the control policy, the processing circuitry is configured to:

determine the one or more adjustments in order to cause the control policy to perform any one or combination of decrease a decrement step size or a decrement step rate of the plurality of stimulation pulses responsive to one or more events associated with the patient response, increase the decrement step size or the decrement step rate of the plurality of stimulation pulses responsive to the one or more events associated with the patient response, decrease an increment step size or an increment step rate of the plurality of stimulation pulses responsive to the one or more events associated with the patient response, and increase the increment step size or the increment step rate of the plurality of stimulation pulses responsive to the transient one or more events associated with the patient response.

5. The system of claim 1, wherein the processing circuitry is further configured to:

output, for display by the user interface, a set of requests, wherein each request of the set of requests comprises a prompt for information relating to one or more patient sensations corresponding to the action, and wherein to receive the user input indicative of the patient response, the processing circuitry is configured to:

receive, from the user interface, a set of responses, wherein each response of the set of responses represents a patient response to a respective request of the set of requests.

6. The system of claim 5, wherein the processing circuitry is configured to:

output, for display by the user interface, a first request of the set of requests, wherein the first request includes a prompt for the user to indicate whether the set of physical movement actions caused an undesirable sensation during the set of physical movement actions; and receive, from the user interface, a first response of the set of responses, wherein the first response comprises a patient response that the set of physical movement actions caused an undesirable sensation during the set of physical movement actions or a patient response that the set of physical movement actions did not cause an undesirable sensation during the set of physical movement actions.

7. The system of claim 6, wherein responsive to receiving the patient response that the set of physical movement actions lead to one or more undesirable sensations during the set of physical movement actions, the processing circuitry is configured to:

output, for display by the user interface, a group of second requests of the set of requests, wherein the group of second requests include a prompt for the user to identify the undesirable sensation from a menu of possible undesirable sensations;

receive, from the user interface, a group of second responses of the set of responses, wherein the group of second responses comprise a user identification of the undesirable sensation from the menu of undesirable sensations; and determine, based on the group of second responses, the one or more adjustments to the control policy.

8. The system of claim 6, wherein responsive to receiving the patient response that the set of physical movement actions did not cause an undesirable sensation during the set of physical movement actions, the processing circuitry is configured to:

output, for display by the user interface, a second request of the set of requests, wherein the second request includes a prompt for the user to indicate whether the set of physical movement actions caused an undesirable sensation after the set of physical movement actions; and receive, from the user interface, a second response of the set of responses, wherein the second response comprises a patient response that the set of physical movement actions caused an undesirable sensation after the set of physical movement actions or a patient response that the set of physical movement actions did not cause an undesirable sensation after the set of physical movement actions.

9. The system of claim 8, wherein responsive to receiving the patient response that the set of physical movement actions caused an undesirable sensation after the set of physical movement actions, the processing circuitry is configured to:

output, for display by the user interface, a group of third requests of the set of requests, wherein the group of third requests include a prompt for the user to identify the undesirable sensation from a menu of possible undesirable sensations;

receive, from the user interface, a group of third responses of the set of responses, wherein the group of third responses comprise a user identification of the undesirable sensation from the menu of undesirable sensations; and determine, based on the group of third responses, the one or more adjustments to the control policy.

10. The system of claim 9, wherein the set of physical movement actions is a first set of physical movement actions, wherein the message is a first message, and wherein responsive to receiving the patient response that the first set of physical movement actions did not cause an undesirable sensation after the first set of physical movement actions, the processing circuitry is configured to:

determine whether to prompt the patient to perform a second set of physical movement actions; and responsive to determining to prompt the patient to perform a second set of physical movement actions, output a second message for display by the user interface, the second message requesting the patient to perform the second set of physical movement actions.

11. The system of claim 1, wherein the processing circuitry is further configured to:

output, prior to outputting the message requesting the patient to perform the set of physical movement actions, an instruction for the medical device to measure one or more parameters; and receive, from the medical device, data indicative of the one or more measured parameters, wherein the data corresponds to a period of time including the set of physical movement actions performed by the patient.

12. The system of claim 11, wherein the one or more parameters include any one or combination of a stimulation amplitude of one or more stimulation pulses of the electrical stimulation therapy, characteristics of evoked compound action potentials (ECAPs) responsive to the one or more stimulation pulses, an electrogram (EGM) of the patient, a motion level of the patient, or any combination thereof.

13. The system of claim 1, wherein the medical device comprises an implantable medical device (IMD).

14. The system of claim 1 wherein an external device comprises the user interface.

15. A method comprising:
outputting, by processing circuitry for display by the user interface, a message requesting the patient perform a set of physical movement actions;
receiving, by the processing circuitry from the user interface, user input indicative of a patient response associated with the set of physical movement actions; and
determining, by the processing circuitry based on the user input, one or more adjustments to a control policy which controls electrical stimulation delivered by a medical device based on at least one evoked compound action potentials (ECAP) sensed by the medical device.

16. The method of claim 15, further comprising outputting, by the processing circuitry to the medical device via communication circuitry, an instruction to configure the one or more adjustments to the control policy.

17. The method of claim 15, wherein the control policy controls one or more parameters of the electrical stimulation therapy delivered by the medical device, wherein the electrical stimulation therapy comprises a plurality of stimulation pulses, and wherein to determining the one or more adjustments to the control policy comprises:
determining the one or more adjustments in order to cause the control policy to perform any one or combination of decrease a decrement step size or a decrement step rate of the plurality of stimulation pulses responsive to one or more events associated with the patient response, increase the decrement step size or the decrement step rate of the plurality of stimulation pulses responsive to the one or more events associated with the patient response, decrease an increment step size or an increment step rate of the plurality of stimulation pulses responsive to the one or more events associated with the patient response, and increase the increment step size or the increment step rate of the plurality of stimulation pulses responsive to the transient one or more events associated with the patient response.

18. The method of claim 15, wherein the method further comprises:
outputting, by processing circuitry for display by the user interface, a set of requests, wherein each request of the set of requests comprises a prompt for information relating to one or more patient sensations corresponding to the action, and wherein to receiving the user input indicative of the patient response comprises:
receiving, from the user interface, a set of responses, wherein each response of the set of responses represents a patient response to a respective request of the set of requests.

19. The method of claim 18, wherein the method further comprises:

outputting, by processing circuitry for display by the user interface, a first request of the set of requests, wherein the first request includes a prompt for the user to indicate whether the set of physical movement actions caused an undesirable sensation during the set of physical movement actions; and
receiving, by processing circuitry from the user interface, a first response of the set of responses, wherein the first response comprises a patient response that the set of physical movement actions caused an undesirable sensation during the set of physical movement actions or a patient response that the set of physical movement actions did not cause an undesirable sensation during the set of physical movement actions.

20. The method of claim 19, wherein responsive to receiving the patient response that the set of physical movement actions lead to one or more undesirable sensations during the set of physical movement actions, the method further comprises:
outputting, by the processing circuitry for display by the user interface, a group of second requests of the set of requests, wherein the group of second requests include a prompt for the user to identify the undesirable sensation from a menu of possible undesirable sensations;
receiving, by the processing circuitry from the user interface, a group of second responses of the set of responses, wherein the group of second responses comprise a user identification of the undesirable sensation from the menu of undesirable sensations; and
determining, by the processing circuitry based on the group of second responses, the one or more adjustments to the control policy.

21. The method of claim 19, wherein responsive to receiving the patient response that the set of physical movement actions did not cause an undesirable sensation during the set of physical movement actions, the method further comprises:
outputting, by the processing circuitry for display by the user interface, a second request of the set of requests, wherein the second request includes a prompt for the user to indicate whether the set of physical movement actions caused an undesirable sensation after the set of physical movement actions; and
receiving, by the processing circuitry from the user interface, a second response of the set of responses, wherein the second response comprises a patient response that the set of physical movement actions caused an undesirable sensation after the set of physical movement actions or a patient response that the set of physical movement actions did not cause an undesirable sensation after the set of physical movement actions.

22. The method of claim 21, wherein responsive to receiving the patient response that the set of physical movement actions caused an undesirable sensation after the set of physical movement actions, the method further comprises:
outputting, by the processing circuitry for display by the user interface, a group of third requests of the set of requests, wherein the group of third requests include a prompt for the user to identify the undesirable sensation from a menu of possible undesirable sensations;
receiving, by the processing circuitry from the user interface, a group of third responses of the set of responses, wherein the group of third responses comprise a user identification of the undesirable sensation from the menu of undesirable sensations; and determining, by the processing circuitry based on the group of third responses, the one or more adjustments to the control policy.

23. The method of claim 22, wherein the set of physical movement actions is a first set of physical movement actions, wherein the message is a first message, and wherein responsive to receiving the patient response that the first set of physical movement actions did not cause an undesirable sensation after the first set of physical movement actions, the method further comprises:
   determining, by the processing circuitry, whether to prompt the patient to perform a second set of physical movement actions; and
   responsive to determining to prompt the patient to perform a second set of physical movement actions, outputting, by the processing circuitry, a second message for display by the user interface, the second message requesting the patient to perform the second set of physical movement actions.

24. The method of claim 15, further comprising:
   outputting, by the processing circuitry prior to outputting the message requesting the patient to perform the set of physical movement actions, an instruction for the medical device to measure one or more parameters; and
   receiving, by the processing circuitry from the medical device, data indicative of the one or more measured parameters, wherein the data corresponds to a period of time including the set of physical movement actions performed by the patient.

25. A computer-readable medium comprising instructions that, when executed by a processor, causes the processor to:
   output, for display by the user interface, a message requesting the patient perform a set of physical movement actions;
   receive, from the user interface, user input indicative of a patient response associated with the set of physical movement actions; and
   determine, based on the user input, one or more adjustments to a control policy which controls electrical stimulation delivered by a medical device based on at least one evoked compound action potentials (ECAP) sensed by the medical device.

* * * * *